United States Patent
Nielsen et al.

(10) Patent No.: US 11,819,552 B2
(45) Date of Patent: Nov. 21, 2023

(54) ANTIBODY-DRUG CONJUGATES TARGETING UPARAP

(71) Applicants: RIGSHOSPITALET, København (DK); UNIVERSITY OF COPENHAGEN, Copenhagen (DK)

(72) Inventors: Christoffer Nielsen, Hillerød (DK); Niels Behrendt, Vaerløse (DK); Lars Henning Engelholm, Bagsvaerd (DK)

(73) Assignees: Rigshospitalet, København (DK); University of Copenhagen, Copenhagen K (DK)

( * ) Notice: Subject to any disclaimer, the term of this patent is extended or adjusted under 35 U.S.C. 154(b) by 171 days.

(21) Appl. No.: 17/166,177

(22) Filed: Feb. 3, 2021

(65) Prior Publication Data

US 2021/0162062 A1  Jun. 3, 2021

Related U.S. Application Data

(62) Division of application No. 16/074,961, filed as application No. PCT/DK2017/050024 on Feb. 3, 2017, now Pat. No. 10,940,213.

(30) Foreign Application Priority Data

Feb. 5, 2016 (DK) .......................... PA 2016 70063
Oct. 24, 2016 (DK) .......................... PA 2016 70834

(51) Int. Cl.
   *A61K 47/68* (2017.01)
   *A61P 35/00* (2006.01)
   *C07K 16/28* (2006.01)
   *C07K 16/32* (2006.01)

(52) U.S. Cl.
   CPC ...... *A61K 47/6849* (2017.08); *A61K 47/6803* (2017.08); *A61K 47/6851* (2017.08); *A61K 47/6865* (2017.08); *A61P 35/00* (2018.01); *C07K 16/28* (2013.01); *C07K 16/32* (2013.01)

(58) Field of Classification Search
   CPC ............ A61K 47/6849; A61K 47/6803; A61K 47/65; A61K 47/6817; A61K 9/0019; A61P 35/00; C07K 16/28; C07K 16/32
   See application file for complete search history.

(56) References Cited

U.S. PATENT DOCUMENTS

| | | |
|---|---|---|
| 5,773,001 A | 6/1998 | Hamann et al. |
| 8,444,983 B2 | 5/2013 | Feinstein |
| 2006/0074008 A1 | 4/2006 | Senter et al. |
| 2015/0359905 A1 | 12/2015 | Feinstein |

FOREIGN PATENT DOCUMENTS

| | | |
|---|---|---|
| EP | 2411413 A1 | 2/2012 |
| WO | 2004/035088 A1 | 4/2004 |
| WO | 2010/111198 A1 | 9/2010 |
| WO | 2013/098813 A1 | 7/2013 |
| WO | 2017/133745 A1 | 8/2017 |

OTHER PUBLICATIONS

Engelholm et al., "Targeting a novel bone degradation pathway in primary bone cancer by inactivation of the collagen receptor uPARAP/Endo 180", Journal of Pathology, 2016, 238, 120-133.
Hamilton, Antibody-drug conjugates for cancer therapy: The technological and regulatory challenges of developing drug-biologic hybrids, Biologicals, 2015, 1-15.
Jurgensen et al., "A Novel Functional Role of Collagen Glycosylation", The Journal of Biological Chemistry, Sep. 16, 2011, 286, 37, 32736-32748.
Jurgensen et al., "Complex Determinants in Specific Members of the Mannose Receptor Family Govern Collagen Endocytosis", The Journal of Biological Chemistry, Mar. 14, 2014, 289, 11, 7935-7947.
Madsen et al., "Extracellular Collagenases and the Endocytic Receptor, Urokinase Plasminogen Activator Receptor-associated Protein/Endo 180, Cooperate in Fibrolast-mediated Collagen Degradation", The Journal of Biological Chemistry, Sep. 14, 2007, 282, 37, 27037-27045.
Madsen et al., "The Non-phagocytic Route of Collagen Uptake", The Journal of Biological Chemistry, Jul. 29, 2011, 286, 30, 26996-27010.
Melander et al., "The collagen receptor uPARAP/Endo 180 in tissue degradation and cancer (Review)", International Journal of Oncology, 2015, 47, 1177-1188.
Sturge, "Endo 180 at the cutting edge of bone cancer treatment and beyond", Journal of Pathology, 2016, 238, 485-488.
Wienke et al., Mol. Biol. Cell, Sep. 2003, 14(9), 3592-3604.
Çakilkaya et al., "The Collagen Receptor uPARAP in Malignant Mesothelioma: A Potential Diagnostic Marker and Therapeutic Target", Molecular Sciences, 22, 2021, 24 pages.
Nielsen et al., The collagen receptor uPARAP/Endo180 as a novel target for antibody-drug conjugate mediated treatment of mesenchymal and leukemic cancers, Oncotarget, 2017, vol. 8, No. 27, 44605-44624.

*Primary Examiner* — Ruixiang Li
(74) *Attorney, Agent, or Firm* — BakerHostetler

(57) ABSTRACT

The present invention relates to conjugates targeting uPARAP, in particular antibody-drug conjugates (ADCs) comprising monoclonal antibodies directed against the N-terminal region of uPARAP, and their use in delivery of active agents to cells and tissues expressing uPARAP. The invention further relates to the use of said ADCs in the treatment of diseases involving uPARAP expressing cells, such as cancer.

15 Claims, 18 Drawing Sheets
Specification includes a Sequence Listing.

| | 2h9-AF647 signal (MFI) | specificity ratio |
|---|---|---|
| *uPARAP-positive cell lines* | | |
| KNS42 | 203356 | 35,4 |
| HT 1080 | 118637 | 12,2 |
| THP-1 | 81591 | 13,9 |
| U937 | 11262 | 6,9 |
| *uPARAP-negative control cell line* | | |
| CHO-K1 | 2883 | 1,2 |

Fig. 3

Cell cycle phase distribution (%)

U937 cells

| Treatment | Sub-G1 | G1 | S | G2/M |
|---|---|---|---|---|
| Control | 6,0 | 62,9 | 25,6 | 5,5 |
| 2h9-vc-MMAE | - | - | - | - |
| aTNP-vc-MMAE | 5,2 | 63,8 | 24,8 | 6,2 |
| MMAE | - | - | - | - |

THP-1 cells

| Treatment | Sub-G1 | G1 | S | G2/M |
|---|---|---|---|---|
| Control | 21,7 | 51,7 | 13,2 | 13,4 |
| 2h9-vc-MMAE | 32,8 | 21,4 | 18,9 | 26,7 |
| aTNP-vc-MMAE | 19,8 | 49,7 | 18,1 | 12,3 |
| MMAE | - | - | - | - |

HT1080

| Treatment | Sub-G1 | G1 | S | G2/M |
|---|---|---|---|---|
| Control | 14,4 | 59,8 | 15,7 | 9,3 |
| 2h9-vc-MMAE | 31,0 | 38,4 | 14,3 | 15,4 |
| aTNP-vc-MMAE | 13,5 | 59,1 | 13,6 | 13,1 |
| MMAE | - | - | - | - |

KNS42

| Treatment | Sub-G1 | G1 | S | G2/M |
|---|---|---|---|---|
| Control | 4,6 | 77 | 11,3 | 6,8 |
| 2h9-vc-MMAE | 26,8 | 19,3 | 13,2 | 38,9 |
| aTNP-vc-MMAE | 4,1 | 76 | 12,2 | 7,3 |
| MMAE | 28,8 | 15,8 | 17,1 | 36,4 |

Fig. 6

SEQUENCE LISTING

```
<160> NUMBER OF SEQ ID NOS: 59

<210> SEQ ID NO 1
<211> LENGTH: 214
<212> TYPE: PRT
<213> ORGANISM: Mus musculus

<400> SEQUENCE: 1

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Thr Leu Thr Asp Gly Val Pro Ser Arg Phe Ser Gly
    50                  55                  60

Ala Gly Ser Gly Thr Lys Phe Ser Leu Lys Ile Ser Ser Leu Gln Ala
65                  70                  75                  80

Glu Asp Phe Ala Ser Tyr Phe Cys Gln Glu Phe Phe Ser Thr Pro Phe
                85                  90                  95

Thr Phe Gly Ser Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Gly Glu Arg Gln Asn Gly Val Leu
145                 150                 155                 160
```

```
Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 2
<211> LENGTH: 11
<212> TYPE: PRT
<213> ORGANISM: Mus musculus

<400> SEQUENCE: 2

```
Leu Ala Ser Gln Thr Ile Gly Thr Trp Leu Ala
1               5                   10
```

<210> SEQ ID NO 3
<211> LENGTH: 7
<212> TYPE: PRT
<213> ORGANISM: Mus musculus

<400> SEQUENCE: 3

```
Ala Ala Thr Thr Leu Thr Asp
1               5
```

<210> SEQ ID NO 4
<211> LENGTH: 9
<212> TYPE: PRT
<213> ORGANISM: Mus musculus

<400> SEQUENCE: 4

```
Gln Glu Phe Phe Ser Thr Pro Phe Thr
1               5
```

<210> SEQ ID NO 5
<211> LENGTH: 446
<212> TYPE: PRT
<213> ORGANISM: Mus musculus

<400> SEQUENCE: 5

```
Gln Val Gln Leu Gln Gln Pro Gly Thr Glu Leu Val Arg Pro Gly Leu
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile
        35                  40                  45

Gly Met Ile His Pro Ser Asn Asp Glu Lys Arg Ile Asn Gln Lys Phe
    50                  55                  60

Lys Asp Lys Ala Thr Leu Thr Val Asp Lys Phe Ser Ser Thr Val Tyr
65                  70                  75                  80

Met Gln Val Ser Ser Pro Thr Ser Glu Asp Ser Ala Val Tyr Tyr Cys
                85                  90                  95

Ala Arg Gly Gly Gly Asp Tyr Val Gly Asp Tyr Ala Leu Asp Phe Trp
            100                 105                 110

Gly Gln Gly Thr Ser Val Thr Val Ser Ser Ala Lys Thr Thr Pro Pro
        115                 120                 125

Ser Val Tyr Pro Leu Ala Pro Gly Ser Ala Ala Gln Thr Asn Ser Met
    130                 135                 140
```

```
Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
            165                 170                 175

Ala Val Leu Gln Ser Asp Leu Tyr Thr Leu Ser Ser Ser Val Thr Val
        180                 185                 190

Pro Ser Ser Thr Trp Pro Ser Glu Thr Val Thr Cys Asn Val Ala His
    195                 200                 205

Pro Ala Ser Ser Thr Lys Val Asp Lys Lys Ile Val Pro Arg Asp Cys
210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Asn Ser Thr Phe Arg Ser Val Ser Glu
290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
370                 375                 380

Gln Pro Ala Glu Asn Tyr Lys Asn Thr Gln Pro Ile Met Asp Thr Asp
385                 390                 395                 400

Gly Ser Tyr Phe Ile Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Lys
        435                 440                 445

<210> SEQ ID NO 6
<211> LENGTH: 5
<212> TYPE: PRT
<213> ORGANISM: Mus musculus

<400> SEQUENCE: 6

Ser Tyr Trp Met Asn
1               5

<210> SEQ ID NO 7
<211> LENGTH: 17
<212> TYPE: PRT
<213> ORGANISM: Mus musculus

<400> SEQUENCE: 7

Met Ile His Pro Ser Asn Asp Glu Lys Arg Ile Asn Gln Lys Phe Lys
1               5                   10                  15
```

Asp

<210> SEQ ID NO 8
<211> LENGTH: 13
<212> TYPE: PRT
<213> ORGANISM: Mus musculus

<400> SEQUENCE: 8

Gly Gly Gly Asp Tyr Val Gly Asp Tyr Ala Leu Asp Phe
1               5                   10

<210> SEQ ID NO 9
<211> LENGTH: 214
<212> TYPE: PRT
<213> ORGANISM: Mus musculus

<400> SEQUENCE: 9

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Thr Leu Thr Asp Gly Val Pro Ser Arg Phe Ser Gly
50                  55                  60

Ala Gly Ser Gly Thr Lys Phe Ser Leu Lys Ile Ser Ser Leu Gln Ala
65                  70                  75                  80

Glu Asp Phe Ala Ser Tyr Phe Cys Gln Glu Phe Phe Ser Thr Pro Phe
                85                  90                  95

Thr Phe Gly Ser Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 10
<211> LENGTH: 224
<212> TYPE: PRT
<213> ORGANISM: Mus musculus

<400> SEQUENCE: 10

Gln Val Gln Leu Gln Gln Pro Gly Thr Glu Leu Val Arg Pro Gly Leu
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Gly Gln Gly Leu Glu Trp Ile

-continued

```
                35                  40                  45
Gly Met Ile His Pro Ser Asn Asp Glu Lys Arg Ile Asn Gln Lys Phe
 50                  55                  60

Lys Asp Lys Ala Thr Leu Thr Val Asp Lys Phe Ser Ser Thr Val Tyr
 65                  70                  75                  80

Met Gln Val Ser Ser Pro Thr Ser Glu Asp Ser Ala Val Tyr Tyr Cys
                 85                  90                  95

Ala Arg Gly Gly Gly Asp Tyr Val Gly Asp Tyr Ala Leu Asp Phe Trp
                100                 105                 110

Gly Gln Gly Thr Ser Val Thr Val Ser Ser Ala Lys Thr Thr Pro Pro
                115                 120                 125

Ser Val Tyr Pro Leu Ala Pro Gly Ser Ala Ala Gln Thr Asn Ser Met
                130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Gln Ser Asp Leu Tyr Thr Leu Ser Ser Ser Val Thr Val
                180                 185                 190

Pro Ser Ser Thr Trp Pro Ser Glu Thr Val Thr Cys Asn Val Ala His
                195                 200                 205

Pro Ala Ser Ser Thr Lys Val Asp Lys Lys Ile Val Pro Arg Asp Cys
                210                 215                 220

<210> SEQ ID NO 11
<211> LENGTH: 107
<212> TYPE: PRT
<213> ORGANISM: Mus musculus

<400> SEQUENCE: 11

Asp Ile Val Met Thr Gln Ser Gln Lys Phe Met Ser Thr Ser Leu Gly
  1               5                  10                  15

Ala Arg Val Ser Ile Thr Cys Lys Ala Ser Gln Asn Val Gly Ser Asn
                 20                  25                  30

Val Val Trp Tyr Gln Gln Lys Leu Gly Gln Ser Pro Lys Ala Leu Ile
                 35                  40                  45

Tyr Ser Ala Ser Ser Arg Phe Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Thr Tyr Pro Leu
                 85                  90                  95

Ala Phe Gly Ala Gly Thr Lys Leu Glu Leu Lys
                100                 105

<210> SEQ ID NO 12
<211> LENGTH: 11
<212> TYPE: PRT
<213> ORGANISM: Mus musculus

<400> SEQUENCE: 12

Lys Ala Ser Gln Asn Val Gly Ser Asn Val Val
  1               5                  10

<210> SEQ ID NO 13
<211> LENGTH: 7
<212> TYPE: PRT
```

<213> ORGANISM: Mus musculus

<400> SEQUENCE: 13

Ser Ala Ser Ser Arg Phe Ser
1               5

<210> SEQ ID NO 14
<211> LENGTH: 9
<212> TYPE: PRT
<213> ORGANISM: Mus musculus

<400> SEQUENCE: 14

Gln Gln Tyr Asn Thr Tyr Pro Leu Ala
1               5

<210> SEQ ID NO 15
<211> LENGTH: 119
<212> TYPE: PRT
<213> ORGANISM: Mus musculus

<400> SEQUENCE: 15

Asp Val Gln Leu Gln Glu Ser Gly Pro Gly Leu Val Lys Pro Ser Gln
1               5                   10                  15

Ser Leu Ser Val Thr Cys Thr Val Thr Gly Tyr Ser Ile Thr Asn Ala
            20                  25                  30

Tyr Tyr Trp Asn Trp Ile Arg His Phe Pro Gly Asn Lys Leu Glu Trp
        35                  40                  45

Leu Gly Tyr Ile His Ser Ser Gly Asp Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Pro Tyr Tyr Ser Asn Tyr Phe Pro Tyr Trp Gly Gln Gly
            100                 105                 110

Thr Leu Val Thr Val Ser Ala
        115

<210> SEQ ID NO 16
<211> LENGTH: 6
<212> TYPE: PRT
<213> ORGANISM: Mus musculus

<400> SEQUENCE: 16

Asn Ala Tyr Tyr Trp Asn
1               5

<210> SEQ ID NO 17
<211> LENGTH: 16
<212> TYPE: PRT
<213> ORGANISM: Mus musculus

<400> SEQUENCE: 17

Tyr Ile His Ser Ser Gly Asp Thr Asn Tyr Asn Pro Ser Leu Lys Ser
1               5                   10                  15

<210> SEQ ID NO 18
<211> LENGTH: 10
<212> TYPE: PRT
<213> ORGANISM: Mus musculus

<400> SEQUENCE: 18

Ser Pro Tyr Tyr Ser Asn Tyr Phe Pro Tyr
1               5                   10

<210> SEQ ID NO 19
<211> LENGTH: 214
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: subject to potential ambiguity due to the
      position of primer regions in the sequence determination

<400> SEQUENCE: 19

Asp Ile Leu Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Tyr
            20                  25                  30

Val Val Trp Tyr Gln Gln Lys Pro Gly Gln Ser Pro Lys Pro Leu Ile
        35                  40                  45

Tyr Ser Ala Ser Ser Arg Phe Ser Gly Val Pro Asp Arg Phe Thr Gly
    50                  55                  60

Thr Gly Ser Gly Thr Asp Phe Thr Leu Thr Ile Asn Asn Val Gln Ser
65                  70                  75                  80

Glu Asp Leu Ala Glu Tyr Phe Cys Gln Gln Tyr His Asn Ser Pro Leu
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 20
<211> LENGTH: 207
<212> TYPE: PRT
<213> ORGANISM: Mus musculus

<400> SEQUENCE: 20

Gln Lys Phe Met Ser Thr Ser Val Gly Asp Arg Val Ser Val Thr Cys
1               5                   10                  15

Lys Ala Ser Gln Asn Val Asp Thr Tyr Val Val Trp Tyr Gln Gln Lys
            20                  25                  30

Pro Gly Gln Ser Pro Lys Pro Leu Ile Tyr Ser Ala Ser Ser Arg Phe
        35                  40                  45

Ser Gly Val Pro Asp Arg Phe Thr Gly Thr Gly Ser Gly Thr Asp Phe
    50                  55                  60

-continued

```
Thr Leu Thr Ile Asn Asn Val Gln Ser Glu Asp Leu Ala Glu Tyr Phe
 65                  70                  75                  80

Cys Gln Gln Tyr His Asn Ser Pro Leu Thr Phe Gly Gly Gly Thr Lys
                 85                  90                  95

Leu Glu Ile Lys Arg Ala Asp Ala Ala Pro Thr Val Ser Ile Phe Pro
            100                 105                 110

Pro Ser Ser Glu Gln Leu Thr Ser Gly Gly Ala Ser Val Val Cys Phe
        115                 120                 125

Leu Asn Asn Phe Tyr Pro Lys Asp Ile Asn Val Lys Trp Lys Ile Asp
    130                 135                 140

Gly Ser Glu Arg Gln Asn Gly Val Leu Asn Ser Trp Thr Asp Gln Asp
145                 150                 155                 160

Ser Lys Asp Ser Thr Tyr Ser Met Ser Ser Thr Leu Thr Leu Thr Lys
                165                 170                 175

Asp Glu Tyr Glu Arg His Asn Ser Tyr Thr Cys Glu Ala Thr His Lys
            180                 185                 190

Thr Ser Thr Ser Pro Ile Val Lys Ser Phe Asn Arg Asn Glu Cys
        195                 200                 205
```

<210> SEQ ID NO 21
<211> LENGTH: 11
<212> TYPE: PRT
<213> ORGANISM: Mus musculus

<400> SEQUENCE: 21

```
Lys Ala Ser Gln Asn Val Asp Thr Tyr Val Val
1               5                   10
```

<210> SEQ ID NO 22
<211> LENGTH: 7
<212> TYPE: PRT
<213> ORGANISM: Mus musculus

<400> SEQUENCE: 22

```
Ser Ala Ser Ser Arg Phe Ser
1               5
```

<210> SEQ ID NO 23
<211> LENGTH: 9
<212> TYPE: PRT
<213> ORGANISM: Mus musculus

<400> SEQUENCE: 23

```
Gln Gln Tyr His Asn Ser Pro Leu Thr
1               5
```

<210> SEQ ID NO 24
<211> LENGTH: 221
<212> TYPE: PRT
<213> ORGANISM: Mus musculus
<220> FEATURE:
<221> NAME/KEY: MISC_FEATURE
<222> LOCATION: (1)..(8)
<223> OTHER INFORMATION: subject to potential ambiguity due to the
      position of primer regions in the sequence determination

<400> SEQUENCE: 24

```
Gln Val His Leu Gln Gln Ser Gly Pro Glu Leu Lys Lys Pro Gly Glu
1               5                   10                  15

Thr Val Lys Ile Ser Cys Lys Ala Ser Gly Tyr Ile Phe Ile Asp Tyr
            20                  25                  30
```

```
Gly Met His Trp Val Lys Gln Ala Pro Gly Lys Gly Leu Lys Trp Met
         35                  40                  45

Gly Ser Ile Asn Thr Lys Ser Gly Val Ser Thr Tyr Ala Ala Glu Phe
 50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                 85                  90                  95

Ala Arg Pro Pro Tyr Tyr Ser Gln Tyr Gly Ser Tyr Trp Gly Gln Gly
             100                 105                 110

Thr Leu Val Thr Val Ser Ala Ala Lys Thr Thr Pro Pro Ser Val Tyr
         115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys
    210                 215                 220

<210> SEQ ID NO 25
<211> LENGTH: 213
<212> TYPE: PRT
<213> ORGANISM: Mus musculus

<400> SEQUENCE: 25

Pro Glu Leu Lys Lys Pro Gly Glu Thr Val Lys Ile Ser Cys Lys Ala
 1               5                  10                  15

Ser Gly Tyr Ile Phe Ile Asp Tyr Gly Met His Trp Val Lys Gln Ala
             20                  25                  30

Pro Gly Lys Gly Leu Lys Trp Met Gly Ser Ile Asn Thr Lys Ser Gly
         35                  40                  45

Val Ser Thr Tyr Ala Ala Glu Phe Lys Gly Arg Phe Ala Phe Ser Leu
 50                  55                  60

Glu Thr Ser Ala Ser Thr Ala Tyr Leu Gln Ile Asn Asn Leu Lys Asn
 65                  70                  75                  80

Glu Asp Thr Ala Thr Tyr Phe Cys Ala Arg Pro Pro Tyr Tyr Ser Gln
                 85                  90                  95

Tyr Gly Ser Tyr Trp Gly Gln Gly Thr Leu Val Thr Val Ser Ala Ala
             100                 105                 110

Lys Thr Thr Pro Pro Ser Val Tyr Pro Leu Ala Pro Gly Ser Ala Ala
         115                 120                 125

Gln Thr Asn Ser Met Val Thr Leu Gly Cys Leu Val Lys Gly Tyr Phe
130                 135                 140

Pro Glu Pro Val Thr Val Thr Trp Asn Ser Gly Ser Leu Ser Ser Gly
145                 150                 155                 160

Val His Thr Phe Pro Ala Val Leu Gln Ser Asp Leu Tyr Thr Leu Ser
                165                 170                 175

Ser Ser Val Thr Val Pro Ser Ser Thr Trp Pro Ser Glu Thr Val Thr
            180                 185                 190
```

```
Cys Asn Val Ala His Pro Ala Ser Ser Thr Lys Val Asp Lys Lys Ile
            195                 200                 205
Val Pro Arg Asp Cys
    210

<210> SEQ ID NO 26
<211> LENGTH: 5
<212> TYPE: PRT
<213> ORGANISM: Mus musculus

<400> SEQUENCE: 26

Asp Tyr Gly Met His
1               5

<210> SEQ ID NO 27
<211> LENGTH: 17
<212> TYPE: PRT
<213> ORGANISM: Mus musculus

<400> SEQUENCE: 27

Ser Ile Asn Thr Lys Ser Gly Val Ser Thr Tyr Ala Ala Glu Phe Lys
1               5                   10                  15
Gly

<210> SEQ ID NO 28
<211> LENGTH: 10
<212> TYPE: PRT
<213> ORGANISM: Mus musculus

<400> SEQUENCE: 28

Pro Pro Tyr Tyr Ser Gln Tyr Gly Ser Tyr
1               5                   10

<210> SEQ ID NO 29
<211> LENGTH: 1479
<212> TYPE: PRT
<213> ORGANISM: Homo sapiens

<400> SEQUENCE: 29

Met Gly Pro Gly Arg Pro Ala Pro Ala Pro Trp Pro Arg His Leu Leu
1               5                   10                  15
Arg Cys Val Leu Leu Leu Gly Cys Leu His Leu Gly Arg Pro Gly Ala
                20                  25                  30
Pro Gly Asp Ala Ala Leu Pro Glu Pro Asn Val Phe Leu Ile Phe Ser
            35                  40                  45
His Gly Leu Gln Gly Cys Leu Glu Ala Gln Gly Gly Gln Val Arg Val
    50                  55                  60
Thr Pro Ala Cys Asn Thr Ser Leu Pro Ala Gln Arg Trp Lys Trp Val
65                  70                  75                  80
Ser Arg Asn Arg Leu Phe Asn Leu Gly Thr Met Gln Cys Leu Gly Thr
                85                  90                  95
Gly Trp Pro Gly Thr Asn Thr Thr Ala Ser Leu Gly Met Tyr Glu Cys
            100                 105                 110
Asp Arg Glu Ala Leu Asn Leu Arg Trp His Cys Arg Thr Leu Gly Asp
            115                 120                 125
Gln Leu Ser Leu Leu Gly Ala Arg Thr Ser Asn Ile Ser Lys Pro
        130                 135                 140
Gly Thr Leu Glu Arg Gly Asp Gln Thr Arg Ser Gly Gln Trp Arg Ile
145                 150                 155                 160
```

```
Tyr Gly Ser Glu Glu Asp Leu Cys Ala Leu Pro Tyr His Glu Val Tyr
            165                 170                 175

Thr Ile Gln Gly Asn Ser His Gly Lys Pro Cys Thr Ile Pro Phe Lys
            180                 185                 190

Tyr Asp Asn Gln Trp Phe His Gly Cys Thr Ser Thr Gly Arg Glu Asp
            195                 200                 205

Gly His Leu Trp Cys Ala Thr Thr Gln Asp Tyr Gly Lys Asp Glu Arg
            210                 215                 220

Trp Gly Phe Cys Pro Ile Lys Ser Asn Asp Cys Glu Thr Phe Trp Asp
225                 230                 235                 240

Lys Asp Gln Leu Thr Asp Ser Cys Tyr Gln Phe Asn Phe Gln Ser Thr
            245                 250                 255

Leu Ser Trp Arg Glu Ala Trp Ala Ser Cys Glu Gln Gln Gly Ala Asp
            260                 265                 270

Leu Leu Ser Ile Thr Glu Ile His Glu Gln Thr Tyr Ile Asn Gly Leu
            275                 280                 285

Leu Thr Gly Tyr Ser Ser Thr Leu Trp Ile Gly Leu Asn Asp Leu Asp
            290                 295                 300

Thr Ser Gly Gly Trp Gln Trp Ser Asp Asn Ser Pro Leu Lys Tyr Leu
305                 310                 315                 320

Asn Trp Glu Ser Asp Gln Pro Asp Asn Pro Ser Glu Glu Asn Cys Gly
            325                 330                 335

Val Ile Arg Thr Glu Ser Ser Gly Gly Trp Gln Asn Arg Asp Cys Ser
            340                 345                 350

Ile Ala Leu Pro Tyr Val Cys Lys Lys Pro Asn Ala Thr Ala Glu
            355                 360                 365

Pro Thr Pro Pro Asp Arg Trp Ala Asn Val Lys Val Glu Cys Glu Pro
            370                 375                 380

Ser Trp Gln Pro Phe Gln Gly His Cys Tyr Arg Leu Gln Ala Glu Lys
385                 390                 395                 400

Arg Ser Trp Gln Glu Ser Lys Lys Ala Cys Leu Arg Gly Gly Gly Asp
            405                 410                 415

Leu Val Ser Ile His Ser Met Ala Glu Leu Glu Phe Ile Thr Lys Gln
            420                 425                 430

Ile Lys Gln Glu Val Glu Glu Leu Trp Ile Gly Leu Asn Asp Leu Lys
            435                 440                 445

Leu Gln Met Asn Phe Glu Trp Ser Asp Gly Ser Leu Val Ser Phe Thr
            450                 455                 460

His Trp His Pro Phe Glu Pro Asn Asn Phe Arg Asp Ser Leu Glu Asp
465                 470                 475                 480

Cys Val Thr Ile Trp Gly Pro Glu Gly Arg Trp Asn Asp Ser Pro Cys
            485                 490                 495

Asn Gln Ser Leu Pro Ser Ile Cys Lys Lys Ala Gly Gln Leu Ser Gln
            500                 505                 510

Gly Ala Ala Glu Glu Asp His Gly Cys Arg Lys Gly Trp Thr Trp His
            515                 520                 525

Ser Pro Ser Cys Tyr Trp Leu Gly Glu Asp Gln Val Thr Tyr Ser Glu
            530                 535                 540

Ala Arg Arg Leu Cys Thr Asp His Gly Ser Gln Leu Val Thr Ile Thr
545                 550                 555                 560

Asn Arg Phe Glu Gln Ala Phe Val Ser Ser Leu Ile Tyr Asn Trp Glu
            565                 570                 575
```

```
Gly Glu Tyr Phe Trp Thr Ala Leu Gln Asp Leu Asn Ser Thr Gly Ser
            580                 585                 590

Phe Phe Trp Leu Ser Gly Asp Glu Val Met Tyr Thr His Trp Asn Arg
        595                 600                 605

Asp Gln Pro Gly Tyr Ser Arg Gly Gly Cys Val Ala Leu Ala Thr Gly
        610                 615                 620

Ser Ala Met Gly Leu Trp Glu Val Lys Asn Cys Thr Ser Phe Arg Ala
625                 630                 635                 640

Arg Tyr Ile Cys Arg Gln Ser Leu Gly Thr Pro Val Thr Pro Glu Leu
                645                 650                 655

Pro Gly Pro Asp Pro Thr Pro Ser Leu Thr Gly Ser Cys Pro Gln Gly
            660                 665                 670

Trp Ala Ser Asp Thr Lys Leu Arg Tyr Cys Tyr Lys Val Phe Ser Ser
        675                 680                 685

Glu Arg Leu Gln Asp Lys Lys Ser Trp Val Gln Ala Gln Gly Ala Cys
        690                 695                 700

Gln Glu Leu Gly Ala Gln Leu Leu Ser Leu Ala Ser Tyr Glu Glu Glu
705                 710                 715                 720

His Phe Val Ala Asn Met Leu Asn Lys Ile Phe Gly Glu Ser Glu Pro
                725                 730                 735

Glu Ile His Glu Gln His Trp Phe Trp Ile Gly Leu Asn Arg Arg Asp
            740                 745                 750

Pro Arg Gly Gly Gln Ser Trp Arg Trp Ser Asp Gly Val Gly Phe Ser
        755                 760                 765

Tyr His Asn Phe Asp Arg Ser Arg His Asp Asp Asp Ile Arg Gly
        770                 775                 780

Cys Ala Val Leu Asp Leu Ala Ser Leu Gln Trp Val Ala Met Gln Cys
785                 790                 795                 800

Asp Thr Gln Leu Asp Trp Ile Cys Lys Ile Pro Arg Gly Thr Asp Val
                805                 810                 815

Arg Glu Pro Asp Asp Ser Pro Gln Gly Arg Arg Glu Trp Leu Arg Phe
            820                 825                 830

Gln Glu Ala Glu Tyr Lys Phe Phe Glu His His Ser Thr Trp Ala Gln
        835                 840                 845

Ala Gln Arg Ile Cys Thr Trp Phe Gln Ala Glu Leu Thr Ser Val His
850                 855                 860

Ser Gln Ala Glu Leu Asp Phe Leu Ser His Asn Leu Gln Lys Phe Ser
865                 870                 875                 880

Arg Ala Gln Glu Gln His Trp Trp Ile Gly Leu His Thr Ser Glu Ser
                885                 890                 895

Asp Gly Arg Phe Arg Trp Thr Asp Gly Ser Ile Ile Asn Phe Ile Ser
            900                 905                 910

Trp Ala Pro Gly Lys Pro Arg Pro Val Gly Lys Asp Lys Lys Cys Val
        915                 920                 925

Tyr Met Thr Ala Ser Arg Glu Asp Trp Gly Asp Gln Arg Cys Leu Thr
930                 935                 940

Ala Leu Pro Tyr Ile Cys Lys Arg Ser Asn Val Thr Lys Glu Thr Gln
945                 950                 955                 960

Pro Pro Asp Leu Pro Thr Thr Ala Leu Gly Gly Cys Pro Ser Asp Trp
                965                 970                 975

Ile Gln Phe Leu Asn Lys Cys Phe Gln Val Gln Gly Gln Glu Pro Gln
            980                 985                 990

Ser Arg Val Lys Trp Ser Glu Ala  Gln Phe Ser Cys Glu  Gln Gln Glu
```

```
            995                 1000                1005
Ala  Gln  Leu  Val  Thr  Ile  Thr  Asn  Pro  Leu  Glu  Gln  Ala  Phe  Ile
         1010                 1015                1020

Thr  Ala  Ser  Leu  Pro  Asn  Val  Thr  Phe  Asp  Leu  Trp  Ile  Gly  Leu
         1025                 1030                1035

His  Ala  Ser  Gln  Arg  Asp  Phe  Gln  Trp  Val  Glu  Gln  Glu  Pro  Leu
         1040                 1045                1050

Met  Tyr  Ala  Asn  Trp  Ala  Pro  Gly  Glu  Pro  Ser  Gly  Pro  Ser  Pro
         1055                 1060                1065

Ala  Pro  Ser  Gly  Asn  Lys  Pro  Thr  Ser  Cys  Ala  Val  Val  Leu  His
         1070                 1075                1080

Ser  Pro  Ser  Ala  His  Phe  Thr  Gly  Arg  Trp  Asp  Asp  Arg  Ser  Cys
         1085                 1090                1095

Thr  Glu  Glu  Thr  His  Gly  Phe  Ile  Cys  Gln  Lys  Gly  Thr  Asp  Pro
         1100                 1105                1110

Ser  Leu  Ser  Pro  Ser  Pro  Ala  Ala  Leu  Pro  Pro  Ala  Pro  Gly  Thr
         1115                 1120                1125

Glu  Leu  Ser  Tyr  Leu  Asn  Gly  Thr  Phe  Arg  Leu  Leu  Gln  Lys  Pro
         1130                 1135                1140

Leu  Arg  Trp  His  Asp  Ala  Leu  Leu  Leu  Cys  Glu  Ser  His  Asn  Ala
         1145                 1150                1155

Ser  Leu  Ala  Tyr  Val  Pro  Asp  Pro  Tyr  Thr  Gln  Ala  Phe  Leu  Thr
         1160                 1165                1170

Gln  Ala  Ala  Arg  Gly  Leu  Arg  Thr  Pro  Leu  Trp  Ile  Gly  Leu  Ala
         1175                 1180                1185

Gly  Glu  Glu  Gly  Ser  Arg  Arg  Tyr  Ser  Trp  Val  Ser  Glu  Glu  Pro
         1190                 1195                1200

Leu  Asn  Tyr  Val  Gly  Trp  Gln  Asp  Gly  Glu  Pro  Gln  Gln  Pro  Gly
         1205                 1210                1215

Gly  Cys  Thr  Tyr  Val  Asp  Val  Asp  Gly  Ala  Trp  Arg  Thr  Thr  Ser
         1220                 1225                1230

Cys  Asp  Thr  Lys  Leu  Gln  Gly  Ala  Val  Cys  Gly  Val  Ser  Ser  Gly
         1235                 1240                1245

Pro  Pro  Pro  Pro  Arg  Arg  Ile  Ser  Tyr  His  Gly  Ser  Cys  Pro  Gln
         1250                 1255                1260

Gly  Leu  Ala  Asp  Ser  Ala  Trp  Ile  Pro  Phe  Arg  Glu  His  Cys  Tyr
         1265                 1270                1275

Ser  Phe  His  Met  Glu  Leu  Leu  Leu  Gly  His  Lys  Glu  Ala  Arg  Gln
         1280                 1285                1290

Arg  Cys  Gln  Arg  Ala  Gly  Gly  Ala  Val  Leu  Ser  Ile  Leu  Asp  Glu
         1295                 1300                1305

Met  Glu  Asn  Val  Phe  Val  Trp  Glu  His  Leu  Gln  Ser  Tyr  Glu  Gly
         1310                 1315                1320

Gln  Ser  Arg  Gly  Ala  Trp  Leu  Gly  Met  Asn  Phe  Asn  Pro  Lys  Gly
         1325                 1330                1335

Gly  Thr  Leu  Val  Trp  Gln  Asp  Asn  Thr  Ala  Val  Asn  Tyr  Ser  Asn
         1340                 1345                1350

Trp  Gly  Pro  Pro  Gly  Leu  Gly  Pro  Ser  Met  Leu  Ser  His  Asn  Ser
         1355                 1360                1365

Cys  Tyr  Trp  Ile  Gln  Ser  Asn  Ser  Gly  Leu  Trp  Arg  Pro  Gly  Ala
         1370                 1375                1380

Cys  Thr  Asn  Ile  Thr  Met  Gly  Val  Val  Cys  Lys  Leu  Pro  Arg  Ala
         1385                 1390                1395
```

Glu Gln Ser Ser Phe Ser Pro Ser Ala Leu Pro Glu Asn Pro Ala
    1400                1405                1410

Ala Leu Val Val Val Leu Met Ala Val Leu Leu Leu Ala Leu
    1415                1420                1425

Leu Thr Ala Ala Leu Ile Leu Tyr Arg Arg Gln Ser Ile Glu
    1430                1435                1440

Arg Gly Ala Phe Glu Gly Ala Arg Tyr Ser Arg Ser Ser Ser Ser
    1445                1450                1455

Pro Thr Glu Ala Thr Glu Lys Asn Ile Leu Val Ser Asp Met Glu
    1460                1465                1470

Met Asn Glu Gln Gln Glu
    1475

<210> SEQ ID NO 30
<211> LENGTH: 116
<212> TYPE: PRT
<213> ORGANISM: Homo sapiens

<400> SEQUENCE: 30

Ile Phe Ser His Gly Leu Gln Gly Cys Leu Glu Ala Gln Gly Gln
1               5                   10                  15

Val Arg Val Thr Pro Ala Cys Asn Thr Ser Leu Pro Ala Gln Arg Trp
                20                  25                  30

Lys Trp Val Ser Arg Asn Arg Leu Phe Asn Leu Gly Thr Met Gln Cys
            35                  40                  45

Leu Gly Thr Gly Trp Pro Gly Thr Asn Thr Thr Ala Ser Leu Gly Met
    50                  55                  60

Tyr Glu Cys Asp Arg Glu Ala Leu Asn Leu Arg Trp His Cys Arg Thr
65                  70                  75                  80

Leu Gly Asp Gln Leu Ser Leu Leu Gly Ala Arg Thr Ser Asn Ile
                85                  90                  95

Ser Lys Pro Gly Thr Leu Glu Arg Gly Asp Thr Arg Ser Gly Gln
            100                 105                 110

Trp Arg Ile Tyr
        115

<210> SEQ ID NO 31
<211> LENGTH: 121
<212> TYPE: PRT
<213> ORGANISM: Homo sapiens

<400> SEQUENCE: 31

Pro Asn Val Phe Leu Ile Phe Ser His Gly Leu Gln Gly Cys Leu Glu
1               5                   10                  15

Ala Gln Gly Gly Gln Val Arg Val Thr Pro Ala Cys Asn Thr Ser Leu
                20                  25                  30

Pro Ala Gln Arg Trp Lys Trp Val Ser Arg Asn Arg Leu Phe Asn Leu
            35                  40                  45

Gly Thr Met Gln Cys Leu Gly Thr Gly Trp Pro Gly Thr Asn Thr Thr
    50                  55                  60

Ala Ser Leu Gly Met Tyr Glu Cys Asp Arg Glu Ala Leu Asn Leu Arg
65                  70                  75                  80

Trp His Cys Arg Thr Leu Gly Asp Gln Leu Ser Leu Leu Gly Ala
                85                  90                  95

Arg Thr Ser Asn Ile Ser Lys Pro Gly Thr Leu Glu Arg Gly Asp Gln
            100                 105                 110

-continued

Thr Arg Ser Gly Gln Trp Arg Ile Tyr
        115                 120

<210> SEQ ID NO 32
<211> LENGTH: 48
<212> TYPE: PRT
<213> ORGANISM: Homo sapiens

<400> SEQUENCE: 32

Asn Ser His Gly Lys Pro Cys Thr Ile Pro Phe Lys Tyr Asp Asn Gln
1               5                   10                  15

Trp Phe His Gly Cys Thr Ser Thr Gly Arg Glu Asp Gly His Leu Trp
            20                  25                  30

Cys Ala Thr Thr Gln Asp Tyr Gly Lys Asp Glu Arg Trp Gly Phe Cys
        35                  40                  45

<210> SEQ ID NO 33
<211> LENGTH: 49
<212> TYPE: PRT
<213> ORGANISM: Homo sapiens

<400> SEQUENCE: 33

Gly Asn Ser His Gly Lys Pro Cys Thr Ile Pro Phe Lys Tyr Asp Asn
1               5                   10                  15

Gln Trp Phe His Gly Cys Thr Ser Thr Gly Arg Glu Asp Gly His Leu
            20                  25                  30

Trp Cys Ala Thr Thr Gln Asp Tyr Gly Lys Asp Glu Arg Trp Gly Phe
        35                  40                  45

Cys

<210> SEQ ID NO 34
<211> LENGTH: 115
<212> TYPE: PRT
<213> ORGANISM: Homo sapiens

<400> SEQUENCE: 34

Ser Cys Tyr Gln Phe Asn Phe Gln Ser Thr Leu Ser Trp Arg Glu Ala
1               5                   10                  15

Trp Ala Ser Cys Glu Gln Gln Gly Ala Asp Leu Leu Ser Ile Thr Glu
            20                  25                  30

Ile His Glu Gln Thr Tyr Ile Asn Gly Leu Leu Thr Gly Tyr Ser Ser
        35                  40                  45

Thr Leu Trp Ile Gly Leu Asn Asp Leu Asp Thr Ser Gly Gly Trp Gln
    50                  55                  60

Trp Ser Asp Asn Ser Pro Leu Lys Tyr Leu Asn Trp Glu Ser Asp Gln
65                  70                  75                  80

Pro Asp Asn Pro Ser Glu Glu Asn Cys Gly Val Ile Arg Thr Glu Ser
                85                  90                  95

Ser Gly Gly Trp Gln Asn Arg Asp Cys Ser Ile Ala Leu Pro Tyr Val
            100                 105                 110

Cys Lys Lys
        115

<210> SEQ ID NO 35
<211> LENGTH: 126
<212> TYPE: PRT
<213> ORGANISM: Homo sapiens

<400> SEQUENCE: 35

```
Cys Glu Thr Phe Trp Asp Lys Asp Gln Leu Thr Asp Ser Cys Tyr Gln
1               5                   10                  15

Phe Asn Phe Gln Ser Thr Leu Ser Trp Arg Glu Ala Trp Ala Ser Cys
            20                  25                  30

Glu Gln Gln Gly Ala Asp Leu Leu Ser Ile Thr Glu Ile His Glu Gln
        35                  40                  45

Thr Tyr Ile Asn Gly Leu Leu Thr Gly Tyr Ser Ser Thr Leu Trp Ile
    50                  55                  60

Gly Leu Asn Asp Leu Asp Thr Ser Gly Gly Trp Gln Trp Ser Asp Asn
65                  70                  75                  80

Ser Pro Leu Lys Tyr Leu Asn Trp Glu Ser Asp Gln Pro Asp Asn Pro
                85                  90                  95

Ser Glu Glu Asn Cys Gly Val Ile Arg Thr Glu Ser Ser Gly Gly Trp
            100                 105                 110

Gln Asn Arg Asp Cys Ser Ile Ala Leu Pro Tyr Val Cys Lys
        115                 120                 125
```

<210> SEQ ID NO 36
<211> LENGTH: 316
<212> TYPE: PRT
<213> ORGANISM: Homo sapiens

<400> SEQUENCE: 36

```
Ile Phe Ser His Gly Leu Gln Gly Cys Leu Glu Ala Gln Gly Gly Gln
1               5                   10                  15

Val Arg Val Thr Pro Ala Cys Asn Thr Ser Leu Pro Ala Gln Arg Trp
            20                  25                  30

Lys Trp Val Ser Arg Asn Arg Leu Phe Asn Leu Gly Thr Met Gln Cys
        35                  40                  45

Leu Gly Thr Gly Trp Pro Gly Thr Asn Thr Thr Ala Ser Leu Gly Met
    50                  55                  60

Tyr Glu Cys Asp Arg Glu Ala Leu Asn Leu Arg Trp His Cys Arg Thr
65                  70                  75                  80

Leu Gly Asp Gln Leu Ser Leu Leu Gly Ala Arg Thr Ser Asn Ile
                85                  90                  95

Ser Lys Pro Gly Thr Leu Glu Arg Gly Asp Gln Thr Arg Ser Gly Gln
            100                 105                 110

Trp Arg Ile Tyr Gly Ser Glu Asp Leu Cys Ala Leu Pro Tyr His
        115                 120                 125

Glu Val Tyr Thr Ile Gln Gly Asn Ser His Gly Lys Pro Cys Thr Ile
    130                 135                 140

Pro Phe Lys Tyr Asp Asn Gln Trp Phe His Gly Cys Thr Ser Thr Gly
145                 150                 155                 160

Arg Glu Asp Gly His Leu Trp Cys Ala Thr Thr Gln Asp Tyr Gly Lys
                165                 170                 175

Asp Glu Arg Trp Gly Phe Cys Pro Ile Lys Ser Asn Asp Cys Glu Thr
            180                 185                 190

Phe Trp Asp Lys Asp Gln Leu Thr Asp Ser Cys Tyr Gln Phe Asn Phe
        195                 200                 205

Gln Ser Thr Leu Ser Trp Arg Glu Ala Trp Ala Ser Cys Glu Gln Gln
    210                 215                 220

Gly Ala Asp Leu Leu Ser Ile Thr Glu Ile His Glu Gln Thr Tyr Ile
225                 230                 235                 240

Asn Gly Leu Leu Thr Gly Tyr Ser Ser Thr Leu Trp Ile Gly Leu Asn
```

-continued

```
                245                 250                 255
Asp Leu Asp Thr Ser Gly Gly Trp Gln Trp Ser Asp Asn Ser Pro Leu
            260                 265                 270

Lys Tyr Leu Asn Trp Glu Ser Asp Gln Pro Asp Asn Pro Ser Glu Glu
        275                 280                 285

Asn Cys Gly Val Ile Arg Thr Glu Ser Ser Gly Gly Trp Gln Asn Arg
    290                 295                 300

Asp Cys Ser Ile Ala Leu Pro Tyr Val Cys Lys Lys
305                 310                 315

<210> SEQ ID NO 37
<211> LENGTH: 320
<212> TYPE: PRT
<213> ORGANISM: Homo sapiens

<400> SEQUENCE: 37

Pro Asn Val Phe Leu Ile Phe Ser His Gly Leu Gln Gly Cys Leu Glu
1               5                   10                  15

Ala Gln Gly Gly Gln Val Arg Val Thr Pro Ala Cys Asn Thr Ser Leu
            20                  25                  30

Pro Ala Gln Arg Trp Lys Trp Val Ser Arg Asn Arg Leu Phe Asn Leu
        35                  40                  45

Gly Thr Met Gln Cys Leu Gly Thr Gly Trp Pro Gly Thr Asn Thr Thr
    50                  55                  60

Ala Ser Leu Gly Met Tyr Glu Cys Asp Arg Glu Ala Leu Asn Leu Arg
65                  70                  75                  80

Trp His Cys Arg Thr Leu Gly Asp Gln Leu Ser Leu Leu Gly Ala
                85                  90                  95

Arg Thr Ser Asn Ile Ser Lys Pro Gly Thr Leu Glu Arg Gly Asp Gln
            100                 105                 110

Thr Arg Ser Gly Gln Trp Arg Ile Tyr Gly Ser Glu Glu Asp Leu Cys
        115                 120                 125

Ala Leu Pro Tyr His Glu Val Tyr Thr Ile Gln Gly Asn Ser His Gly
    130                 135                 140

Lys Pro Cys Thr Ile Pro Phe Lys Tyr Asp Asn Gln Trp Phe His Gly
145                 150                 155                 160

Cys Thr Ser Thr Gly Arg Glu Asp Gly His Leu Trp Cys Ala Thr Thr
                165                 170                 175

Gln Asp Tyr Gly Lys Asp Glu Arg Trp Gly Phe Cys Pro Ile Lys Ser
            180                 185                 190

Asn Asp Cys Glu Thr Phe Trp Asp Lys Asp Gln Leu Thr Asp Ser Cys
        195                 200                 205

Tyr Gln Phe Asn Phe Gln Ser Thr Leu Ser Trp Arg Glu Ala Trp Ala
    210                 215                 220

Ser Cys Glu Gln Gln Gly Ala Asp Leu Leu Ser Ile Thr Glu Ile His
225                 230                 235                 240

Glu Gln Thr Tyr Ile Asn Gly Leu Leu Thr Gly Tyr Ser Ser Thr Leu
                245                 250                 255

Trp Ile Gly Leu Asn Asp Leu Asp Thr Ser Gly Gly Trp Gln Trp Ser
            260                 265                 270

Asp Asn Ser Pro Leu Lys Tyr Leu Asn Trp Glu Ser Asp Gln Pro Asp
        275                 280                 285

Asn Pro Ser Glu Glu Asn Cys Gly Val Ile Arg Thr Glu Ser Ser Gly
    290                 295                 300
```

Gly Trp Gln Asn Arg Asp Cys Ser Ile Ala Leu Pro Tyr Val Cys Lys
305                 310                 315                 320

<210> SEQ ID NO 38
<211> LENGTH: 183
<212> TYPE: PRT
<213> ORGANISM: Homo sapiens

<400> SEQUENCE: 38

Ile Phe Ser His Gly Leu Gln Gly Cys Leu Glu Ala Gln Gly Gly Gln
1               5                   10                  15

Val Arg Val Thr Pro Ala Cys Asn Thr Ser Leu Pro Ala Gln Arg Trp
            20                  25                  30

Lys Trp Val Ser Arg Asn Arg Leu Phe Asn Leu Gly Thr Met Gln Cys
        35                  40                  45

Leu Gly Thr Gly Trp Pro Gly Thr Asn Thr Thr Ala Ser Leu Gly Met
50                  55                  60

Tyr Glu Cys Asp Arg Glu Ala Leu Asn Leu Arg Trp His Cys Arg Thr
65                  70                  75                  80

Leu Gly Asp Gln Leu Ser Leu Leu Gly Ala Arg Thr Ser Asn Ile
                85                  90                  95

Ser Lys Pro Gly Thr Leu Glu Arg Gly Asp Gln Thr Arg Ser Gly Gln
            100                 105                 110

Trp Arg Ile Tyr Gly Ser Glu Glu Asp Leu Cys Ala Leu Pro Tyr His
        115                 120                 125

Glu Val Tyr Thr Ile Gln Gly Asn Ser His Gly Lys Pro Cys Thr Ile
130                 135                 140

Pro Phe Lys Tyr Asp Asn Gln Trp Phe His Gly Cys Thr Ser Thr Gly
145                 150                 155                 160

Arg Glu Asp Gly His Leu Trp Cys Ala Thr Thr Gln Asp Tyr Gly Lys
                165                 170                 175

Asp Glu Arg Trp Gly Phe Cys
            180

<210> SEQ ID NO 39
<211> LENGTH: 188
<212> TYPE: PRT
<213> ORGANISM: Homo sapiens

<400> SEQUENCE: 39

Pro Asn Val Phe Leu Ile Phe Ser His Gly Leu Gln Gly Cys Leu Glu
1               5                   10                  15

Ala Gln Gly Gly Gln Val Arg Val Thr Pro Ala Cys Asn Thr Ser Leu
            20                  25                  30

Pro Ala Gln Arg Trp Lys Trp Val Ser Arg Asn Arg Leu Phe Asn Leu
        35                  40                  45

Gly Thr Met Gln Cys Leu Gly Thr Gly Trp Pro Gly Thr Asn Thr Thr
50                  55                  60

Ala Ser Leu Gly Met Tyr Glu Cys Asp Arg Glu Ala Leu Asn Leu Arg
65                  70                  75                  80

Trp His Cys Arg Thr Leu Gly Asp Gln Leu Ser Leu Leu Gly Ala
                85                  90                  95

Arg Thr Ser Asn Ile Ser Lys Pro Gly Thr Leu Glu Arg Gly Asp Gln
            100                 105                 110

Thr Arg Ser Gly Gln Trp Arg Ile Tyr Gly Ser Glu Glu Asp Leu Cys
        115                 120                 125

```
Ala Leu Pro Tyr His Glu Val Tyr Thr Ile Gln Gly Asn Ser His Gly
    130                 135                 140

Lys Pro Cys Thr Ile Pro Phe Lys Tyr Asp Asn Gln Trp Phe His Gly
145                 150                 155                 160

Cys Thr Ser Thr Gly Arg Glu Asp Gly His Leu Trp Cys Ala Thr Thr
                165                 170                 175

Gln Asp Tyr Gly Lys Asp Glu Arg Trp Gly Phe Cys
    180                 185

<210> SEQ ID NO 40
<211> LENGTH: 181
<212> TYPE: PRT
<213> ORGANISM: Homo sapiens

<400> SEQUENCE: 40

Asn Ser His Gly Lys Pro Cys Thr Ile Pro Phe Lys Tyr Asp Asn Gln
1               5                   10                  15

Trp Phe His Gly Cys Thr Ser Thr Gly Arg Glu Asp Gly His Leu Trp
            20                  25                  30

Cys Ala Thr Thr Gln Asp Tyr Gly Lys Asp Glu Arg Trp Gly Phe Cys
        35                  40                  45

Pro Ile Lys Ser Asn Asp Cys Glu Thr Phe Trp Asp Lys Asp Gln Leu
    50                  55                  60

Thr Asp Ser Cys Tyr Gln Phe Asn Phe Gln Ser Thr Leu Ser Trp Arg
65                  70                  75                  80

Glu Ala Trp Ala Ser Cys Glu Gln Gln Gly Ala Asp Leu Leu Ser Ile
                85                  90                  95

Thr Glu Ile His Glu Gln Thr Tyr Ile Asn Gly Leu Leu Thr Gly Tyr
            100                 105                 110

Ser Ser Thr Leu Trp Ile Gly Leu Asn Asp Leu Asp Thr Ser Gly Gly
        115                 120                 125

Trp Gln Trp Ser Asp Asn Ser Pro Leu Lys Tyr Leu Asn Trp Glu Ser
    130                 135                 140

Asp Gln Pro Asp Asn Pro Ser Glu Glu Asn Cys Gly Val Ile Arg Thr
145                 150                 155                 160

Glu Ser Ser Gly Gly Trp Gln Asn Arg Asp Cys Ser Ile Ala Leu Pro
                165                 170                 175

Tyr Val Cys Lys Lys
            180

<210> SEQ ID NO 41
<211> LENGTH: 181
<212> TYPE: PRT
<213> ORGANISM: Homo sapiens

<400> SEQUENCE: 41

Gly Asn Ser His Gly Lys Pro Cys Thr Ile Pro Phe Lys Tyr Asp Asn
1               5                   10                  15

Gln Trp Phe His Gly Cys Thr Ser Thr Gly Arg Glu Asp Gly His Leu
            20                  25                  30

Trp Cys Ala Thr Thr Gln Asp Tyr Gly Lys Asp Glu Arg Trp Gly Phe
        35                  40                  45

Cys Pro Ile Lys Ser Asn Asp Cys Glu Thr Phe Trp Asp Lys Asp Gln
    50                  55                  60

Leu Thr Asp Ser Cys Tyr Gln Phe Asn Phe Gln Ser Thr Leu Ser Trp
65                  70                  75                  80
```

-continued

```
Arg Glu Ala Trp Ala Ser Cys Glu Gln Gln Gly Ala Asp Leu Leu Ser
                85                  90                  95

Ile Thr Glu Ile His Glu Gln Thr Tyr Ile Asn Gly Leu Leu Thr Gly
            100                 105                 110

Tyr Ser Ser Thr Leu Trp Ile Gly Leu Asn Asp Leu Asp Thr Ser Gly
        115                 120                 125

Gly Trp Gln Trp Ser Asp Asn Ser Pro Leu Lys Tyr Leu Asn Trp Glu
130                 135                 140

Ser Asp Gln Pro Asp Asn Pro Ser Glu Glu Asn Cys Gly Val Ile Arg
145                 150                 155                 160

Thr Glu Ser Ser Gly Gly Trp Gln Asn Arg Asp Cys Ser Ile Ala Leu
                165                 170                 175

Pro Tyr Val Cys Lys
            180

<210> SEQ ID NO 42
<211> LENGTH: 8
<212> TYPE: PRT
<213> ORGANISM: Mus musculus

<400> SEQUENCE: 42

Gln Thr Ile Gly Thr Trp Leu Ala
1               5

<210> SEQ ID NO 43
<211> LENGTH: 11
<212> TYPE: PRT
<213> ORGANISM: Mus musculus

<400> SEQUENCE: 43

Leu Leu Ile Tyr Ala Ala Thr Thr Leu Thr Asp
1               5                   10

<210> SEQ ID NO 44
<211> LENGTH: 8
<212> TYPE: PRT
<213> ORGANISM: Mus musculus

<400> SEQUENCE: 44

Gln Glu Phe Phe Ser Thr Pro Phe
1               5

<210> SEQ ID NO 45
<211> LENGTH: 9
<212> TYPE: PRT
<213> ORGANISM: Mus musculus

<400> SEQUENCE: 45

Tyr Thr Phe Thr Ser Tyr Trp Met Asn
1               5

<210> SEQ ID NO 46
<211> LENGTH: 14
<212> TYPE: PRT
<213> ORGANISM: Mus musculus

<400> SEQUENCE: 46

Trp Ile Gly Met Ile His Pro Ser Asn Asp Glu Lys Arg Ile
1               5                   10

<210> SEQ ID NO 47
<211> LENGTH: 14
```

```
<212> TYPE: PRT
<213> ORGANISM: Mus musculus

<400> SEQUENCE: 47

Arg Gly Gly Gly Asp Tyr Val Gly Asp Tyr Ala Leu Asp Phe
1               5                   10

<210> SEQ ID NO 48
<211> LENGTH: 8
<212> TYPE: PRT
<213> ORGANISM: Mus musculus

<400> SEQUENCE: 48

Gln Asn Val Gly Ser Asn Val Val
1               5

<210> SEQ ID NO 49
<211> LENGTH: 11
<212> TYPE: PRT
<213> ORGANISM: Mus musculus

<400> SEQUENCE: 49

Ala Leu Ile Tyr Ser Ala Ser Ser Arg Phe Ser
1               5                   10

<210> SEQ ID NO 50
<211> LENGTH: 9
<212> TYPE: PRT
<213> ORGANISM: Mus musculus

<400> SEQUENCE: 50

Gln Gln Tyr Asn Thr Tyr Pro Leu Ala
1               5

<210> SEQ ID NO 51
<211> LENGTH: 10
<212> TYPE: PRT
<213> ORGANISM: Mus musculus

<400> SEQUENCE: 51

Tyr Ser Ile Thr Asn Ala Tyr Tyr Trp Asn
1               5                   10

<210> SEQ ID NO 52
<211> LENGTH: 13
<212> TYPE: PRT
<213> ORGANISM: Mus musculus

<400> SEQUENCE: 52

Trp Leu Gly Tyr Ile His Ser Ser Gly Asp Thr Asn Tyr
1               5                   10

<210> SEQ ID NO 53
<211> LENGTH: 11
<212> TYPE: PRT
<213> ORGANISM: Mus musculus

<400> SEQUENCE: 53

Arg Ser Pro Tyr Tyr Ser Asn Tyr Phe Pro Tyr
1               5                   10

<210> SEQ ID NO 54
<211> LENGTH: 8
<212> TYPE: PRT
<213> ORGANISM: Mus musculus
```

```
<400> SEQUENCE: 54

Gln Asn Val Asp Thr Tyr Val Val
1               5

<210> SEQ ID NO 55
<211> LENGTH: 11
<212> TYPE: PRT
<213> ORGANISM: Mus musculus

<400> SEQUENCE: 55

Pro Leu Ile Tyr Ser Ala Ser Ser Arg Phe Ser
1               5                   10

<210> SEQ ID NO 56
<211> LENGTH: 8
<212> TYPE: PRT
<213> ORGANISM: Mus musculus

<400> SEQUENCE: 56

Gln Gln Tyr His Asn Ser Pro Leu
1               5

<210> SEQ ID NO 57
<211> LENGTH: 9
<212> TYPE: PRT
<213> ORGANISM: Mus musculus

<400> SEQUENCE: 57

Tyr Ile Phe Ile Asp Tyr Gly Met His
1               5

<210> SEQ ID NO 58
<211> LENGTH: 14
<212> TYPE: PRT
<213> ORGANISM: Mus musculus

<400> SEQUENCE: 58

Trp Met Gly Ser Ile Asn Thr Lys Ser Gly Val Ser Thr Tyr
1               5                   10

<210> SEQ ID NO 59
<211> LENGTH: 11
<212> TYPE: PRT
<213> ORGANISM: Mus musculus

<400> SEQUENCE: 59

Arg Pro Pro Tyr Tyr Ser Gln Tyr Gly Ser Tyr
1               5                   10
```

ANTIBODY-DRUG CONJUGATES TARGETING UPARAP

CROSS-REFERENCE TO RELATED APPLICATIONS

This application is a divisional of U.S. application Ser. No. 16/074,961, filed Aug. 2, 2018, which is the National Stage of International Patent Application No. PCT/DK2017/050024, filed Feb. 3, 2017, which claims the benefit of Danish application number PA 2016 70063, filed Feb. 5, 2016 and Danish application number PA 2016 70834, filed Oct. 24, 2016, the disclosures of each of which are incorporated herein by reference in their entireties.

SEQUENCE LISTING

The instant application contains a Sequence Listing which has been submitted electronically in ASCII format and is hereby incorporated by reference in its entirety. The ASCII copy, created on Jan. 25, 2021, is named 105728.000064_SL and is 55,815 bytes in size.

FIELD OF INVENTION

The present invention relates to molecular conjugates targeting the receptor uPARAP, in particular antibody-drug conjugates (ADCs) directed against uPARAP and their use in delivery of active agents to cells and tissues expressing uPARAP. The invention further relates to the use of said ADCs in the treatment of diseases involving uPARAP expressing cells, such as certain cancers.

BACKGROUND

Urokinase-type Plasminogen Activator Receptor Associated Protein (uPARAP), also known as CD280, Endo180 and mannose receptor C type 2, is a member of the macrophage mannose receptor family of endocytic transmembrane glycoproteins. uPARAP is a membrane protein involved in matrix turnover during tissue remodelling, particularly the uptake and intracellular degradation of collagen.

The receptor uPARAP is upregulated in the tumour cells of specific cancers, including sarcomas and late-stage glioblastoma. Additionally, the receptor is most often upregulated in stromal cells surrounding solid tumours and some literature suggests a high expression of uPARAP in bone metastasis from prostate cancer (Caley et al., 2012, J. Pathol 5: 775-783). In healthy adult individuals, the receptor displays a restricted expression pattern (Melander et al., 2015, Int J Oncol 47: 1177-1188).

Antibody-drug conjugates (ADCs) are a new class of highly potent biopharmaceutical drug designed as a targeted therapy, in particular for the treatment of cancer. ADCs are complex molecules composed of an antibody (a whole mAb or an antibody fragment) linked, via a stable, chemical, linker that may possess labile bonds, to a biologically active drug or cytotoxic compound. By combining the unique targeting capabilities of antibodies with the cell-killing ability of cytotoxic drugs, antibody-drug conjugates allow sensitive discrimination between healthy and diseased tissue, based on expression of the antibody antigen. This means that, in contrast to traditional chemotherapeutic agents, antibody-drug conjugates actively target and attack cancer cells, so that healthy cells with little or no antigen expression are less severely affected. To date, three ADCs have received market approval and several ADCs are currently in clinical trials.

WO 2010/111198 discloses conjugates comprising an anti-uPARAP antibody and suggests use of such conjugates in the delivery of therapeutic agents to cells that express uPARAP.

Treatment methods currently exist for most cancer types. However, in most cases with unsatisfactory efficiency or with detrimental side effects due to the lack of specificity of the treatment. Thus, there is a need for more efficient treatments with increased specificity.

SUMMARY

The present invention provides antibody-drug conjugates (ADCs) based on anti-uPARAP antibodies capable of binding to the N-terminal region of the uPARAP receptor. The ADCs as described herein are capable of specifically targeting cells and tissues expressing uPARAP, and have excellent in vitro and in vivo efficacy with no registered side effects.

In particular, the present disclosure relates to an antibody-drug conjugate comprising:
  a. an antibody or antigen-binding fragment thereof capable of binding to:
    i. the amino acid sequence of SEQ ID NO: 36 or 37 (CysR-FN-II-CTLD-1 domains of uPARAP),
    ii. the amino acid sequence of SEQ ID NO: 38 or 39 (CysR-FN-II domains of uPARAP),
    iii. the amino acid sequence of SEQ ID NO: 40 or 41 (FN-II-CTLD-1 domains of uPARAP),
    iv. the amino acid sequence of SEQ ID NO: 30 or 31 (the cystein-rich domain (CysR) of uPARAP)
    v. the amino acid sequence of SEQ ID NO: 32 or 33 (the Fibronectin type II (FN-II) domain of uPARAP), and/or
    vi. the amino acid sequence of SEQ ID NO: 34 or 35 (the C-type lectin-like domain 1 (CTLD 1) of uPARAP),
  b. an active agent, and optionally
  c. a linker which links a) to b).

Furthermore, the present disclosure relates to the use of the ADC as defined above for the treatment of diseases and/or disorders involving expression of the uPARAP receptor.

DESCRIPTION OF DRAWINGS

FIG. 3: Cellular uptake of mAb 2h9, labeled with a fluorophore (AlexaFluor 647, AF647) using a method similar to the conjugation procedure described in the figure legend to FIG. 2 (partial reduction followed by reaction with a maleimide-derivatized AlexaFluor 647 reagent), in uPARAP-positive cell lines, measured by flow cytometry. MFI: Mean fluorescence intensity. Specificity ratio: Ratio of 2h9-AF647/aTNP-AF647 signals, with aTNP being a non-targeted control mAb. These numbers demonstrate a specific uptake of 2h9-AF647, and confirm that mAb 2h9 is taken up by uPARAP-positive cells following such a conjugation method.

FIG. 6: Cell cycle distribution analysis of four uPARAP-positive cell lines (U937, THP-1, HT1080 or KNS42) following a 3-day incubation in the presence of 1 μg/mL of uPARAP-directed ADC 2h9-vc-MMAE or control ADC aTNP-vc-MMAE, or 50 nM free MMAE toxin. Since MMAE is a tubulin inhibitor, a drug effect may lead to an increase in the fraction of cells in either the Sub-G1 phase (ultimately leading to apoptosis), or the G2-M phase (inhibition of genomic segregation following DNA replication). A dash indicates a cell count too low to register, due to widespread cell death and disintegration. It is seen that all four cell lines display specific sensitivity towards uPARAP-directed ADC 2h9-vc-MMAE (and free MMAE), evident from the shift in cell cycle distribution towards the Sub-G1 and G2/M phases in these samples.

Figure 1:
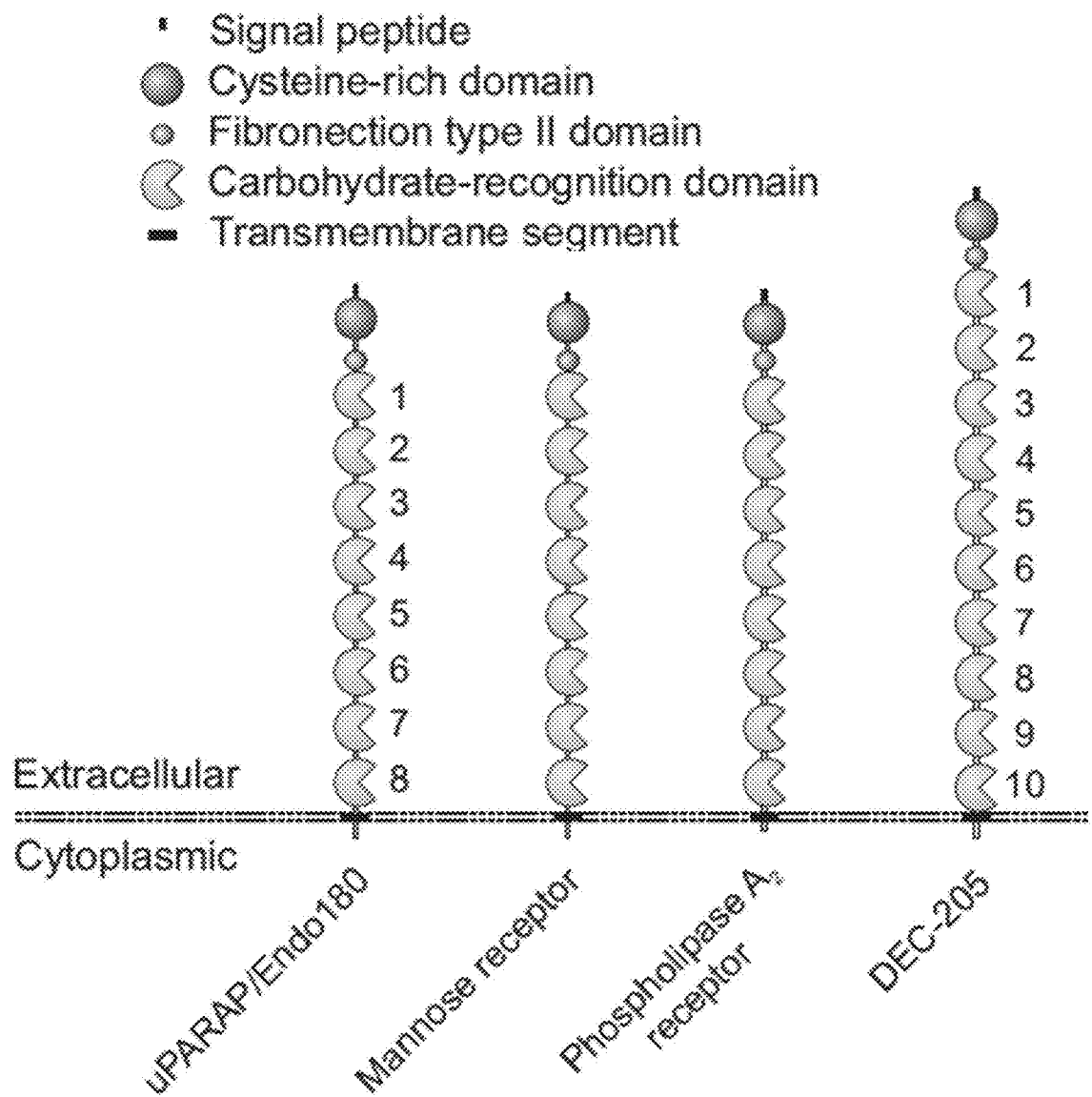
FIG. 1. Schematic representation of the four protein family members of the Mannose receptor family, including uPARAP. All of the proteins have the same over-all domain composition with an N-terminal signal peptide followed by a cysteine-rich domain, a fibronectin type II domain (FN-II domain), 8-10 C-type lectin-like domains (CTLDs), a transmembrane spanning region and a small cytoplasmic tail (Adapted from Melander et al., 2015 Int J Oncology 47: 1177-1188).
Figure 2:
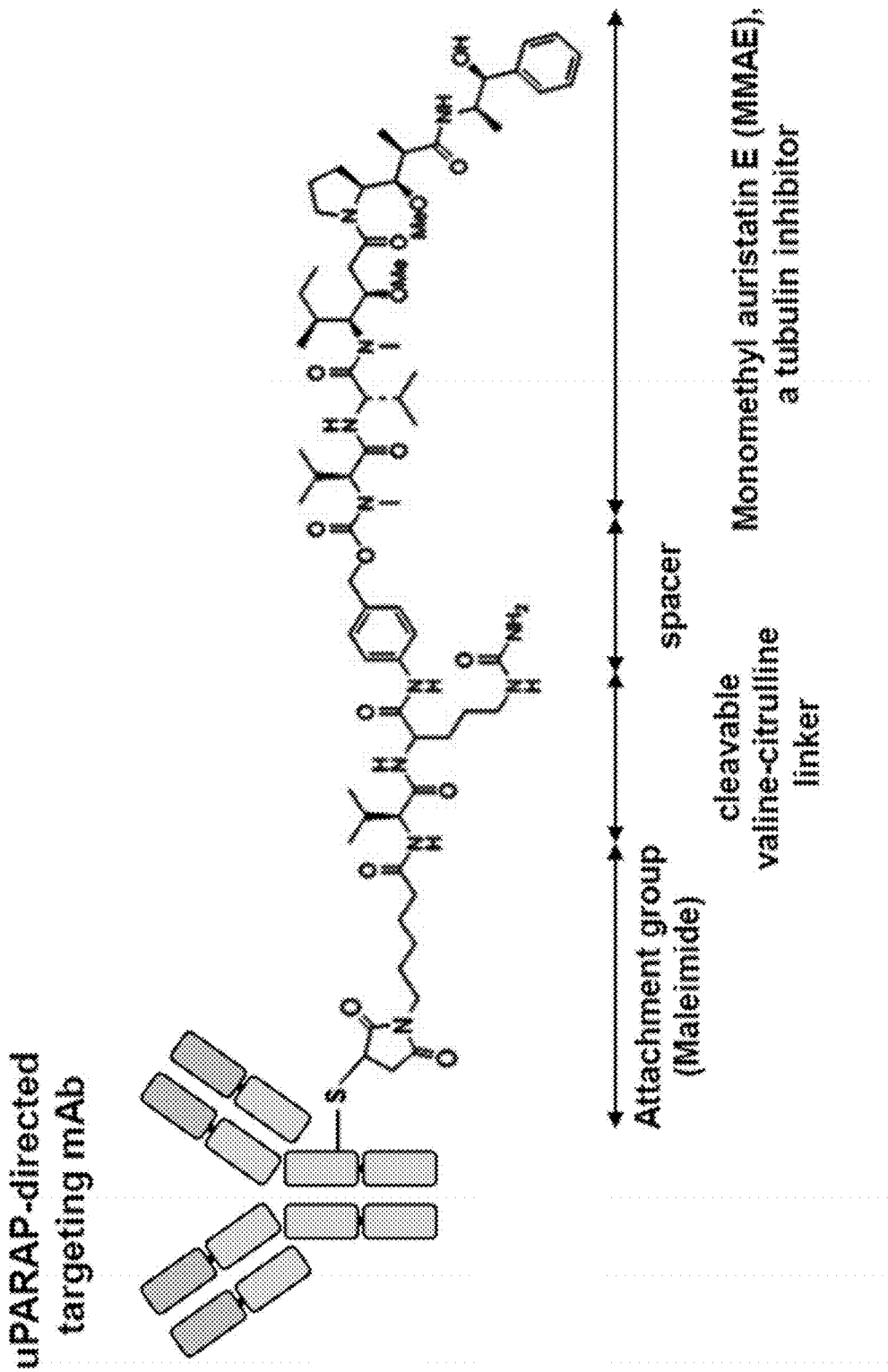
FIG. 2. Schematic illustration of an uPARAP-directed ADC, in the form of a targeting antibody, conjugated to a maleimidocaproyl-valine-citrulline-p-aminobenzoyloxycarbonyl-monomethyl auristatin E (MC-VC-PAB-MMAE) linker-toxin construct. The targeting antibody is specific against the receptor uPARAP, which is found to be highly expressed in certain cancer types. The linker-toxin construct is attached by maleimide chemistry to thiols of free cysteines or reduced interchain disulphide bridges (N=1-10 toxins per antibody). The valine-citrulline linker region with the peptide/amide bond to the spacer entity is a substrate for lysosomal proteases such as cathepsin B, but is sufficiently stable in the extracellular environment to ensure release of the conjugated drug only when taken up by cells expressing the target antigen. The conjugated drug is a highly potent tubulin inhibitor in the form of monomethyl auristatin E (MMAE). As a unit (mAb-vc-MMAE), this ADC construct ensures specific delivery of the drug component only to cells expressing the uPARAP antigen, as well as intracellular release of the conjugated drug in these cells.
Figure 4:
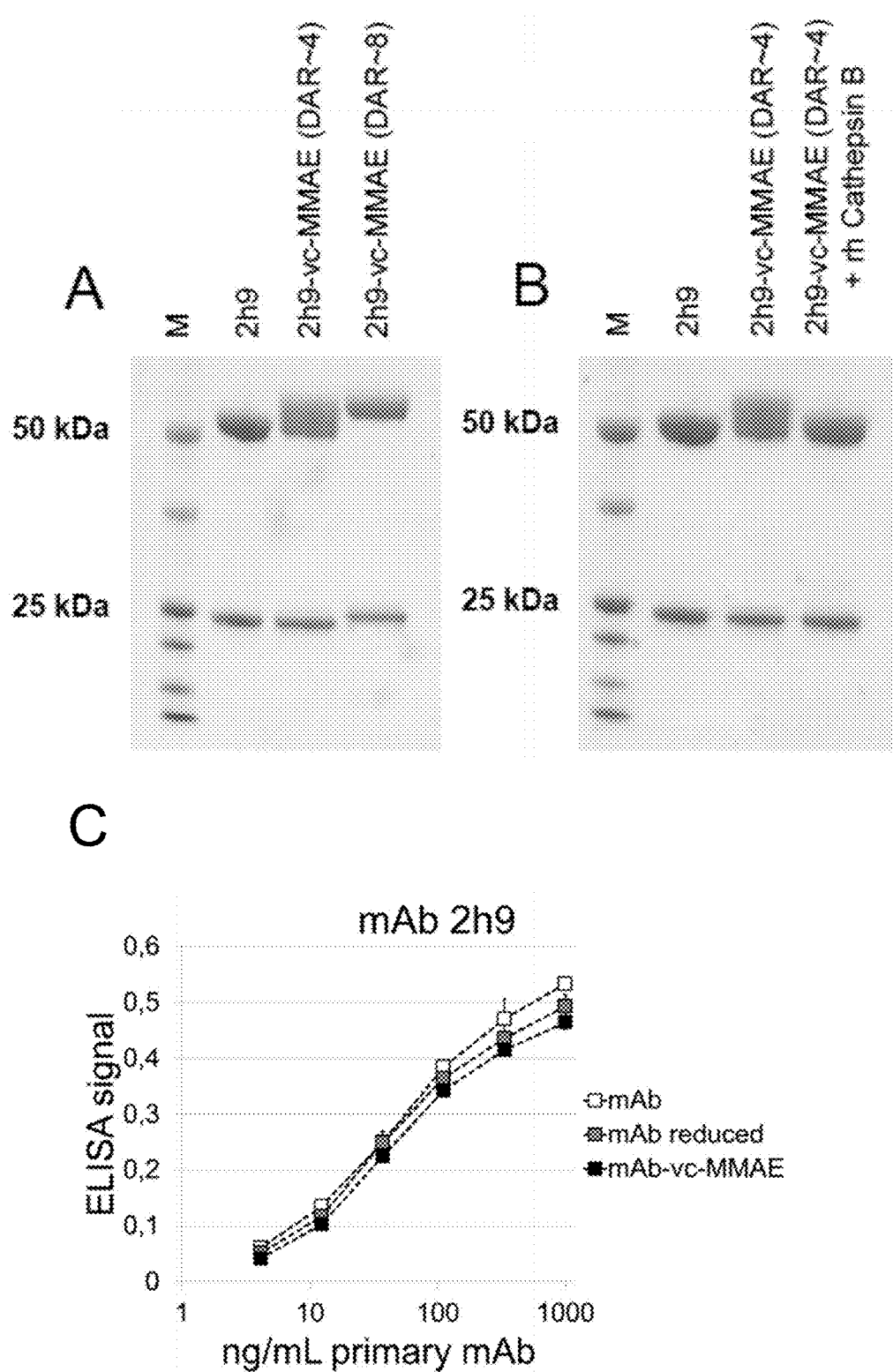
FIG. 4: A. Reducing SDS-PAGE of a targeting antibody (2h9), a mAb-vc-MMAE ADC with a moderate drug-to-antibody ratio (DAR) of ~4-5, and a mAb-vc-MMAE ADC with a DAR of ~8-10. It is seen that conjugated mAbs display reduced mobility in the gel, and that moderately conjugated ADC species are preferably conjugated via the mAb heavy chains, whereas the ADC with a higher DAR is conjugated via both the heavy- and the light chains. B. Reducing SDS-PAGE showing that incubation of ADCs with activated recombinant cathepsin B (+rh cathepsin B) reverts ADC gel mobility back to that of unmodified targeting antibody, and thus that the linker region is indeed cleavable by lysosomal proteases such as cathepsin B. C. ELISA analysis showing retained affinity of mAb 2h9 towards uPARAP following the reduction step of the conjugation procedure, as well as in ADC form. Altogether, these data show that ADC 2h9-vc-MMAE behaves as expected, in relation to gel mobility and affinity towards the target receptor following conjugation.
Figure 5:
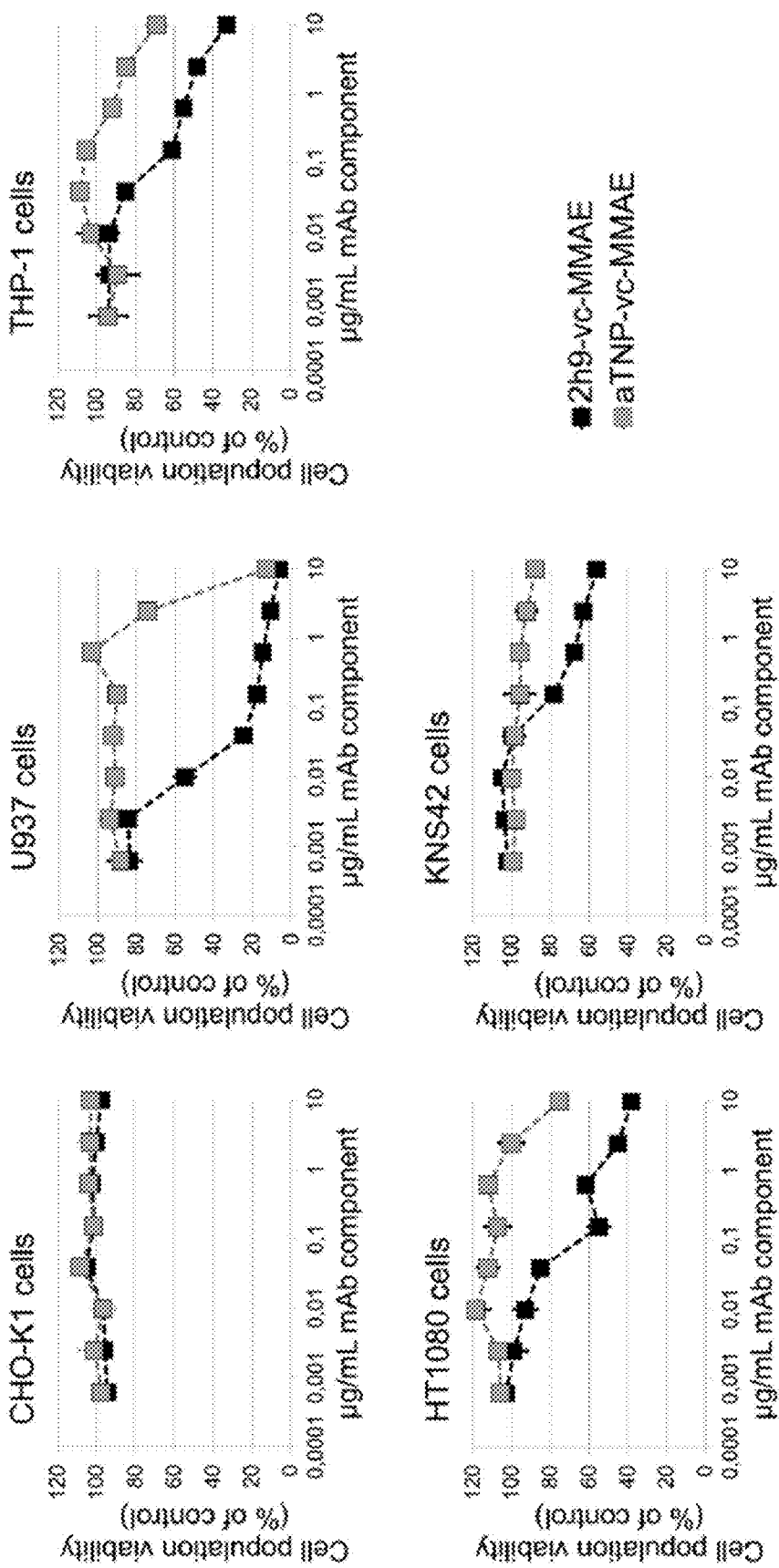
FIG. 5: In vitro cell viability assays, based on exposure to the ADCs in a dilution series. The dilution series starts at 10 μg/mL ADC (mAb component). followed by a series of 4-fold dilutions of the ADCs. Cells were incubated for 72 hours, before being analyzed by colorimetric viability assay. Here, the assay shows a specific reduction in overall viability following incubation with uPARAP-directed ADC 2h9-vc-MMAE, in comparison to a non-targeted ADC (aTNP-vc-MMAE), in four cell lines expressing the target receptor (U937, THP-1, HT1080 and KNS42 cells), whereas a receptor-negative cell line (CHO-K1) remains unaffected. This demonstrates a receptor-specific reduction in the viability of uPARAP-positive cell lines, following incubation with ADC 2h9-vc-MMAE.
Figure 7:
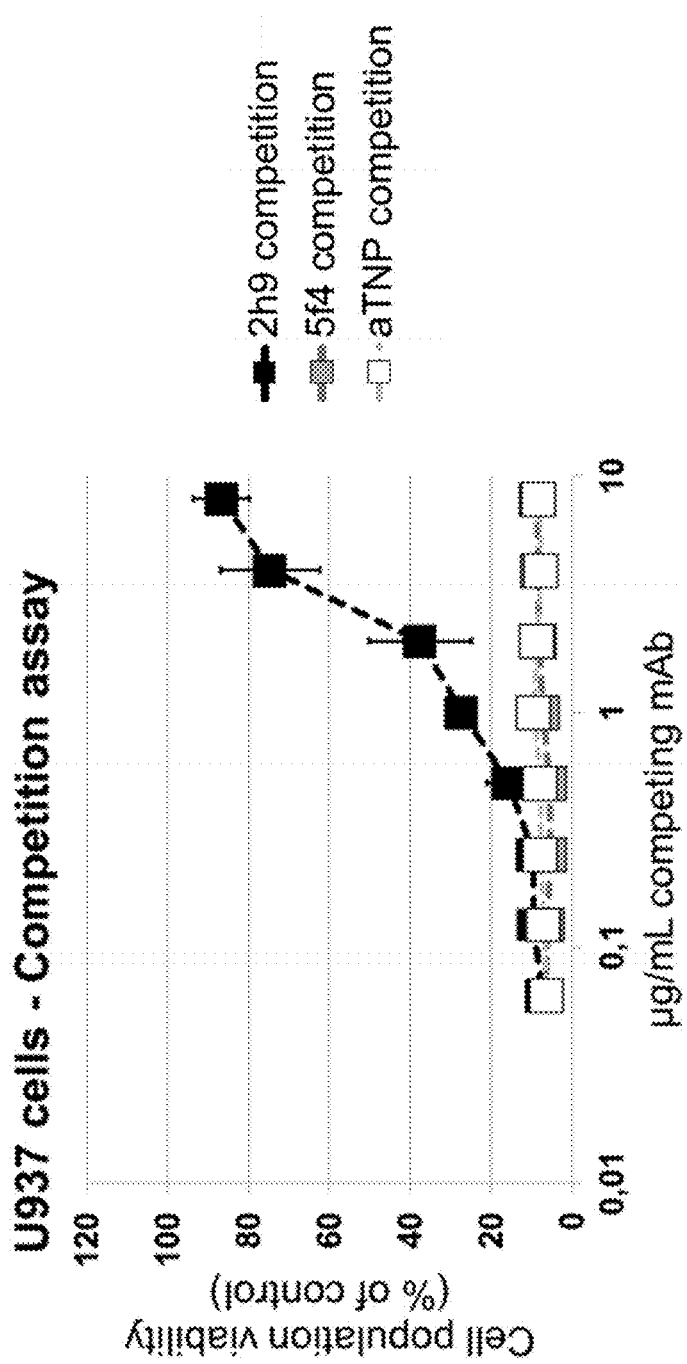
FIG. 7: Competition assay, showing U937 cells being incubated for 3 days in the presence of 1 μg/mL of uPARAP-directed ADC 2h9-vc-MMAE, in the simultaneous presence of different concentrations of unconjugated targeting antibody (2h9), another antibody targeting uPARAP (5f4), or the non-targeting control antibody (aTNP). It is seen that only a molar surplus (1+μg/mL competing mAb) of non-conjugated targeting antibody 2h9 can compete for the effect of the ADC, thereby rescuing cells from ADC mediated cell death. Thereby, the interaction between uPARAP and the targeting antibody 2h9 is shown to be crucial for the observed cytotoxic effect.
Figure 8:
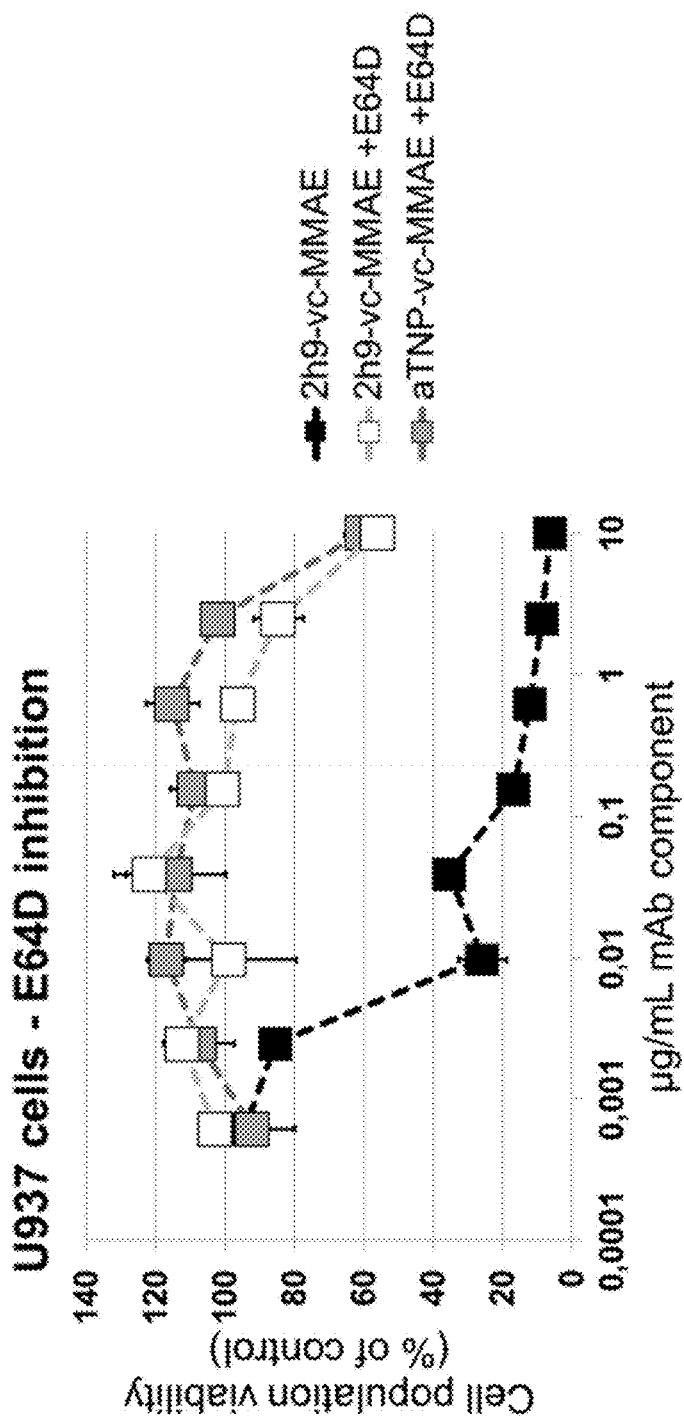
FIG. 8: It is shown that pre-incubating U937 cells in the presence of a broad-spectrum inhibitor of lysosomal proteases (E64D) leads to a complete abrogation of the cytotoxic effect of uPARAP-directed ADC 2h9-vc-MMAE. Thereby, lysosomal release of the conjugated drug is shown to be crucial for obtaining a cytotoxic effect.
Figure 9:
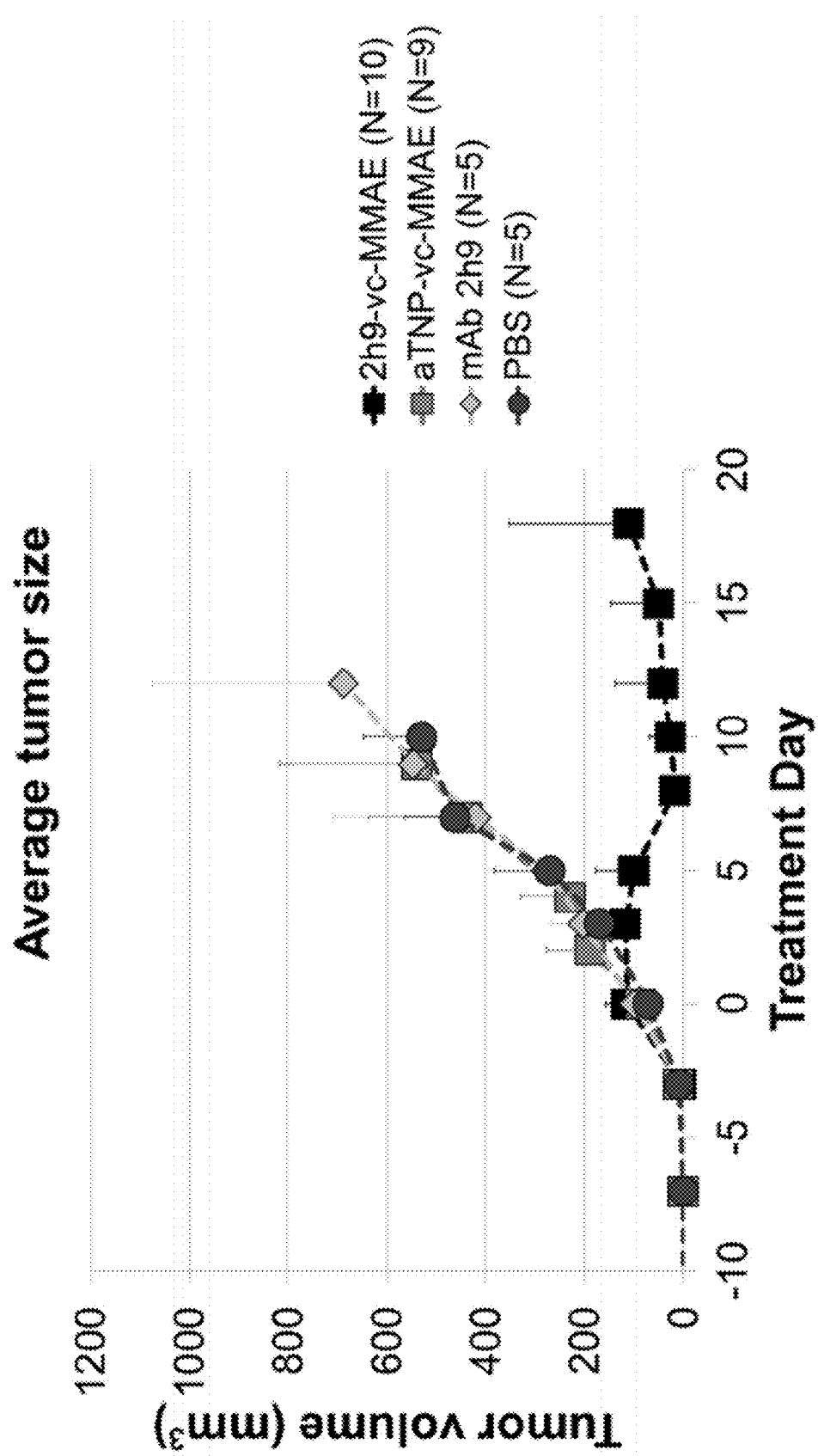
FIG. 9: In vivo testing of the efficacy of uPARAP-directed ADC 2h9-vc-MMAE in combating a uPARAP-positive, subcutaneous xenograft tumour, established by injection of the cell line U937 in CB17 SCID mice. The mice are treated by subcutaneous (s.c.) injection near the tumour with either uPARAP-directed ADC 2h9-vc-MMAE (N=10), control ADC aTNP-vc-MMAE (N=9), unconjugated mAb 2h9 (N=5), or a saline solution (PBS, N=5). All treatments are done in doses of 3 mg/kg/injection mAb component, as 4 doses total, given every 4 days. Day 0 marks the day of first injection, initiated once the tumour has reached a palpable size of 50-100 mm$^3$, and the graph shows the average tumour size across each treatment group. It is seen that treatment with ADC 2h9-vc-MMAE results in a drastic decrease in tumour growth, whereas all other treatment groups reach a point of sacrifice within 10-12 days after starting treatment. This demonstrates that uPARAP-directed ADC 2h9-vc-MMAE is efficient at inhibiting growth of a pre-established uPARAP-positive tumour in vivo. Furthermore, the data from the 2h9-vc-MMAE treated group represent a permanent cure rate of 50% (see also FIG. 10).
Figure 10:
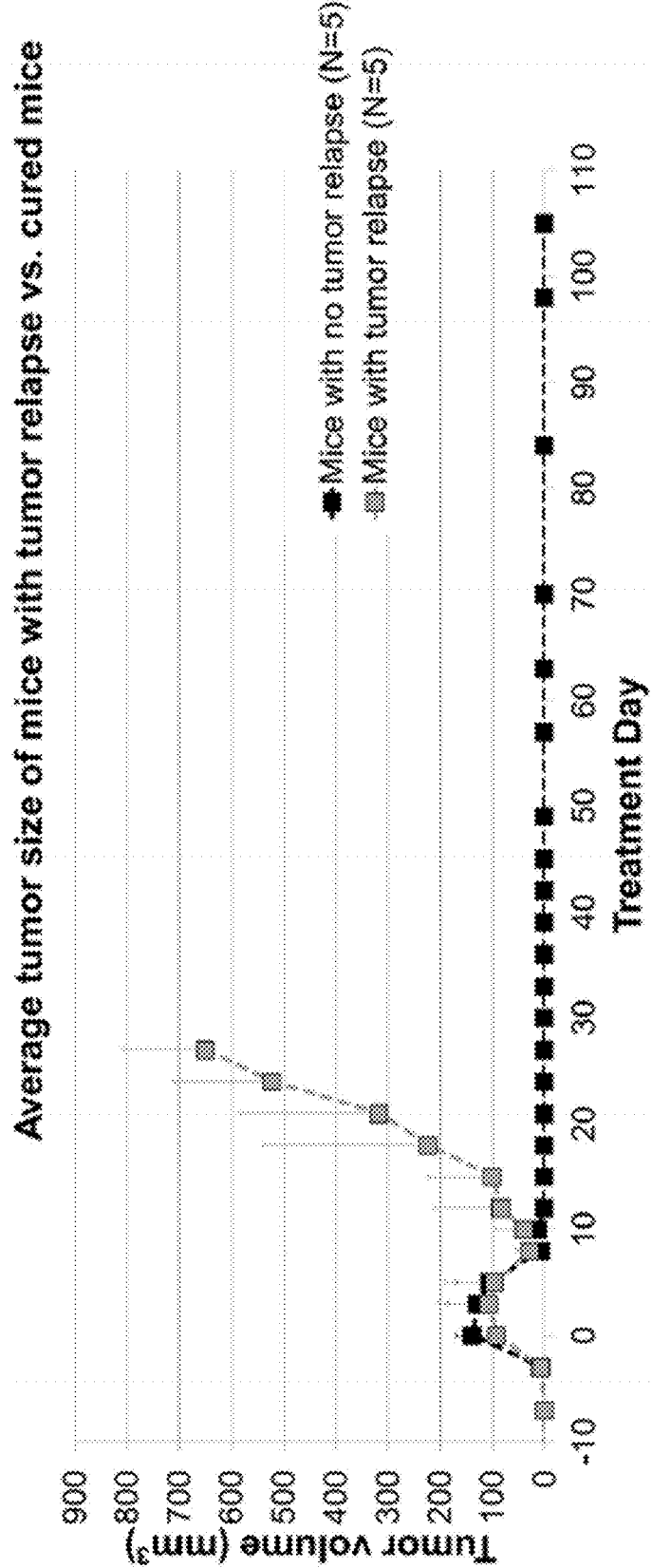
FIG. 10: A more detailed look at the tumour growth of the 2h9-vc-MMAE treated group described in FIG. 9, showing that this group included mice suffering from non-complete treatment and tumour relapse, as well as mice that lost the tumour burden completely and showed no tumour relapse. Of the 10 mice treated with 2h9-vc-MMAE, 5 showed an almost immediate relapse of tumour growth following treatment, quickly reaching a point of sacrifice, whereas the remaining 5 mice lost all signs of the tumour, and remained free from tumour growth for a period of 90 days, giving an overall permanent cure rate of 50% for 2h9-vc-MMAE treated mice following s.c. administration.
Figure 11:
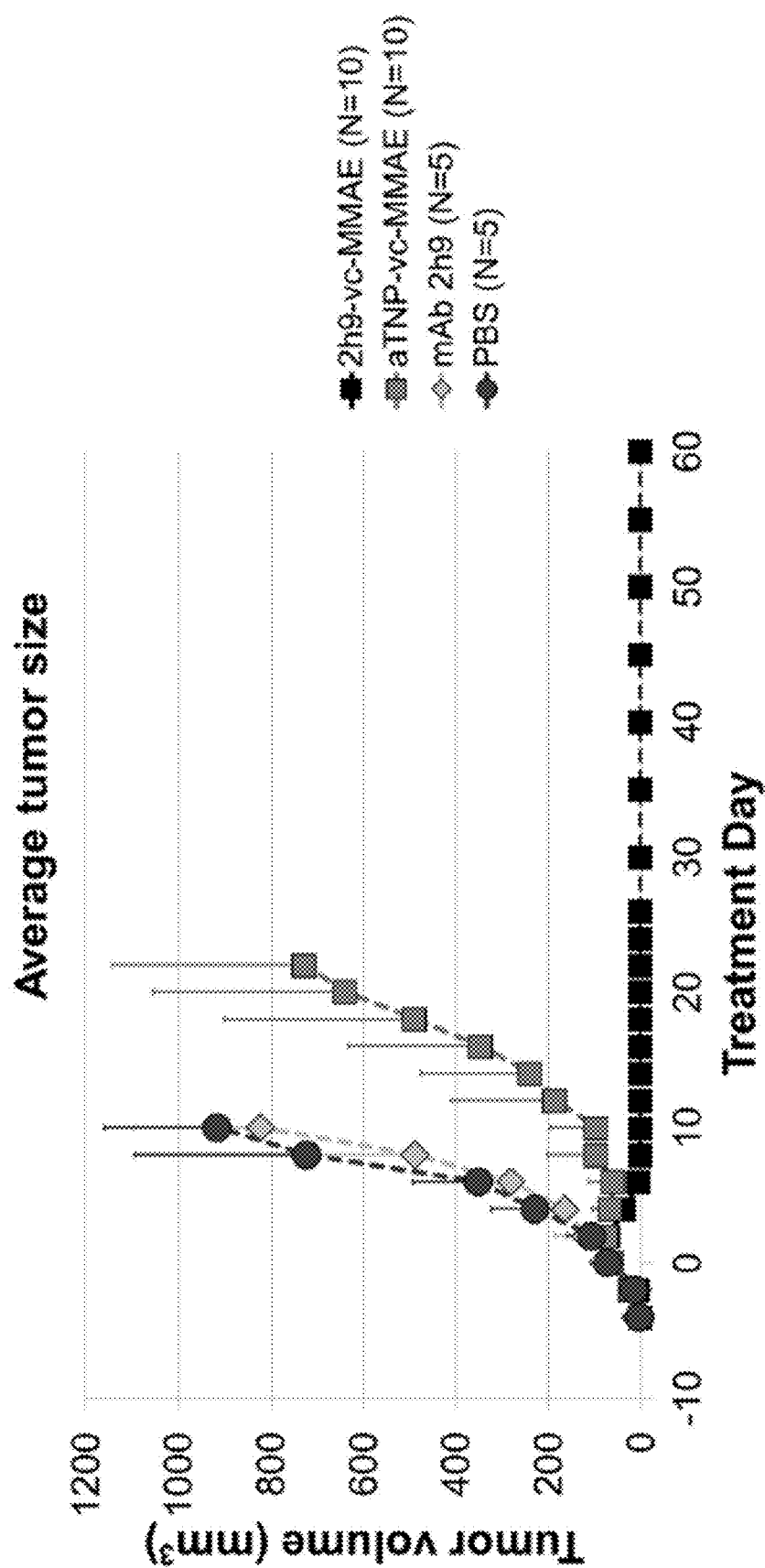
FIG. 11: In vivo testing of the efficacy of uPARAP-directed ADC 2h9-vc-MMAE in combating a uPARAP-positive, subcutaneous xenograft tumour, established by injection of the cell line U937 in CB17 SCID mice. The mice are treated by intravenous (i.v.) injection via the tail veins, with either uPARAP-directed ADC 2h9-vc-MMAE (N=10), control ADC aTNP-vc-MMAE (N=10), unconjugated mAb 2h9 (N=5), or a saline solution (PBS, N=5). All treatments are done in doses of 5 mg/kg/injection mAb component, as 3 doses total, given every 4 days. Day 0 marks the day of first injection, once the tumour has reached a palpable size of 50-100 mm$^3$, and the graph shows the average tumour size across each treatment group. Under these conditions, treatment with uPARAP-directed ADC 2h9-vc-MMAE results in a complete abrogation of the tumour burden in all 10 mice, giving an overall permanent cure rate of 100% of the mice following intravenous administration of this ADC, further demonstrating the efficacy of ADC 2h9-vc-MMAE in combating solid uPARAP-positive tumours.
Figure 12:
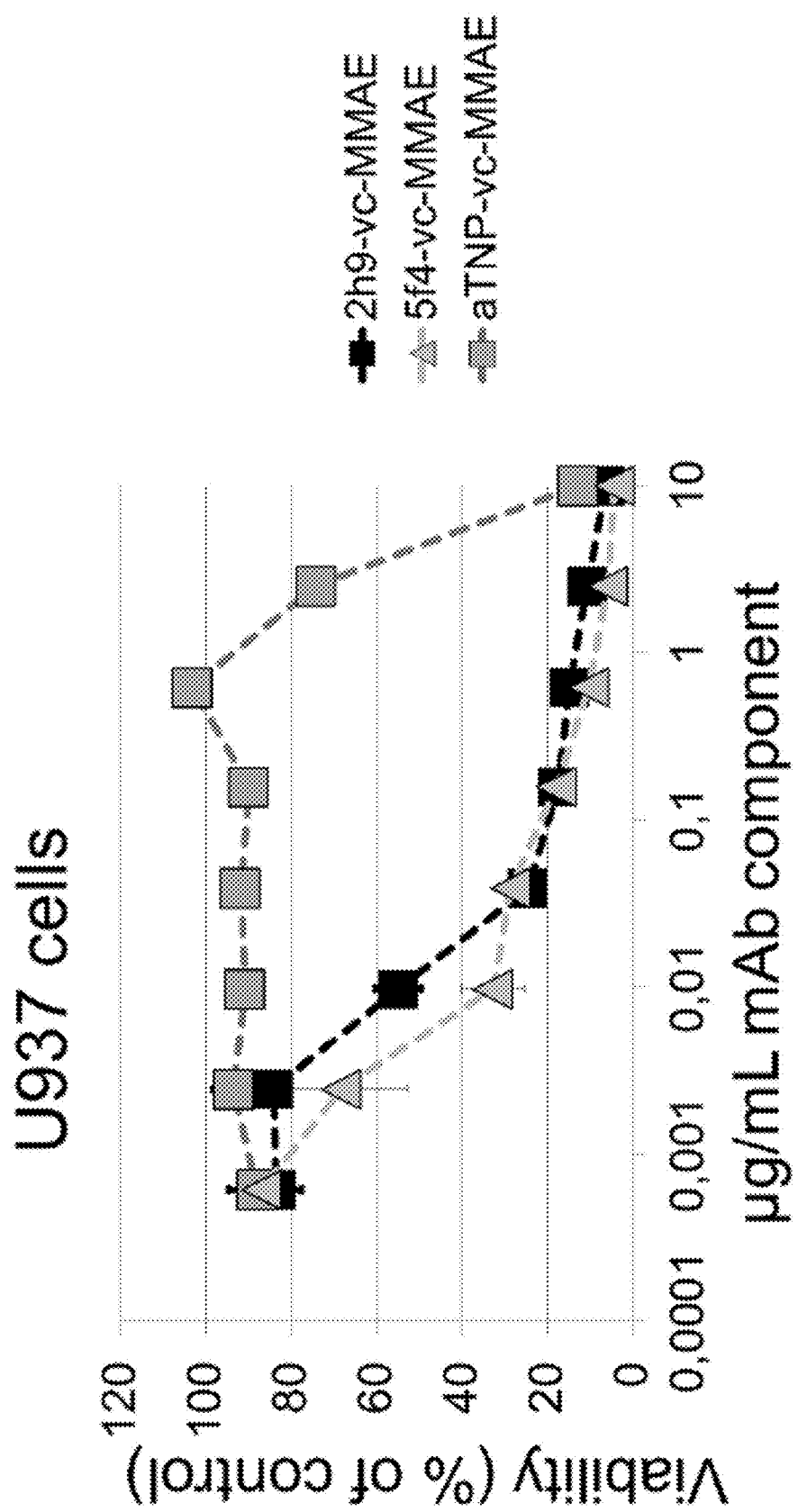
FIG. 12: In vitro cell viability assays showing a specific reduction in overall viability following incubation with either uPARAP-directed ADC 2h9-vc-MMAE or uPARAP-directed ADC 5f4-vc-MMAE, in comparison to a non-targeted ADC (aTNP-vc-MMAE), in the U937 cell line. The data indicates that ADCs based on 5f4 have comparable efficacy to ADCs based on the 2h9 antibody.
Figure 13:
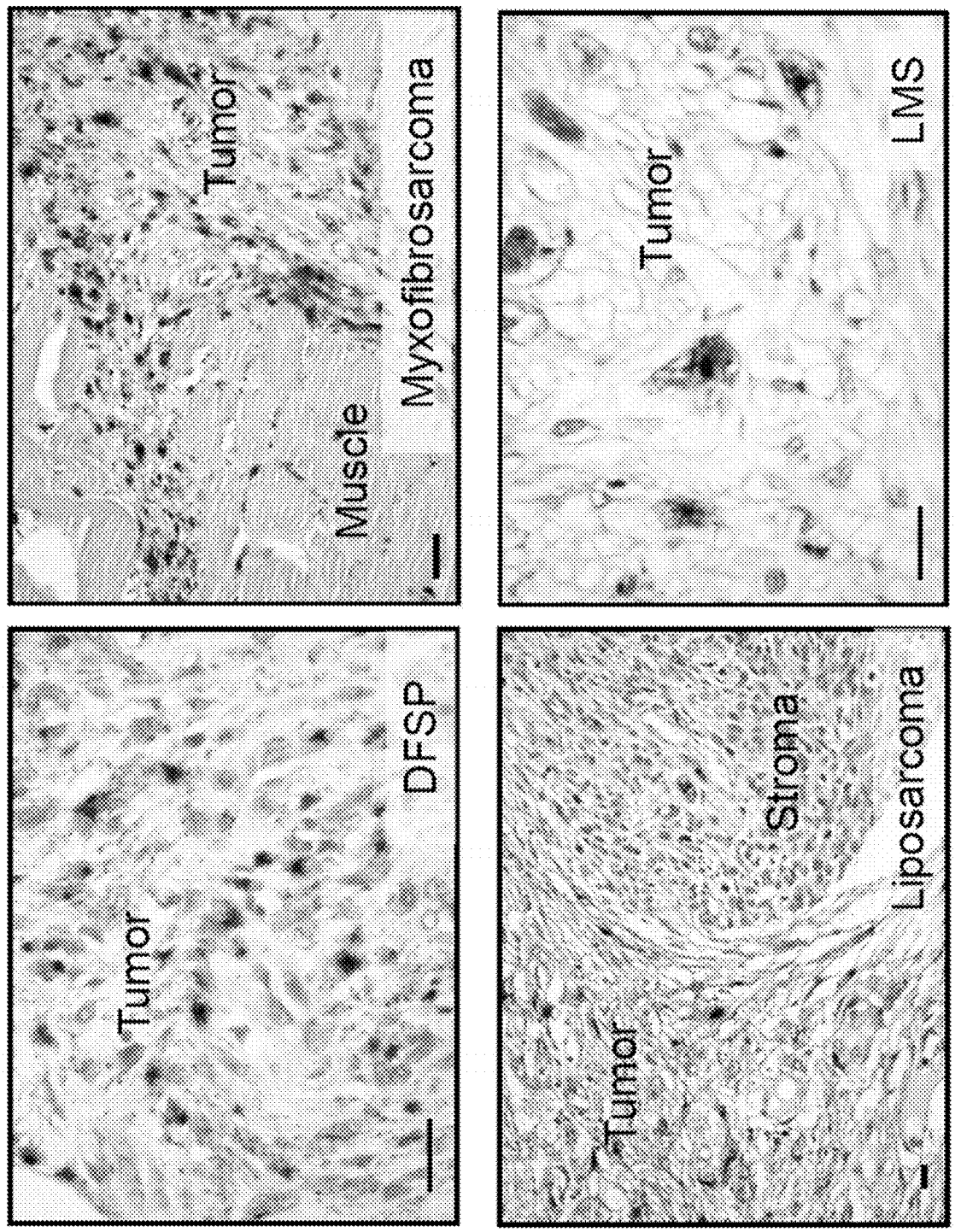
FIG. 13: Immunohistochemistry staining of different sarcomas (liposarcoma, myxofibrosarcoma, dermatofibrosarcoma protuberans (DFSP) and leiomyosarcoma (LMS). The staining method shows tissue expression of uPARAP as a dark reddish-brown color. Expression of uPARAP is evident in sections of malignant cancer (tumor) tissue, whereas sections of non-cancer tissue are devoid of uPARAP, demonstrating the increased expression levels of uPARAP, found in sarcomas. Scale bars: 20 µm.

| Sequences | |
|---|---|
| SEQ ID NO | Description |
| SEQ ID NO: 1 | mAb 2h9 Light Chain full length amino acid sequence |
| SEQ ID NO: 2 | mAb 2h9 Light Chain full length CDR1 |
| SEQ ID NO: 3 | mAb 2h9 Light Chain full length CDR2 |
| SEQ ID NO: 4 | mAb 2h9 Light Chain full length CDR3 |
| SEQ ID NO: 5 | mAb 2h9 Heavy Chain full length amino acid sequence |
| SEQ ID NO: 6 | mAb 2h9 Heavy Chain full length CDR1 |
| SEQ ID NO: 7 | mAb 2h9 Heavy Chain full length CDR2 |
| SEQ ID NO: 8 | mAb 2h9 Heavy Chain full length CDR3 |
| SEQ ID NO: 9 | Fab 2h9 Light Chain amino acid sequence 1-214 |
| SEQ ID NO: 10 | Fab 2h9 Heavy Chain amino acid sequence 1-224 |
| SEQ ID NO: 11 | mAb 5f4 Light Chain variable (VL) region amino acid sequence |
| SEQ ID NO: 12 | mAb 5f4 Light Chain variable (VL) region CDR1 |
| SEQ ID NO: 13 | mAb 5f4 Light Chain variable (VL) region CDR2 |
| SEQ ID NO: 14 | mAb 5f4 Light Chain variable (VL) region CDR3 |
| SEQ ID NO: 15 | mAb 5f4 Heavy Chain variable (VH) region amino acid sequence |
| SEQ ID NO: 16 | mAb 5f4 Heavy Chain variable (VL) region CDR1 |
| SEQ ID NO: 17 | mAb 5f4 Heavy Chain variable (VL) region CDR2 |
| SEQ ID NO: 18 | mAb 5f4 Heavy Chain variable (VL) region CDR3 |
| SEQ ID NO: 19 | Fab 9b7 Light Chain amino acid sequence 1-214 |

Sequences

| SEQ ID NO | Description |
|---|---|
| SEQ ID NO: 20 | Fab 9b7 Light Chain amino acid sequence 8-214 |
| SEQ ID NO: 21 | Fab 9b7 Light Chain CDR1 |
| SEQ ID NO: 22 | Fab 9b7 Light Chain CDR2 |
| SEQ ID NO: 23 | Fab 9b7 Light Chain CDR3 |
| SEQ ID NO: 24 | Fab 9b7 Heavy Chain amino acid sequence 1-221 |
| SEQ ID NO: 25 | Fab 9b7 Heavy Chain amino acid sequence 9-221 |
| SEQ ID NO: 26 | Fab 9b7 Heavy Chain CDR1 |
| SEQ ID NO: 27 | Fab 9b7 Heavy Chain CDR2 |
| SEQ ID NO: 28 | Fab 9b7 Heavy Chain CDR3 |
| SEQ ID NO: 29 | Human uPARAP full length sequence (GenBank: AAI53885.1) |
| SEQ ID NO: 30 | CysR domain as listed by NCBI (amino acids (aa) 46-161 of full length human uPARAP) |
| SEQ ID NO: 31 | CysR domain as predicted by the SMART tool (simple modular architecture research tool) at EMBL (http://smart.embl-heidelberg.de/) {Schultz et al. Proc. Natl. Acad. Sci. USA, Vol. 95, pp. 5857-5864, May 1998} (amino acids (aa) 41-161 of full length human uPARAP) |
| SEQ ID NO: 32 | FN-II domain as listed by NCBI (aa 181-228 of full length Human uPARAP) |
| SEQ ID NO: 33 | FN-II domain as predicted by SMART (aa 180-228 of full length Human uPARAP) |
| SEQ ID NO: 34 | CTLD-1 domain as listed by NCBI (aa 247-361 of full length Human uPARAP) |
| SEQ ID NO: 35 | CTLD-1 domain as predicted by SMART (aa 235-360 of full length Human uPARAP) |
| SEQ ID NO: 36 | CysR-FN-II-CTLD-1 as listed by NCBI (aa 46-361 of full length Human uPARAP) |
| SEQ ID NO: 37 | CysR-FN-II-CTLD-1 as predicted by SMART (aa 41-360 of full length Human uPARAP) |
| SEQ ID NO: 38 | CysR-FN-II as listed by NCBI (aa 46-228 of full length Human uPARAP) |
| SEQ ID NO: 39 | CysR-FN-II as predicted by SMART (aa 41-228 of full length Human uPARAP) |
| SEQ ID NO: 40 | FN-II-CTLD-1 as listed by NCBI (aa 181-361 of full length Human uPARAP) |
| SEQ ID NO: 41 | FN-II-CTLD-1 as predicted by SMART (aa 180-360 of full length Human uPARAP) |
| SEQ ID NO: 42 | mAb 2h9 Light Chain Paratome-predicted ABR1 |
| SEQ ID NO: 43 | mAb 2h9 Light Chain Paratome-predicted ABR2 |
| SEQ ID NO: 44 | mAb 2h9 Light Chain Paratome-predicted ABR3 |
| SEQ ID NO: 45 | mAb 2h9 Heavy Chain Paratome-predicted ABR1 |
| SEQ ID NO: 46 | mAb 2h9 Heavy Chain Paratome-predicted ABR2 |
| SEQ ID NO: 47 | mAb 2h9 Heavy Chain Paratome-predicted ABR3 |
| SEQ ID NO: 48 | mAb 5f4 Light Chain Paratome-predicted ABR1 |
| SEQ ID NO: 49 | mAb 5f4 Light Chain Paratome-predicted ABR2 |
| SEQ ID NO: 50 | mAb 5f4 Light Chain Paratome-predicted ABR3 |
| SEQ ID NO: 51 | mAb 5f4 Heavy Chain Paratome-predicted ABR1 |
| SEQ ID NO: 52 | mAb 5f4 Heavy Chain Paratome-predicted ABR2 |
| SEQ ID NO: 53 | mAb 5f4 Heavy Chain Paratome-predicted ABR3 |
| SEQ ID NO: 54 | mAb 9b7 Light Chain Paratome-predicted ABR1 |
| SEQ ID NO: 55 | mAb 9b7 Light Chain Paratome-predicted ABR2 |
| SEQ ID NO: 56 | mAb 9b7 Light Chain Paratome-predicted ABR3 |
| SEQ ID NO: 57 | mAb 9b7 Heavy Chain Paratome-predicted ABR1 |
| SEQ ID NO: 58 | mAb 9b7 Heavy Chain Paratome-predicted ABR2 |
| SEQ ID NO: 59 | mAb 9b7 Heavy Chain Paratome-predicted ABR3 |

Complementarity Determining Regions (CDRs) were predicted according to the definition scheme of Kabat et al. as specified in the references Kabat et al. (1983), Kabat et al. (1991) and Wu and Kabat (2008) using a computerized Kabat-numbering programme as published by Dunbar and Deane (2016). Antigen binding regions (ABRs) according to the Paratome algorithm were also predicted as specified in the references Kunik et al. (2012a and b). The ABRs represent alternative CDRs of the antibodies disclosed herein.

Complete regions involved in antigen recognition and binding may deviate slightly from the specified CDRs and ABRs and all sequence data included in the variable regions or Fab fragments specified here are covered as potentially contributing to antigen binding. Methods or algorithms different from those employed here may be used for identification of potential binding/recognition regions. Therefore, in addition to the predicted CDRs as presented herein, this invention covers any amino acid sequences predicted to represent CDRs or ABRs in mAbs 2h9, 5f4 and 9b7 based on the respective Fab regions and variable regions (SEQ ID NOs: 9, 10, 11, 15, 20 and 25, respectively), using such methods or algorithms. Examples of additional methods and algorithms for the prediction of CDRs include, but are not limited to, the IMGT system (LeFranc et al., (2003)).

Due to the position of primer regions during sequencing of the Fab 9B7 light and heavy chains some ambiguity is expected in the N-terminal region of these sequences. Thus, the first 7 amino acids of SEQ ID NO: 19 may not be exact. The same goes for amino acids 1-8 of SEQ ID NO: 24. SEQ ID NOs: 20 and 25 correspond to SEQ ID NOs: 19 and 24 respectively without the ambiguous N-terminal amino acids.

DETAILED DESCRIPTION

The antibody-drug conjugate targeting uPARAP of the present disclosure comprises
  a) an antibody capable of binding to the cystein-rich domain (CysR), the Fibronectin type II (FN-II) domain and/or to the C-type lectin-like domain 1 (CTLD 1) of uPARAP,
  b) an active agent, and
  c) optionally a linker which links a) to b).

In a particular aspect, the antibody-drug conjugate targeting uPARAP of the present disclosure comprises
  a. an antibody or antigen-binding fragment thereof capable of binding to:
    i. the amino acid sequence of SEQ ID NO: 36 or 37 (CysR-FN-II-CTLD-1 domains of uPARAP),
    ii. the amino acid sequence of SEQ ID NO: 38 or 39 (CysR-FN-II domains of uPARAP),
    iii. the amino acid sequence of SEQ ID NO: 40 or 41 (FN-II-CTLD-1 domains of uPARAP),
    iv. the amino acid sequence of SEQ ID NO: 30 or 31 (the cystein-rich domain (CysR) of uPARAP)
    v. the amino acid sequence of SEQ ID NO: 32 or 33 (the Fibronectin type II (FN-II) domain of uPARAP), and/or
    vi. the amino acid sequence of SEQ ID NO: 34 or 35 (the C-type lectin-like domain 1 (CTLD 1) of uPARAP),
  b. an active agent, and optionally
  c. a linker which links a) to b).

Antibody Directed Against uPARAP

The anti-uPARAP antibody of the present disclosure is internalised upon binding to uPARAP at the cell surface, thus allowing for intracellular actions of the active agent of the ADC complex. It is known from e.g. WO 2010/111198 that not all antibodies capable of binding to uPARAP are internalised at the same rate or in the same amount. Indeed, some anti-uPARAP antibodies are not internalised at all and are therefore not suitable for use in ADCs.

The uPARAP receptor consists of an N-terminal cysteine-rich domain (CysR), a fibronectin type II (FN-II) domain, and eight C-type lectin-like domains (CTLDs 1-8), cf. FIG. 1. Short amino acid sequences connect the individual domains. The data presented herein suggests that anti-uPARAP antibodies targeting the three most N-terminal domains of uPARAP are very efficient for use in ADCs.

Thus, the anti-uPARAP antibody of the present disclosure preferably binds to the N-terminal region of uPARAP, more preferably to an epitope located in the three most N-terminal domains of uPARAP, that is the cystein-rich domain, the fibronectin type II domain and/or C-type lectin-like domain 1, including the linker sequences connecting these domains of uPARAP.

Thus, the anti-uPARAP antibody of the present disclosure is capable of binding to a peptide comprising or consisting of the cystein-rich domain (CysR) (SEQ ID NO: 30 or 31), the fibronectin type II (FN-II) domain (SEQ ID NO: 32 or 33) and/or to the C-type lectin-like domain 1 (CTLD 1) (SEQ ID NO: 34 or 35) of uPARAP.

The cystein-rich domain, the fibronectin type II domain and the C-type lectin-like domain 1 including the linker sequences connecting these domains as listed by NCBI correspond to aa 46-361 of full length human uPARAP. Thus, in one embodiment the epitope for the anti-uPARAP antibody is located in aa 46-361 of SEQ ID NO: 29 (full length human uPARAP). In one embodiment, the anti-uPARAP antibody of the present disclosure binds to an epitope located in aa 31-365 of SEQ ID NO: 29, more preferably in aa 46-361 of SEQ ID NO: 29, corresponding to SEQ ID NO: 36 herein. SMART predicts CYSR-FN-II-CTLD1 including the linker sequences connecting these domains to aa 41-360 of SEQ ID NO: 29. Thus, in one embodiment the epitope for the anti-uPARAP antibody is located in aa 41-360 of SEQ ID NO: 29, corresponding to SEQ ID NO: 37 herein.

In one embodiment, the anti-uPARAP antibody of the present disclosure binds to the CysR domain and/or the CTLD-1 domain.

In one embodiment, the anti-uPARAP antibody of the present disclosure binds to the CysR domain, which is predicted by NCBI to consist of aa 46-161 of full length Human uPARAP, corresponding to SEQ ID NO: 30 herein, and by SMART to consist of aa 41-161 of full length Human uPARAP, corresponding to SEQ ID NO: 31 herein. I.e. in one embodiment it binds to an epitope located in aa 46-161 or 41-161 of SEQ ID NO: 29.

In one embodiment, the anti-uPARAP antibody of the present disclosure binds to the FN-II domain, which is predicted by NCBI to consist of aa 181-228 of full length Human uPARAP, corresponding to SEQ ID NO: 32 herein, and by SMART to consist of aa 180-228 of full length Human uPARAP, corresponding to SEQ ID NO: 33 herein. I.e. in one embodiment it binds to an epitope located in aa 181-228 or 180-228 of SEQ ID NO: 29.

In one embodiment, the anti-uPARAP antibody of the present disclosure binds to the CTLD-1 domain which is predicted by NCBI to consist of aa 247-361 of full length Human uPARAP, corresponding to SEQ ID NO: 34 herein, and by SMART to consist of aa 235-360 of full length human uPARAP, corresponding to SEQ ID NO: 35 herein. I.e. in one embodiment it binds to an epitope located in aa 247-361 or 235-360 of SEQ ID NO: 29.

In one embodiment, the anti-uPARAP antibody of the present disclosure is capable of binding to a peptide comprising or consisting of the CysR and FN-II domain including the linker sequences connecting these domains, which is predicted by NCBI to consist of aa 46-228 of full length human uPARAP, corresponding to SEQ ID NO: 38, and by SMART to consist of aa 41-228 of full length human uPARAP, corresponding to SEQ ID NO: 39 herein. I.e. in one embodiment it binds to an epitope located in aa 46-228 or 41-228 of SEQ ID NO: 29.

In one embodiment, the anti-uPARAP antibody of the present disclosure is capable of binding to a peptide comprising or consisting of the FN-II and CTLD-1 domain including the linker sequences connecting these domains, which is predicted by NCBI to consist of aa 181-361 of full length human uPARAP, corresponding to SEQ ID NO: 40 herein, and by SMART to consist of aa 180-360 of full length human uPARAP, corresponding to SEQ ID NO: 41 herein. I.e. in one embodiment it binds to an epitope located in aa 180-361 or 181-360 of SEQ ID NO: 29.

In one embodiment the anti-uPARAP antibody of the present disclosure is the mouse monoclonal IgG1K antibody of clone 2.h.9: F12 commercially available from Merck Millipore (www.merckmillipore.com/DK/en/product/Anti-UPAR-Associated-Protein-Antibody%2C-clone-2.h.9%3AF12, MM_NF-MAB2613?cid=BI-XX-BRC-P-GOOG-ANTI-B302-1075) or a functional fragment or variant thereof, such as a chimeric or humanised version thereof. Mouse monoclonal IgG1$_k$ antibody clone 2.h.9: F12 is referred to herein as the "2h9" antibody or "mAb 2h9". The 2h9 antibody reacts with both human and mouse uPARAP and is therefore well suited for both preclinical and clinical studies.

Previous studies indicate that the epitope for the 2h9 antibody is located in the three most N-terminal domains of uPARAP, particularly in the CysR domain or the CTLD-1 domain. A soluble recombinant protein consisting of the three n-terminal domains of uPARAP (CysR, FN-II and CTLD-1) binds to immobilized 2h9 in a BIAcore setup, limiting the location of binding by mAb 2h9 to these three n-terminal domains (Jürgensen et al., 2011, JBC 286(37): 32736-48). Furthermore, swapping the FN-II domain of uPARAP with the FN-II domain of other members of the same receptor family has no effect on binding of mAb 2h9, suggesting that the FN-II domain does not likely contain the epitope for mAb 2h9 (Jürgensen et al., 2014, JBC 289(11): 7935-47). This effectively limits binding of mAb 2h9 to either the CysR domain, or the CTLD-1 domain.

The predicted CDRs of immunoglobulin light chain variable region of mAb 2h9 correspond to SEQ ID NOs: 2-4 and the predicted CDRs of immunoglobulin heavy chain variable region of mAb 2h9 correspond to SEQ ID NOs: 6-8.

In one embodiment the anti-uPARAP antibody of the present disclosure is an antibody corresponding to the 2h9 antibody or a functional fragment or variant thereof selected from the group consisting of:
a. an antibody or antigen-binding fragment thereof comprising
  i. an immunoglobulin light chain variable region comprising or consisting of the amino acid sequence of SEQ ID NO: 1 or 9 or a sequence having at least 70% sequence identity thereto, such as at least 80% sequence identity thereto, for example at least 90% sequence identity thereto, and/or
  ii. an immunoglobulin heavy chain variable region comprising or consisting of the amino acid sequence of SEQ ID NO: 5 or 10 or a sequence having at least 70% sequence identity thereto, such as at least 80% sequence identity thereto, for example at least 90% sequence identity thereto,
b. an antibody or antigen-binding fragment thereof that binds to the same epitope as the antibody of a),
c. a humanised version of the antibody or antigen-binding fragment thereof of a), or a humanised version of the antibody or antigen-binding fragment thereof of b),
d. a chimeric version of the antibody or antigen-binding fragment thereof of a), or a chimeric version of the antibody or antigen-binding fragment thereof of b),
e. an antibody or antigen-binding fragment thereof comprising
  i. one or more of the amino acid sequences of SEQ ID NOs: 2, 3, 4, 6, 7 and 8, or
  ii. the amino acid sequences of SEQ ID NOs: 2, 3 and 4, and/or the amino acid sequences of SEQ ID NOs 6, 7 and 8,
f. an antibody or antigen-binding fragment thereof comprising
  i. one or more of the amino acid sequences of SEQ ID Nos: 42, 43, 44, 45, 46 and 47, or
  ii. the amino acid sequences of SEQ ID NOs: 42, 43 and 44, and/or the amino acid sequences of SEQ ID NOs 45, 46 and 47.

To preserve antigen recognition of the antibodies disclosed herein the sequence variance is usually not in the CDRs or ABRs. Thus, in a preferred embodiment, any sequence variation is located outside the CDRs or ABRs. All variant antibodies and antigen binding fragments disclosed herein retain the capability to bind to uPARAP.

For example, the antibody of the present disclosure may comprise
a. an immunoglobulin light chain variable region comprising the amino acid sequence of SEQ ID NO: 1 or 9 or a sequence having at least 70% sequence identity thereto, such as at least 80% sequence identity thereto, for example at least 90% sequence identity thereto, and further comprising
  i. a CDR1 having an aa sequence according to SEQ ID NO: 2,
  ii. a CDR2 having an aa sequence according to SEQ ID NO: 3,
  iii. a CDR3 having an aa sequence according to SEQ ID NO: 4, and
b. an immunoglobulin heavy chain variable region comprising the amino acid sequence of SEQ ID NO: 5 or 10 or a sequence having at least 70% sequence identity thereto, such as at least 80% sequence identity thereto, for example at least 90% sequence identity thereto, and further comprising
  i. a CDR1 having an aa sequence according to SEQ ID NO: 6,
  ii. a CDR2 having an aa sequence according to SEQ ID NO: 7,
  iii. a CDR3 having an aa sequence according to SEQ ID NO: 8,
  wherein any sequence variance is outside the CDRs.

Alternatively, the antibody of the present disclosure may comprise
a. an immunoglobulin light chain variable region comprising the amino acid sequence of SEQ ID NO: 1 or 9 or a sequence having at least 70% sequence identity thereto, such as at least 80% sequence identity thereto, for example at least 90% sequence identity thereto, and further comprising
  i. an ABR1 having an aa sequence according to SEQ ID NO: 42,
  ii. an ABR 2 having an aa sequence according to SEQ ID NO: 43,
  iii. an ABR 3 having an aa sequence according to SEQ ID NO: 44, and
b. an immunoglobulin heavy chain variable region comprising the amino acid sequence of SEQ ID NO: 5 or 10 or a sequence having at least 70% sequence identity thereto, such as at least 80% sequence identity thereto, for example at least 90% sequence identity thereto, and further comprising
  i. an ABR 1 having an aa sequence according to SEQ ID NO: 45,
  ii. an ABR 2 having an aa sequence according to SEQ ID NO: 46,
  iii. an ABR 3 having an aa sequence according to SEQ ID NO: 47,
  wherein any sequence variance is outside the ABRs.

In one embodiment the anti-uPARAP antibody of the present disclosure is the mouse monoclonal antibody 5f4 or a functional fragment or variant thereof. The 5f4 antibody is IgG1$_K$.

Studies have shown that the epitope for 5f4 is located in the FN-II domain of uPARAP. In Jürgensen et al., 2014 it is shown that the 5f4 antibody is capable of binding to wild-type uPARAP and to artificial members of the mannose receptor family, where the wildtype FN-II domain has been switched with that of uPARAP. 5f4 is not capable of binding to the other members of the mannose receptor family proteins in their wildtype form, or with uPARAP where the wildtype FN-II domain has been switched with equivalent domains from the other members of the mannose receptor family (Jürgensen et al., 2014, JBC 289(11): 7935-47).

In one embodiment the anti-uPARAP antibody of the present disclosure is an antibody corresponding to the 5f4 antibody or a functional fragment or variant thereof selected from the group consisting of
a. an antibody or antigen-binding fragment thereof comprising
 i. an immunoglobulin light chain variable region comprising or consisting of the amino acid sequence of SEQ ID NO: 11 or a sequence having at least 70% sequence identity thereto, such as at least 80% sequence identity thereto, for example at least 90% sequence identity thereto, and/or
 ii. an immunoglobulin heavy chain variable region comprising or consisting of the amino acid sequence of SEQ ID NO: 15 or a sequence having at least 70% sequence identity thereto, such as at least 80% sequence identity thereto, for example at least 90% sequence identity thereto,
b. an antibody or antigen-binding fragment thereof that binds to the same epitope as the antibody of a),
c. a humanised version of the antibody or antigen-binding fragment thereof of a), or a humanised version of the antibody or antigen-binding fragment thereof of b),
d. a chimeric version of the antibody or antigen-binding fragment thereof of a), or a chimeric version of the antibody or antigen-binding fragment thereof of b),
e. an antibody or antigen-binding fragment thereof comprising
 i. one or more of the amino acid sequences of SEQ ID NOs: 12, 13, 14, 16, 17 and 18, or
 ii. the amino acid sequences of SEQ ID NOs: 12, 13 and 14, and/or the amino acid sequences of SEQ ID NOs 16, 17 and 18.
f. an antibody or antigen-binding fragment thereof comprising
 i. one or more of the amino acid sequences of SEQ ID NOs: 48, 49, 50, 51, 52 and 53, or
 ii. the amino acid sequences of SEQ ID NOs: 48, 49 and 50, and/or the amino acid sequences of SEQ ID NOs 51, 52 and To allow for some sequence variance outside the CDRs, the antibody of the present disclosure may comprise
a. an immunoglobulin light chain variable region comprising the amino acid sequence of SEQ ID NO: 11 or a sequence having at least 70% sequence identity thereto, such as at least 80% sequence identity thereto, for example at least 90% sequence identity thereto, and further comprising
 i. a CDR1 having an aa sequence according to SEQ ID NO: 12,
 ii. a CDR2 having an aa sequence according to SEQ ID NO: 13,
 iii. a CDR3 having an aa sequence according to SEQ ID NO: 14, and
b. an immunoglobulin heavy chain variable region comprising the amino acid sequence of SEQ ID NO: 15 or a sequence having at least 70% sequence identity thereto, such as at least 80% sequence identity thereto, for example at least 90% sequence identity thereto, and further comprising
 i. a CDR1 having an aa sequence according to SEQ ID NO: 16,
 ii. a CDR2 having an aa sequence according to SEQ ID NO: 17,
 iii. a CDR3 having an aa sequence according to SEQ ID NO: 18,
 wherein any sequence variance is outside the CDRs.

Alternatively, the antibody of the present disclosure may comprise
a. an immunoglobulin light chain variable region comprising the amino acid sequence of SEQ ID NO: 11 or a sequence having at least 70% sequence identity thereto, such as at least 80% sequence identity thereto, for example at least 90% sequence identity thereto, and further comprising
 i. an ABR1 having an aa sequence according to SEQ ID NO: 48,
 ii. an ABR 2 having an aa sequence according to SEQ ID NO: 49,
 iii. an ABR 3 having an aa sequence according to SEQ ID NO: 49, and
b. an immunoglobulin heavy chain variable region comprising the amino acid sequence of SEQ ID NO: 15 or a sequence having at least 70% sequence identity thereto, such as at least 80% sequence identity thereto, for example at least 90% sequence identity thereto, and further comprising
 i. an ABR 1 having an aa sequence according to SEQ ID NO: 51,
 ii. an ABR 2 having an aa sequence according to SEQ ID NO: 52,
 iii. an ABR 3 having an aa sequence according to SEQ ID NO: 53,
 wherein any sequence variance is outside the ABRs.

In one embodiment the anti-uPARAP antibody of the present disclosure is the mouse monoclonal antibody 9b7 (mAb 9b7) or a functional fragment or variant thereof. Previous studies indicate that the epitope for the 9b7 antibody is located in the three most N-terminal domains of uPARAP. When a soluble recombinant protein consisting of the three N-terminal domains of uPARAP (CysR, FN-II and CTLD-1) is immobilized in a BIAcore setup, mAb 9b7 binds to this construct.

In one embodiment the anti-uPARAP antibody is selected from the group consisting of
a. an antibody or antigen-binding fragment thereof comprising
 i. an immunoglobulin light chain variable region comprising or consisting of the amino acid sequence of SEQ ID NO: 19 or 20 or a sequence having at least 70% sequence identity thereto, such as at least 80% sequence identity thereto, for example at least 90% sequence identity thereto, and/or
 ii. an immunoglobulin heavy chain variable region comprising or consisting of the amino acid sequence of SEQ ID NO: 24 or 25 or a sequence having at least 70% sequence identity thereto, such as at least 80% sequence identity thereto, for example at least 90% sequence identity thereto,
b. an antibody or antigen-binding fragment thereof that binds to the same epitope as the antibody of a),
c. a humanised version of the antibody or antigen-binding fragment thereof of a), or a humanised version of the antibody or antigen-binding fragment thereof of b),
d. a chimeric version of the antibody or antigen-binding fragment thereof of a), or a chimeric version of the antibody or antigen-binding fragment thereof of b),
e. an antibody or antigen-binding fragment thereof comprising i. one or more of the amino acid sequences of SEQ ID NOs: 21, 22, 23, 26, 27 and 28, or
ii. the amino acid sequences of SEQ ID NOs: 21, 22 and 23, and/or the amino acid sequences of SEQ ID NOs 26, 27 and
i. one or more of the amino acid sequences of SEQ ID NOs: 54, 55, 56, 57, 58 and 59, or
ii. the amino acid sequences of SEQ ID NOs: 54, 55 and 56, and/or the amino acid sequences of SEQ ID NOs: 57, 58 and 59.

In one embodiment, the antibody of the present disclosure may comprise
a. an immunoglobulin light chain variable region comprising the amino acid sequence of SEQ ID NO: 19 or 20 or a sequence having at least 70% sequence identity thereto, such as at least 80% sequence identity thereto, for example at least 90% sequence identity thereto, and further comprising
  i. a CDR1 having an aa sequence according to SEQ ID NO: 21,
  ii. a CDR2 having an aa sequence according to SEQ ID NO: 22,
  iii. a CDR3 having an aa sequence according to SEQ ID NO: 23, and
b. an immunoglobulin heavy chain variable region comprising the amino acid sequence of SEQ ID NO: 24 or 25 or a sequence having at least 70% sequence identity thereto, such as at least 80% sequence identity thereto, for example at least 90% sequence identity thereto, and further comprising
  i. a CDR1 having an aa sequence according to SEQ ID NO: 26,
  ii. a CDR2 having an aa sequence according to SEQ ID NO: 27,
  iii. a CDR3 having an aa sequence according to SEQ ID NO: 28,
  wherein any sequence variance is outside the CDRs.

Alternatively, the antibody of the present disclosure may comprise
a. an immunoglobulin light chain variable region comprising the amino acid sequence of SEQ ID NO: 19 or 20 or a sequence having at least 70% sequence identity thereto, such as at least 80% sequence identity thereto, for example at least 90% sequence identity thereto, and further comprising
  i. an ABR1 having an aa sequence according to SEQ ID NO: 54,
  ii. an ABR 2 having an aa sequence according to SEQ ID NO: 55,
  iii. an ABR 3 having an aa sequence according to SEQ ID NO: 56, and
b. an immunoglobulin heavy chain variable region comprising the amino acid sequence of SEQ ID NO: 24 or 25 or a sequence having at least 70% sequence identity thereto, such as at least 80% sequence identity thereto, for example at least 90% sequence identity thereto, and further comprising
  i. an ABR 1 having an aa sequence according to SEQ ID NO: 57,
  ii. an ABR 2 having an aa sequence according to SEQ ID NO: 58,
  iii. an ABR 3 having an aa sequence according to SEQ ID NO: 59,
  wherein any sequence variance is outside the ABRs.

By "antibody" we include substantially intact antibody molecules, chimeric antibodies, humanised antibodies, human antibodies, single chain antibodies, bispecific antibodies, antibody heavy chains, antibody light chains, homodimers and heterodimers of antibody heavy and/or light chains, and antigen-binding fragments and derivatives of the same.

By "antigen-binding fragment" we mean a functional fragment of an antibody that is capable of binding to uPARAP.

In one embodiment, the anti-uPARAP antibody according to the present disclosure is selected from a mouse antibody, a chimeric antibody, a human antibody, a humanised antibody, a humanised antigen-binding fragment, a Fab fragment, a Fab' fragment, a F(ab')2 fragment, an Fv fragment, a single chain antibody (SCA) such as an scFv, the variable portion of the heavy and/or light chains thereof, or a Fab miniantibody, where these fragments or modified antibodies may be derived from mouse, chimeric, human or humanized antibodies.

In one embodiment the anti-uPARAP antibody is a humanised or fully human monoclonal antibody or antigen-binding fragment thereof.

In one embodiment, the anti-uPARAP antibody of the present disclosure is a recombinant antibody.

The anti-uPARAP antibody of the present disclosure may be of any immunoglobulin class including IgG, IgM, IgD, IgE, IgA, and any subclass thereof. IgG subclasses are also well known to those in the art and include but are not limited to human IgG1, IgG2, IgG3 and IgG4. In one embodiment the antibody is an IgG monoclonal antibody. In one embodiment the antibody is $IgG1_K$.

In one embodiment the anti-uPARAP antibody is an antigen-binding fragment.

The advantages of using antibody fragments, rather than whole antibodies, are several-fold. The smaller size of the fragments may lead to improved pharmacological properties, such as better tissue penetration. Moreover, antigen-binding fragments can be expressed in and secreted from *E. coli* or other non-mammalian host cells, thus allowing the facile production of large amounts of said fragments.

Fab is the fragment which contains a monovalent antigen-binding fragment of an antibody molecule which can be produced by digestion of whole antibody with the enzyme papain, or other specific means of proteolysis to yield a light chain and a portion of the heavy chain.

F(ab')2 is the fragment of the antibody that can be obtained by treating whole antibody with the enzyme pepsin, or other specific means of proteolysis to yield a bivalent antigen-binding fragment without subsequent reduction; F(ab')2 is a dimer of two Fab fragments held together by two disulfide bonds.

Fv is a genetically engineered fragment containing the variable region of the light chain and the variable region of the heavy chain, expressed as two chains.

Single chain antibody (SCA) is a genetically engineered molecule containing the variable region of the light chain and the variable region of the heavy chain, linked by a suitable polypeptide linker as a genetically fused, single chain molecule, including an scFv.

Methods of generating antibodies and antibody fragments are well known in the art. For example, antibodies may be generated via any one of several methods which employ induction of in vivo production of antibody molecules, screening of immunoglobulin libraries, or generation of monoclonal antibody molecules by cell lines in culture. These include, but are not limited to, the hybridoma technique, the human B-cell hybridoma technique, and the Epstein-Barr virus (EBV)-hybridoma technique.

Likewise, antibody fragments can be obtained using methods well known in the art. For example, antibody fragments according to the present invention can be prepared by proteolytic hydrolysis of the antibody with various enzymes or by expression in *E. coli* or mammalian cells (e.g. chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, human or humanised antibodies are preferably used. Humanised forms of non-human (e.g. murine) antibodies are genetically engineered chimeric antibodies or antibody fragments having preferably minimal-portions derived from non-human antibodies. Humanised antibodies include antibodies in which complementary determining regions (CDRs) of a human antibody (recipient antibody) are replaced by residues from a complementary determining region of a non-human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported CDR or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody.

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described by substituting human CDRs with corresponding non-human CDRs. Accordingly, such humanised antibodies are chimeric antibodies, wherein substantially less than an intact human variable domain has been substituted by the corresponding sequence from a non-human species. In practice, humanised antibodies may be typically human antibodies in which some CDR residues and possibly some framework residues are substituted by residues from analogous sites in non-human antibodies.

Human antibodies can also be identified using various techniques known in the art, including phage display libraries.

Once suitable antibodies are obtained, they may be tested for antigen specificity, for example by ELISA.

Active Agent

The anti-uPARAP ADC of the present disclosure comprises an active agent, i.e. a drug, which can be delivered intracellularly to cells expressing uPARAP on their surface. The active agent may e.g. be a therapeutic agent, a cytotoxic agent, a radioisotope or a detectable label. In a preferred embodiment the active agent is a therapeutic agent.

In one embodiment the active agent is a chemotherapeutic agent. Classes of chemotherapeutic agents include alkylating agents, anthracyclines, antimetabolites, anti-microtubule/anti-mitotic agents, histone deacetylase inhibitors, kinase inhibitors, peptide antibiotics, platinum-based antineoplastics, topoisomerase inhibitors and cytotoxic antibiotics.

In a preferred embodiment the active agent is a cytotoxic agent allowing for efficient killing of the cells expressing uPARAP.

In one embodiment the active agent is an anti-mitotic agent, such as monomethyl auristatin E (MMAE), monomethyl auristatin F (MMAF), a taxane (e.g. Paclitaxel or Docetaxel), a vinca alkaloid (e.g. Vinblastine, Vincristine, Vindesine or Vinorelbine), Colchicine or Podophyllotoxin.

In one embodiment, the cytotoxic agent is monomethyl auristatin E (MMAE). Because of its high toxicity, MMAE, which inhibits cell division by blocking the polymerization of tubulin, cannot be used as a single-agent chemotherapeutic drug. However, the combination of MMAE linked to an anti-CD30 monoclonal antibody (Brentuximab Vedotin, trade name Adcetris™) has been proven to be stable in extracellular fluid, cleavable by cathepsin and safe for therapy.

In one embodiment the cytotoxic agent is monomethyl auristatin F (MMAF). MMAF is an anti-microtubule/anti-mitotic agent and a carboxyl-variant of MMAE.

In one embodiment, the cytotoxic agent is a DNA-crosslinking agent, such as pyrrolobenzodiazepine or a dimeric pyrrolobenzodiazepine derivative.

In one embodiment, the cytotoxic agent is a DNA alkylating agent, such as Duocarmycin SA.

Examples of additional alkylating agents include thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analog topotecan (HYCAMTIN®), CPT-I I (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogs); podophyllotoxin; podophyllinic acid; teniposide; cryptophycins (particularly cryptophycin 1 and cryptophycin 8); dolastatin; duocarmycin (including the synthetic analogs, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma II and calicheamicin omega II; dynemicin, including dynemicin A; an esperamicin; as well as neocarzinostatin chromophore and related chromoprotein enediyne antiobiotic chromophores), aclacinomycins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex; razoxane; rhizoxin; sizofiran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; a platinum analog such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); a retinoid such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN®) combined with 5-FU and leucovovin.

Anti-hormonal agents act to regulate, reduce, block, or inhibit the effects of hormones that can promote the growth of cancer, and are often administered as systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LYI 17018, onapristone, and toremifene (FARESTON®); anti-progesterones; estrogen receptor down-regulators (ERDs); agents that function to suppress or shut down the ovaries, for example, luteinizing hormone-releasing hormone (LHRH) agonists such as leuprolide acetate (LUPRON® and ELIGARD®), goserelin acetate, buserelin acetate and tripterelin; other anti-androgens such as flutamide, nilutamide and bicalutamide; and aromatase inhibitors such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); siRNA, ribozyme and antisense oligonucleotides, particularly those that inhibit expression of genes in signaling pathways implicated in aberrant cell proliferation; vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); rmRH (e.g., ABARELIX®); lapatinib ditosylate (an ErbB-2 and EGFR dual tyrosine kinase small-molecule inhibitor also known as GW572016); COX-2 inhibitors such as celecoxib (CELEBREX®; 4-(5-(4-methylphenyl)-3-(trifluoromethyl)-IH-pyrazol-1-yl) benzenesulfonamide; and pharmaceutically acceptable salts, acids or derivatives of any of the above.

In one embodiment, the active agent is a nucleotide, such as an oligonucleotide, for example an siRNA or a miRNA.

There may be one or more units of drug per antibody molecule. The ratio between the number of drug molecules per antibody is denoted the drug-to-antibody ratio (DAR). In one embodiment, the DAR is between 1 and 10, i.e. there will be between 1 and 10 drug units per antibody molecule. In one embodiment, the DAR is between 2 and 8, for example between 3 and 6, such as 4 or 5.

Linker

A stable link between the antibody and the active agent is an important aspect of ADC technology. Linkers may e.g. be based on chemical motifs including disulfides, hydrazones or peptides (cleavable), or thioethers (noncleavable), and control the distribution and delivery of the cytotoxic agent to the target cell. Cleavable and noncleavable types of linkers have been proven to be safe in preclinical and clinical trials. For example, Brentuximab Vedotin includes an enzyme-sensitive cleavable linker that delivers the potent and highly toxic antimicrotubule agent monomethyl auristatin E (MMAE), a synthetic antineoplastic agent, to cells.

Trastuzumab Emtansine, another approved ADC, is a combination of the microtubule-formation inhibitor mertansine (DM-1), a derivative of the Maytansine, and antibody Trastuzumab (Herceptin™, Genentech/Roche), attached by a stable, non-cleavable linker.

The type of linker, cleavable or non-cleavable, lends specific properties to the delivered drug. For example, cleavable linkers can e.g. be cleaved by enzymes in the target cell, leading to efficient intracellular release of the active agent, for example a cytotoxic agent. In contrast, an ADC containing a non-cleavable linker has no mechanism for drug release, and must rely on mechanisms such as degradation of the targeting antibody, for drug release. Furthermore, as is appreciated by those skilled in the art, the linker composition may influence critical factors such as solubility and pharmacokinetic properties of the ADC as a whole.

For both types of linker, drug release is crucial for obtaining a cellular effect. Drugs which are able to freely diffuse across cell membranes may escape from the targeted cell and, in a process called "bystander killing," also attack neighbouring cells, such as cancer cells in the vicinity of the uPARAP expressing target cell.

In a preferred embodiment the ADC targeting uPARAP as disclosed herein comprises a linker that links the anti-uPARAP antibody and the active agent. The linker may be cleavable or non-cleavable. In one embodiment the linker is a cleavable linker allowing for intracellular release of the active agent inside the uPARAP expressing cells.

Cleavable groups include a disulfide bond, an amide bond, a substituted amide bond in the form of a peptide bond, a thioamide, bond, an ester bond, a thioester bond, a vicinal diol bond, or a hemiacetal. These, or other cleavable bonds, may include enzymatically-cleavable bonds, such as peptide bonds (cleaved by peptidases), phosphate bonds (cleaved by phosphatases), nucleic acid bonds (cleaved by endonucleases), and sugar bonds (cleaved by glycosidases).

The linker may e.g. be a polypeptide linker, a peptide linker or nucleic acid linker.

In particular embodiments the linker is a peptide linker. The choice of peptide sequence is critical to the success of the conjugate. In some embodiments the linker is stable to serum proteases, yet is cleaved by lysosomal enzymes in the target cell. In a non-limiting example the linker is a peptide selected from protamine, a fragment of protamine, (Arg)9, biotin-avidin, biotin-streptavidin and antennapedia peptide. Other non-nucleotide linkers include alkyl or aryl chains of about 5 to about 100 atoms. In some embodiments the linker is a nucleotide linker.

In one embodiment the linker is an enzyme-cleavable peptide-containing linker, such as a cathepsin cleavable peptide-containing linker. Cathepsin can be one of several cathepsin types, being one of a group of lysosomal proteases.

In one embodiment the linker comprises or consists of a dipeptide, such as valine-citrulline (VC) or valine-alanine (VA), which may be further connected through an amide linkage to other structural elements. Valine-citrulline-based linkers, in which the citrulline carboxyl function is modified to a substituted amide, can be cleaved by lysosomal cathepsins, whereas valine-alanine-based linkers, in which the alanine carboxyl function is modified to a substituted amide, can be cleaved by other lysosomal proteases, including other cathepsins.

In one embodiment the ADC of the present disclosure further comprises a spacer. The spacer may for example connect the linker and the active agent. In one embodiment, the spacer is paraaminobenzoic acid (PAB).

In one embodiment the spacer is or includes a polyethylenglycol spacer, such as a PEG4 spacer.

In one embodiment the ADC of the present disclosure further comprises an attachment entity. The attachment entity may for example connect the antibody and the cleavable linker, where the attachment entity is the reaction product between an antibody amino acid side chain and a reactive attachment group in the linker precursor. In one embodiment, this reactive attachment group comprises or consists of maleimide and caproic acid (MC), where maleimide reacts preferably with cysteine thiols during coupling. In other embodiments, the attachment group comprises or consists of N-hydroxysuccinimide, azides or alkynes.

In one embodiment the ADC of the present disclosure comprises an anti-uPARAP antibody as disclosed herein and the linker-drug complex Vedotin. Vedotin is a linker-drug complex comprising the cytotoxic agent MMAE, a spacer (paraaminobenzoic acid), a cathepsin-cleavable linker (Valine-citrulline dipeptide) and an attachment group consisting of caproic acid and maleimide. Vedotin is MC-VC-PAB-MMAE. Brentuximab Vedotin (trade name Adcetris™) is an example of an FDA-approved ADC comprising Vedotin.

In one embodiment, the ADC of the present disclosure comprises an anti-uPARAP antibody as disclosed herein and a linker-spacer-toxin unit being VC-PAB-MMAF.

In one embodiment, the ADC of the present disclosure comprises an anti-uPARAP antibody as disclosed herein and a linker-spacer-toxin unit being PEG4-VA-PBD.

In one embodiment, the ADC of the present disclosure comprises an anti-uPARAP antibody as disclosed herein and a linker-spacer-toxin unit being PEG4-VC-DuocarmycinSA.

In one embodiment, the ADC of the present disclosure comprises a linker-drug complex as described in US 2006/074008, which is incorporated by reference in its entirety.

The linker-drug construct may e.g. be attached to the anti-uPARAP antibody by maleimide chemistry to thiols of reduced interchain or intrachain disulphide bridges.

Therapeutic Use

The ADCs directed against uPARAP as described herein are useful for the delivery of active agents, such as therapeutic or cytotoxic agents to cells expressing uPARAP and thus for the treatment of a range of diseases and disorders characterized by uPARAP expression, in particular uPARAP overexpression.

In one embodiment, the present disclosure provides a pharmaceutical composition comprising an effective amount of a anti-uPARAP ADC, as described herein, together with a pharmaceutically acceptable buffer, diluent, carrier, adjuvant or excipient.

The pharmaceutical compositions may be prepared in a manner known in the art that is sufficiently storage stable and suitable for administration to humans and/or animals. For example, the pharmaceutical compositions may be lyophilised, e.g. through freeze drying, spray drying, spray cooling, or through use of particle formation from supercritical particle formation.

By "pharmaceutically acceptable" we mean a non-toxic material that does not decrease the effectiveness of the anti-uPARAP ADC. Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000), the disclosures of which are incorporated herein by reference).

The term "buffer" is intended to mean an aqueous solution containing an acid-base mixture with the purpose of stabilising pH. Pharmaceutically acceptable buffers are well known in the art.

The term "diluent" is intended to mean an aqueous or non-aqueous solution with the purpose of diluting the agent in the pharmaceutical preparation.

The term "adjuvant" is intended to mean any compound added to the formulation to increase the biological effect of the agent of the invention. The adjuvant may be one or more of zinc, copper or silver salts with different anions, for example, but not limited to fluoride, chloride, bromide, iodide, thiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly (vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g., for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The ADCs of the present disclosure may be formulated into any type of pharmaceutical composition known in the art to be suitable for the delivery thereof.

The ADCs of the present disclosure or pharmaceutical compositions comprising the ADCs may be administered via any suitable route known to those skilled in the art. Thus, possible routes of administration include parenteral (intravenous, subcutaneous, and intramuscular), topical, ocular, nasal, pulmonar, buccal, oral, vaginal and rectal. Also, administration from implants is possible.

In one preferred embodiment, the pharmaceutical compositions are administered parenterally, for example, intravenously, intracerebroventricularly, intraarticularly, intraarterially, intraperitoneally, intrathecally, intraventricularly, intrasternally, intracranially, intramuscularly or subcutaneously, or they may be administered by infusion techniques. They are conveniently used in the form of a sterile aqueous solution which may contain other substances, for example, enough salts or glucose to make the solution isotonic with blood. The aqueous solutions should be suitably buffered if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

In one embodiment the ADCs of the present disclosure are administered intravenously.

In one embodiment the ADCs of the present disclosure are administered subcutaneously.

In one embodiment the ADCs of the present disclosure are administered intracranially or intracerebrally.

The pharmaceutical compositions will be administered to a patient in a pharmaceutically effective amount. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce, and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. A therapeutically effective amount can be determined by the ordinarily skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit, or else several smaller dose units, and also by multiple administrations of subdivided doses at specific intervals. Alternatively, the dose may be provided as a continuous infusion over a prolonged period.

It will be appreciated by persons skilled in the art that the ADCs targeting uPARAP described herein may be administered alone or in combination with other therapeutic agents. For example, the ADCs targeting uPARAP described herein may be administered in combination with a range of anti-cancer agents, such as antimetabolites, alkylating agents, anthracyclines and other cytotoxic antibiotics, vinca alkyloids, anti-microtubule/anti-mitotic agents, histone deacetylase inhibitors, kinase inhibitors, peptide antibiotics, platinum-based antineoplastics, etoposide, taxanes, topoisomerase inhibitors, antiproliferative immunosuppressants, corticosteroids, sex hormones and hormone antagonists, cytotoxic antibiotics and other therapeutic agents.

In one embodiment the ADC of the present disclosure is administered in conjunction with additional reagents and/or therapeutics that may increase the functional efficiency of the ADC, such as established or novel drugs that increase lysosomal membrane permeability, thereby facilitating molecular entry from the lysosome interior to the cytoplasm, or drugs that increase the permeability of the blood-brain barrier.

In one embodiment the present disclosure provides a kit comprising an ADC targeting uPARAP as described herein or a pharmaceutical composition comprising same. The kit may optionally further comprise means for administering the ADC to a subject and instructions for use.

In one embodiment the present disclosure relates to a method for delivery of an active agent to a uPARAP-expressing cell in a subject comprising administering to the subject a uPARAP-directed ADC or a composition comprising a uPARAP-directed ADC as described herein, such that the active agent is delivered to said cell.

In one embodiment the present disclosure relates to the uPARAP-directed ADC or a composition comprising said uPARAP-directed ADC as described herein, for use in the delivery of an active agent to a uPARAP-expressing cell in a subject, comprising administering to the subject a uPARAP-directed ADC or a composition comprising a uPARAP-directed ADC as described herein, such that the active agent is delivered to said cell.

In one embodiment the present disclosure relates to a method for treatment of a disease or disorder characterised by cells expressing uPARAP in a subject, comprising administering to the subject a uPARAP-directed ADC or a composition comprising a uPARAP-directed ADC as described herein to said subject.

In one embodiment the present disclosure relates to the uPARAP-directed ADC or a composition comprising said uPARAP-directed ADC as described herein for use in the treatment of a disease or disorder characterised by cells expressing uPARAP.

In one embodiment the present disclosure relates to a method for inhibiting the growth of a cell expressing uPARAP in vivo or in vitro comprising administering a uPARAP-directed ADC or a composition comprising a uPARAP-directed ADC as described herein. This inhibition of growth may include cell death or may include growth inhibition without cell death.

In a particularly preferred embodiment the uPARAP-expressing cell is a tumour cell and/or a tumour associated cell and the present disclosure relates to a method for treatment of cancer in a subject, comprising administering to the subject the uPARAP-directed ADC or a composition comprising a uPARAP-directed ADC as described herein to said subject.

Tumour associated cells include, but are not limited to, activated fibroblasts, myofibroblasts, neovasculature and infiltrating cells of the macrophage-monocyte lineage or other leukocytic cell types, as well as cells of the stromal tissue surrounding the tumour.

In one embodiment the present disclosure relates to a method for inhibiting tumour progression in a subject, comprising administering to the subject a uPARAP-directed ADC or a composition comprising a uPARAP-directed ADC as described herein to said subject. This inhibition of tumor progression may include complete or incomplete eradication of tumors, or may include growth arrest without cell death.

In one embodiment the present disclosure relates to a method for inhibiting, lowering or eliminating metastatic capacity of a tumour in a subject, comprising administering to the subject a uPARAP-directed ADC or a composition comprising a uPARAP-directed ADC as described herein to said subject.

In one embodiment the tumour cells express or overexpress uPARAP.

In one embodiment the tumour associated cells express or overexpress uPARAP.

In one embodiment the present disclosure provides a method for inducing cell death and/or inhibiting the growth and/or proliferation of cells expressing uPARAP, comprising the step of administering to the individual an effective amount of an ADC targeting uPARAP as described herein, or a pharmaceutical composition comprising an ADC targeting uPARAP as described herein.

The treatment preferably induces cell death and/or inhibits the growth and/or proliferation of the uPARAP expressing cells, such as tumour cells or tumour associated cells.

In one embodiment the treatment is ameliorative.

In one embodiment the treatment is curative.

In one embodiment the present disclosure provides an ADC targeting uPARAP as described herein for the preparation of a medicament for inducing cell death and/or inhibiting the growth and/or proliferation of cells expressing uPARAP, such as tumour cells or tumour associated cells.

The expression and role of uPARAP in cancer has been investigated by several research groups; cf. review by Melander et al (Melander et al., 2015, Int J Oncol 47: 1177-1188) and article by Engelholm et al (Engelholm et al., 2016, J. Pathol. 238, 120-133).

In one embodiment the cancer is a solid tumour, wherein the tumour cells and/or the tumour associated cells express uPARAP.

In one embodiment the cancer is a solid tumour, wherein the tumour cells express uPARAP.

Examples of cancers characterized by overexpression of uPARAP include, but are not limited to, sarcoma, including osteosarcoma (Engelholm et al., 2016, J Pathol 238(1): 120-33) as well as other sarcomas, glioblastoma (Huijbers et al., 2010, PLoS One 5(3): e9808), prostate cancer and bone metastases from prostate cancer (Kogianni et al., 2009, Eur J Cancer 45(4): 685-93), breast cancer and in particular "basal like" breast cancer (Wienke et al., 2007, Cancer Res 1;67(21): 10230-40), and head- and neck cancer (Sulek et al., 2007, J Histochem Cytochem 55(4): 347-53).

In one embodiment the cancer is sarcoma, such as osteosarcoma, liposarcoma, myxofibrosarcoma, dermatofibrosarcoma protuberans (DFSP) and/or leiomyosarcoma (LMS).

In one embodiment the cancer is glioblastoma.

In one embodiment the cancer is a solid tumour, wherein the tumour associated cells express uPARAP. When uPARAP is expressed by tumour associated cells, the therapeutic effect is believed to be mediated via the so-called "by-stander" effect and/or via reduction and/or elimination of stromal cell-mediated stimulation of tumour growth and dissemination.

Examples of cancers characterized by overexpression of uPARAP in the tumour associated cells include but are not limited to breast cancer (Schnack et al., 2002, Int J Cancer 10;98(5): 656-64), head- and neck cancer (Sulek et al., 2007, J Histochem Cytochem 55(4): 347-53) and multiple other solid malignant tumours.

In one embodiment, the cancer is not a solid tumour. For instance, the ADC of the present disclosure may e.g. be used for the treatment of uPARAP-expressing leukemia, for example, from the macrophage-monocyte lineage.

In other embodiments, the disease or disorder characterised by cells expressing uPARAP is not cancer.

uPARAP is involved in bone growth and homeostasis (Madsen et al., 2013, PLoS One 5;8(8): e71261). Thus, in one embodiment the ADC of the present disclosure may be used for the treatment of a disease characterized by bone degradation, wherein the bone degradation is mediated by non-malignant cells, such as osteoporosis.

Due to its role in collagen accumulation, a role for uPARAP has also been shown in fibrosis (Madsen et al., 2012, J Pathol 227(1): 94-105). Thus, in one embodiment the ADC of the present disclosure may be used for the treatment of fibrosis, for example of kidney, lung and liver.

In one embodiment the ADC of the present disclosure may be used for the treatment of diseases and disorders associated with macrophages, including atherosclerosis and chronic inflammation.

REFERENCES

Kabat, E. A., Wu, T. T., Bilofsky, H., Reid-Miller, M., Perry, H. (1983) Sequence of proteins of immunological interest. Bethesda: National Institute of Health.

Kabat, E. A., Wu, T. T., Perry, H., Gottesman, K. and Foeller, C. (1991) Sequences of proteins of immunological interest. Fifth Edition. NIH Publication No. 91-3242.

Wu, T. T., Kabat, E. A. (2008) Pillars article: an analysis of the sequences of the variable regions of Bence Jones proteins and myeloma light chains and their implications for antibody complementarity. J. Exp. Med. 132, 211-250. J. Immunology 180, 7057-7096.

Dunbar, J., Deane, C. M. (2016) ANARCI: antigen receptor numbering and receptor classification. Bioinformatics, 32, 298-300.

Lefranc M P, Pommié C, Ruiz M, Giudicelli V, Foulquier E, Truong L, Thouvenin-Contet V, Lefranc G. (2003) IMGT unique numbering for immunoglobulin and T cell receptor variable domains and Ig superfamily V-like domains. Dev Comp Immunol. 27, 55-77.

Kunik V, Ashkenazi S, Ofran Y. (2012a) Paratome: an online tool for systematic identification of antigen-binding regions in antibodies based on sequence or structure. Nucleic Acids Res. 40 (Web Server issue): W521-4. doi: 10.1093/nar/gks480. Epub 2012 Jun. 6.

Kunik V, Peters B, Ofran Y. (2012b) Structural consensus among antibodies defines the antigen binding site. PLoS Comput Biol. 8(2): e1002388.

EXAMPLE 1

In Vitro and In Vivo Efficacy of ADCs Directed Against the N-Terminal Region of uPARAP Materials and Methods
Preparation and Evaluation of mAb-vc-MMAE ADCs Monoclonal antibodies (mAbs) against uPARAP or against trinitrophenol (TNP) were generated and produced using hybridoma technique after immunization of mice, according to established methods known in the art. In the case of mAbs against uPARAP, the host mice for immunization were gene deficient with respect to uPARAP, leading to antibodies reactive with both the human and the murine antigen. ADCs were prepared by a commonly employed conjugation method, described previously in the art (Doronina et al. 2003 Nature biotechnology 21(7): 778-84; Francisco et al., 2003. Blood 102(4): 1458-65; Hamblett et al., 2004. Clinical cancer research 10(20): 7063-70).

Antibodies were subjected to mild reduction by a 10 minute incubation at 37° C. in the presence of 10 mM DTT in a 50 mM sodium borate, 50 mM NaCl, pH 8.0 buffer at 5 mg/mL concentration, followed by removal of DTT by buffer exchange using 30 kDa NMWL centrifugal filters to fresh PBS pH 7.4 with 1 mM EDTA, then adjusted to 2 mg/mL concentration. This was followed by immediate conjugation to a 5-10 times molar surplus of maleimido-caproyl-valine-citrulline-p-aminobenzoyloxycarbonyl-monomethyl auristatin E (MC-VC-PAB-MMAE, i.e. Vedotin), dissolved in water-free DMSO to a final DMSO content of 10% v/v during conjugation for 2 hours at 37° C. The resulting mAb-vc-MMAE ADCs were purified by gel filtration on PD-10 desalting columns. The average drug-to-antibody ratio (DAR) of the resulting ADCs was determined based on the absorbance ratio of purified conjugate samples at λ=248 nm and λ=280 nm. Unmodified mAbs display an $A_{248\,nm}/A_{280}$ nm ratio of 0.43, and the $A_{MAX}$ at λ=248 nm of MMAE gives rise to a higher $A_{248\,nm}/A_{280}$ nm ratio for mAb-vc-MMAE ADCs, which has been demonstrated to reflect the DAR of the resulting ADCs (Hamblett et al., 2004. Clinical cancer research 10(20): 7063-70; Sanderson et al., 2005. Clinical Cancer Research 11: 843-852).

Cell Lines

U937, THP-1 and HT1080 cells were all obtained from ATCC. KNS42 cells were kindly provided by Lara Perryman, Biotech Research and Innovation Centre (BRIC), University of Copenhagen. CHO-K1 cells were obtained from Invitrogen. All cells were maintained in appropriate medium supplemented with 10% fetal bovine serum and 1% penicillin/streptomycin, in a 37° C., 5% $CO_2$ atmosphere incubator.

SDS-PAGE Analysis of Conjugate Species

Reducing SDS-PAGE was performed by running a 4-12% NuPAGE Bis-Tris SDS-PAGE gel, loading 5 μg of total protein per lane, reduced by boiling for 3 minutes in sample buffer in the presence of 40 mM DTT. The gels were stained using a standard 0.1% coomassie blue stain. For cathepsin B linker cleavage assay, samples were treated with recombinant human (rh) Cathepsin B according to manufacturer's instructions, using 100 ng of activated rhCathepsin B to 20 μg ADC (mAb component), in a 25 mM MES, pH 5.0 buffer, and incubation at 37° C. overnight.

ELISA Analysis of uPARAP-Binding of mAbs

A 96-well ELISA plate was coated with 25 ng/well of a soluble truncated uPARAP protein containing the first 3 N-terminal domains of human uPARAP, with intact epitope for mAb 2h9. Untreated mAbs (2h9 or aTNP), same mAbs subjected to the reduction procedure of conjugation (see above), or ADCs 2h9-vc-MMAE or aTNP-vc-MMAE, were then employed as a primary antibody, followed by a HRP-conjugated rabbit anti-mouse Ig secondary antibody. Finally an o-phenylenediamine dihydrochloride-containing substrate solution was added, and the color reaction was stopped by adding 1M $H_2SO_4$. Plates were read at 492 nm using a plate reader.

In Vitro Cytotoxicity of ADCs—Cell Viability Assay

Cells tested were seeded at low density (20-25% confluence, generally 5-10×10³ cells per well) in a 96 well plate in 90 μL of medium, and incubated overnight. The next day, mAb-vc-MMAE conjugates based on mAb 2h9, mAb 5f4 or non-targeted control mAb aTNP were prepared as a serial dilution (1:4) in PBS and added in volumes of 10 μL to each well, with a final maximum ADC concentration of 10 μg/mL mAb component. Cells were incubated for 72 hours, before 20 μL of CellTiter 96 AQueous One Solution Cell Proliferation Assay (MTS, Promega) was added, and incubated for an appropriate time for formation of color (usually 1 hour). The plates were then read at 490 nm, with background subtraction at 630 nm, using a plate reader.

In Vitro Cytotoxicity of ADCs—Cell Cycle Analysis

Cell cycle analysis was performed using a Nucleocounter NC-3000 system (ChemoMetec Denmark), using the manufacturers standard protocol for analyzing the cell cycle distribution of a population of cells, based on the DNA content of each cell. The percentage of cells in Sub-G1, G1, S, or G2/M-phases of the cell cycle was established from histogram analysis using the NucleoView NC-3000 software.

Receptor Competition and Lysosomal Protease Inhibition

For receptor competition assay, receptor depletion assay, and assay for inhibition of lysosomal proteases, U937 cells were seeded as for a cell viability assay (see above). For receptor competition assay, a constant 2h9-vc-MMAE concentration of 1 μg/mL mAb component was kept in all wells, and the unmodified competition mAb was simultaneously added in a dilution series (1:2) starting at a concentration of 8 μg/mL competitive mAb. Cells were then subjected to a 72 hour cytotoxicity cell viability assay (see above). For the assay of inhibition of lysosomal proteases, U937 cells were pre-incubated with 20 μM of E64D protease inhibitor for 2 hours, before starting a 72 hour cytotoxicity cell viability assay (see above).

Animal Experiments

All animal experiments were performed under legal approval from The Danish Veterinary and Food Administration. All reagents and cell lines used for animal experiments were tested negative for the presence of murine viruses, bacteria, mycoplasma and fungi. Animals received standard of care, and were sacrificed upon any of the following signs: loss of more than 10% of body weight, visible distress or illness, compromised food—or water intake or defecation, signs of severe inflammation in the vicinity of tumours, or tumour growth which exceeded a volume of 1000 mm$^3$ or compromised the free movement of the animals. Tumour growth was measured using electronic calipers, and tumour volumes were calculated using the formula Volume=(LxW$^2$)/2, with L being the longest dimension of the tumour, and W being the width in the perpendicular dimension.

Treatment of a Subcutaneous uPARAP-Positive 0937 Xenograft Tumour Model in Mice by s.c. Injection For tumour establishment, mice were shaved at the flank, and received a subcutaneous injection of 1×10$^6$ U937 cells, and then closely monitored in order to observe the development of solid tumours. Upon formation of palpable tumours with a volume of 50-100 mm$^3$, the mice started treatment in one of four treatment groups: 2h9-vc-MMAE (N=10), aTNP-vc-MMAE (N=9), unmodified mAb 2h9 (N=5) or PBS vehicle control (N=5). All treatments were given as a total of 4 subcutaneous doses of 3 mg/kg mAb component in the tumour area, at 4 days intervals. Injections were performed under brief isoflurane anesthesia to avoid risks for the animal handler. During treatment, the tumours were evaluated every two days, until reaching a point of sacrifice. Mice which fully lost any tumour burden were checked two times a week for a period of 3 months after ending treatment.

Treatment of a Subcutaneous uPARAP-Positive 0937 Xenograft Tumour Model in Mice by Intravenous Injection For tumour establishment, mice were shaved at the flank, and received a subcutaneous injection of 1×10$^6$ U937 cells, and then closely monitored in order to observe the development of solid tumours. Upon formation of palpable tumours with a volume of 50-100 mm$^3$, the mice started treatment in one of four treatment groups: 2h9-vc-MMAE (N=10), aTNP-vc-MMAE (N=10), unmodified mAb 2h9 (N=5) or PBS vehicle control (N=5). All treatments were given as a total of 3 intravenous doses of 5 mg/kg mAb component in the tail veins of the mice, at 4 days intervals. During treatment, the tumours were evaluated every two days, until reaching a point of sacrifice. Mice which fully lost any tumour burden were checked two times a week for a period of 3 months after ending treatment.

Statistics

All samples were done in triplicates. Error bars: Standard deviation.

Results and Conclusions

The collagen receptor uPARAP is upregulated in the tumour cells of specific cancers, including sarcomas and late-stage glioblastoma. Additionally, the receptor is most often upregulated in stromal cells surrounding solid tumours. In healthy adult individuals, the receptor displays a restricted expression, thus making it a potential target for ADC therapy.

For this purpose, we selected a monoclonal antibody, 2h9, obtained after immunization of a uPARAP gene-deficient mouse, and prepared a uPARAP-directed ADC (2h9-vc-MMAE) using a well-established conjugation method. The targeting antibody 2h9 was shown to tolerate the conjugation procedure well, with negligible loss of affinity. The resulting ADC was shown to be highly specific in killing or inducing growth arrest in uPARAP-positive cells in vitro, with U937 cells being the most sensitive cell line tested. uPARAP is a constitutively recycling receptor, directing its cargo to the lysosomal compartment. We found that ADC efficiency in highly sensitive cells such as U937 cells was completely dependent on linker cleavage, since uPARAP-dependent cytotoxicity was abrogated after inhibition of lysosomal cathepsins with E64D. Therefore, we suggest that the lysosomal capacity for cleavage of the linker contributes to differences in ADC sensitivity between different cell types, in collaboration with overall differences in sensitivity towards the conjugated cytotoxin.

For in vivo studies, we utilized a fast-growing subcutaneous xenograft tumour model with U937 cells in CB17 SCID mice. Using this model, ADC 2h9-vc-MMAE was found to be highly efficient at eradicating solid U937 tumours in vivo. Following treatment by local subcutaneous administration, 5 mice remained tumour-free 90 days after finishing the treatment regimen, hence constituting a 50% cure rate. More importantly, following treatment by intravenous administration, we observed a potent effect resulting in a 100% cure rate. Notably, this eradication of tumours was obtained without any evident adverse effects upon regular inspection of the treated mice. Importantly, the 2h9 antibody is reactive against both human and murine uPARAP, a cross-reactivity enabled by the use of a uPARAP-deficient mouse for immunization when raising the antibody. Therefore, in this xenograft model, in addition to beneficial anti-tumoural effects, any potential detrimental side effects on the host would be revealed, but no signs of detrimental effects were seen.

The epitope for the 2h9 antibody is located within the first three N-terminal domains of uPARAP, more particularly in either the CysR domain or CTLD-1. In vitro studies presented herein indicate that another ADC comprising an anti-UPARAP antibody targeting the first three N-terminal domains of uPARAP, namely 5f4, is as efficient as ADCs comprising the 2h9 antibody. The epitope for the 5f4 antibody is in the FN-II domain of uPARAP. Thus, we hypothesize that ADCs comprising anti-uPARAP antibodies directed against epitopes within the first three N-terminal domains of uPARAP are particularly efficient as ADCs.

In conclusion, the data presented here very strongly support the notion of the collagen receptor uPARAP as a versatile target in ADC cancer therapy based on expression pattern and molecular function. Furthermore, these data show that ADCs comprising antibodies directed against the first three N-terminal domains of uPARAP, such as ADC 2h9-vc-MMAE, are highly efficient for targeting of uPARAP-expressing cells in vitro and in vivo.

EXAMPLE 2

In Vitro Efficacy of MMAE-Based ADCs

In addition to the ADCs of Example 1, the following MMAE ADCs were generated: 9b7-vc-MMAE and 11c9-vc-MMAE.

mAb 2h9, mAb 5f4 and mAb 9b7 are directed against epitopes within the three N-terminal domains of uPARAP, while mAb 11c9 is an anti-uPARAP antibody directed against an epitope outside the N-terminal three domains of uPARAP.

Figure 14:
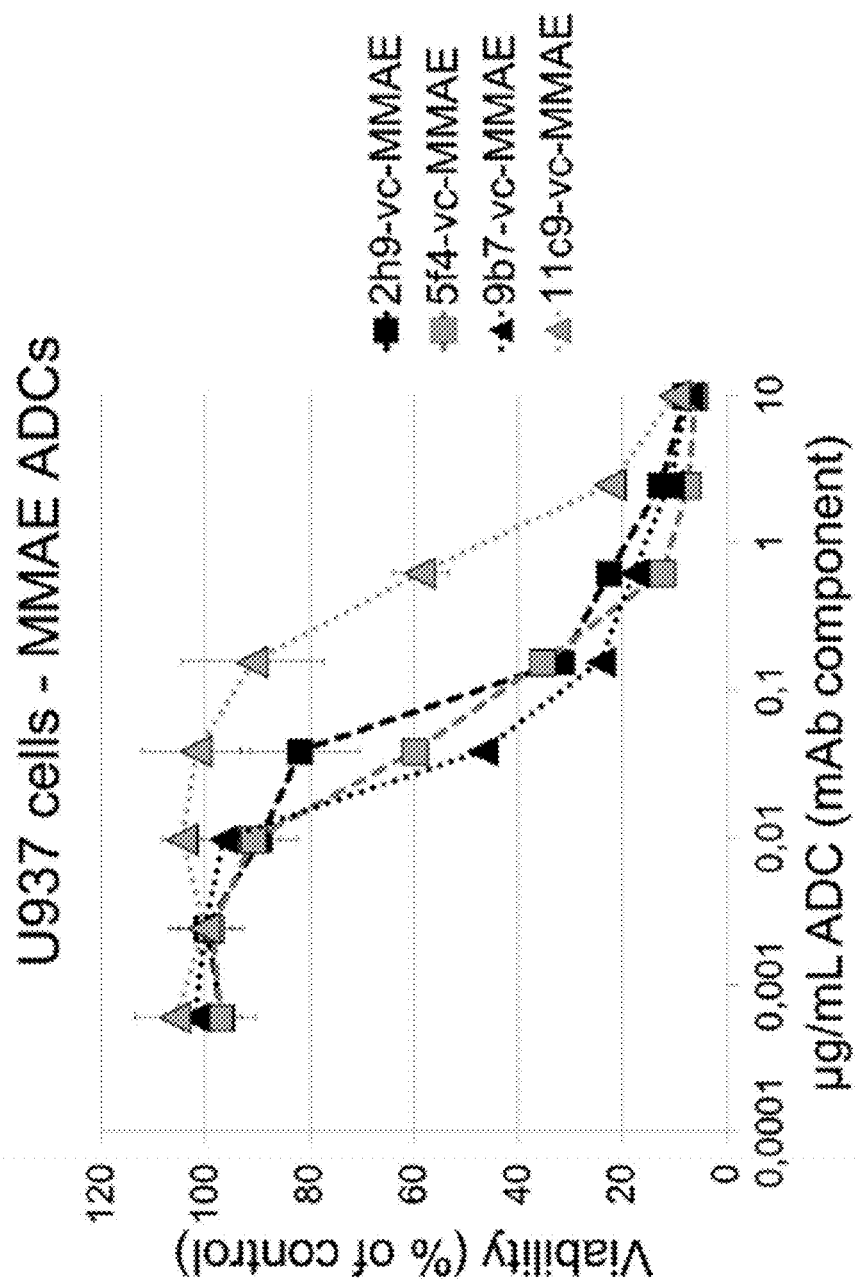
FIG. 14: Different antibodies directed against the N-terminal part of uPARAP can be utilized for efficient drug delivery in an ADC format. ADCs with the composition mAb-vc-MMAE were prepared as described in the legend to FIG. 2, using three different antibodies directed against epitopes within the three N-terminal domains of uPARAP (mAb 2h9, mAb 5f4 and mAb 9b7). For comparison, an ADC was prepared in the same manner but using an anti-uPARAP antibody directed against an epitope outside the N-terminal three domains (mAb 11c9). In vitro cell viability assays with U937 cells were then performed as described in the legend to FIG. 5, using all of these ADCs. All ADCs lead to a specific reduction in overall cell viability but with the cellular sensitivity to 2h9-vc-MMAE, 5f4-vc-MMAE and 9b7-vc-MMAE being higher than the sensitivity to 11c9-vc-MMAE.

In vitro cell viability assays with U937 cells were performed as described in Example 1, using all of these ADCs. All ADCs lead to a specific reduction in overall cell viability but with the cellular sensitivity to 2h9-vc-MMAE, 5f4-vc- MMAE and 9b7-vc-MMAE being significantly higher than the sensitivity to 11c9-vc-MMAE (FIG. 14).

Thus, the inventors conclude that ADCs comprising anti-uPARAP antibodies capable of binding to epitopes within the three most N-terminal domains of uPARAP are very efficient ADCs.

EXAMPLE 3

In Vitro Efficacy of ADCs Comprising Different Linkers, Spacers and Toxins

Different toxins can be used in an ADC format targeting the N-terminal part of uPARAP. ADCs with mAb 2h9 as the antibody component were prepared as described above but using the following linker-cytotoxin units instead of VC-PAB-MMAE:
- VC-PAB-MMAF (with MMAF being monomethyl auristatin F, a carboxyl-variant of MMAE)
- PEG4-va-PBD (with PEG4 referring to a polyethylenglycol spacer, va being valine-alanine and PBD referring to a dimeric pyrrolobenzodiazepine)
- PEG4-vc-Duocarmycin SA (with PEG4 referring to a polyethylenglycol spacer and vc being valine-citrulline)

Figure 15:
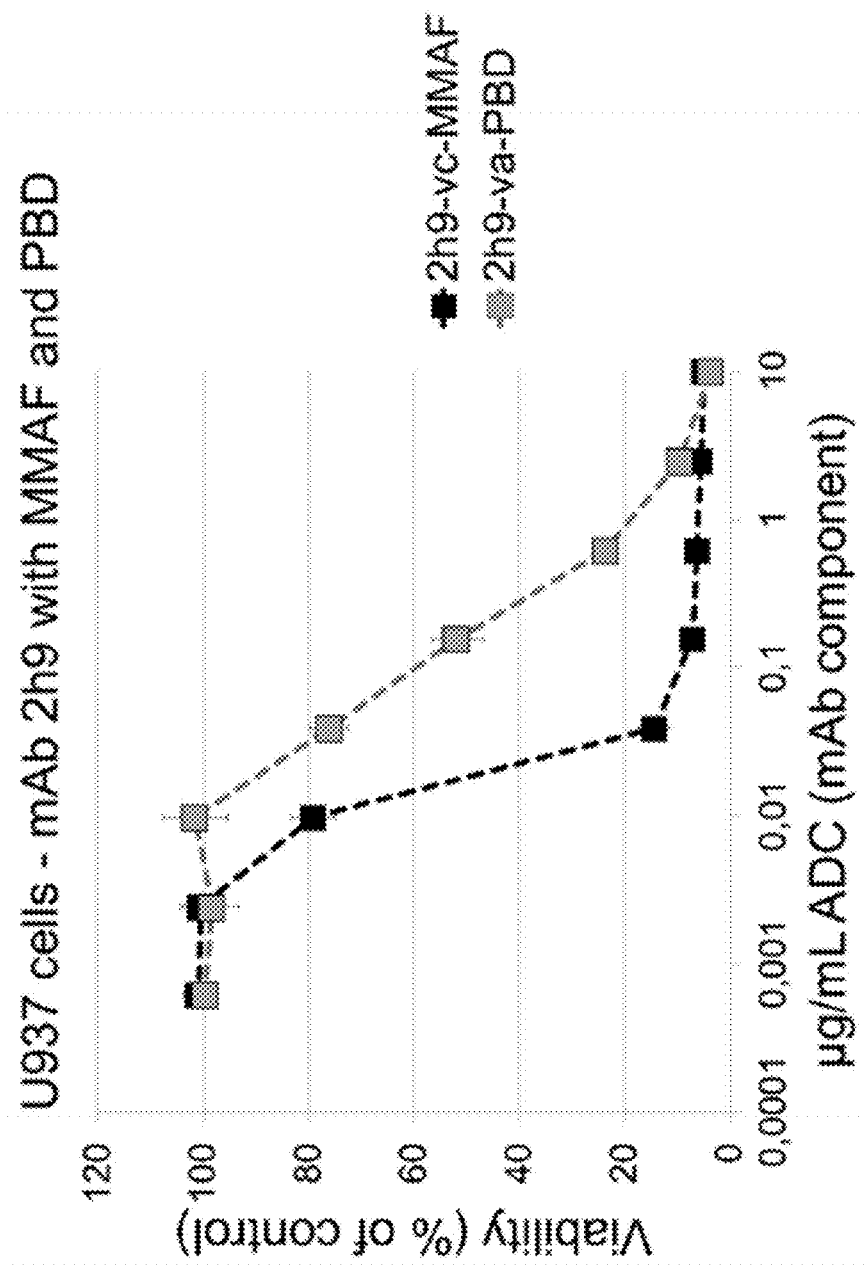
FIG. 15: Different toxins can be used in an ADC format targeting the N-terminal part of uPARAP. ADCs with mAb 2h9 as the antibody component were prepared as described in the legend to FIG. 2 but using the following linker-cytotoxin units instead of VC-PAB-MMAE: VC-PAB-MMAF (with MMAF being monomethyl auristatin F, a carboxyl-variant of MMAE) and PEG4-va-PBD (with PEG4 referring to a polyethylenglycol spacer, va being valine-alanine and PBD referring to a dimeric pyrrolobenzodiazepine). The resulting ADCs (referred to as 2h9-vc-MMAF and 2h9-va-PBD respectively) were used for in vitro cell viability assays with U937 cells, performed as described in the legend to FIG. 5. U937 cells displayed very strong sensitivity to 2h9-vc-MMAF and a more moderate sensitivity to 2h9-va-PBD.
Figure 16:
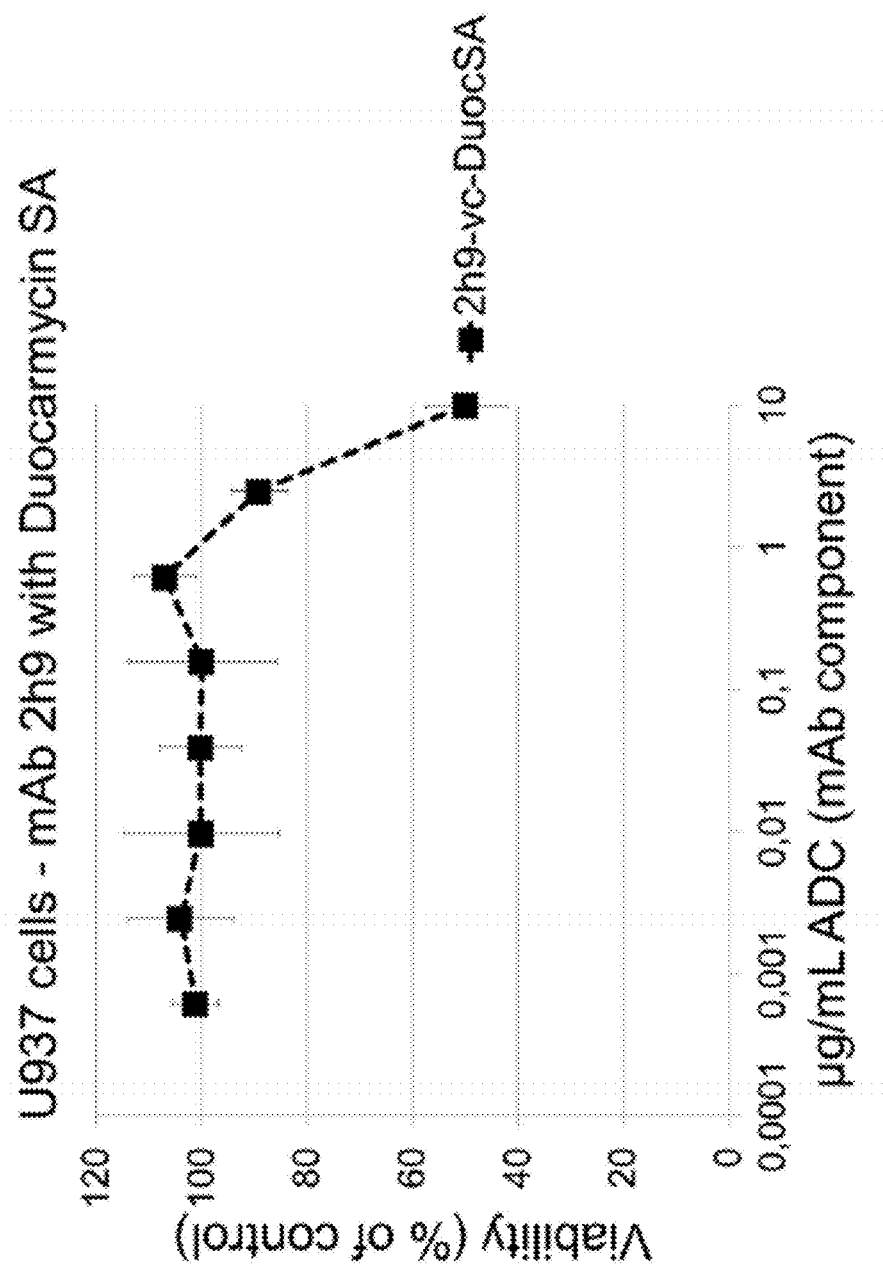
FIG. 16: An ADC with mAb 2h9 as the antibody component was prepared as described in the legend to FIG. 2 but using the following linker-cytotoxin unit instead of VC-PAB-MMAE: PEG4-vc-Duocarmycin SA (with PEG4 referring to a polyethylenglycol spacer and vc being valine-citrulline). The resulting ADC (referred to as 2h9-vc-DuocSA) was used for in vitro cell viability assays with U937 cells, performed as described in the legend to FIG. 5. U937 cells displayed a low but measurable sensitivity to 2h9-vc-DuocSA.

The resulting ADCs (referred to as 2h9-vc-MMAF, 2h9-va-PBD and 2h9-vc-DuocSA, respectively) were used for in vitro cell viability assays with U937 cells, performed as described above. U937 cells displayed very strong sensitivity to 2h9-vc-MMAF, a more moderate sensitivity to 2h9-va-PBD and a low but measurable sensitivity to 2h9-vc-DuocSA. The results are shown in FIGS. 15 and 16.

EXAMPLE 4

In Vitro Efficacy of ADCs on Human Glioblastoma Explant Cells

Figure 17A:
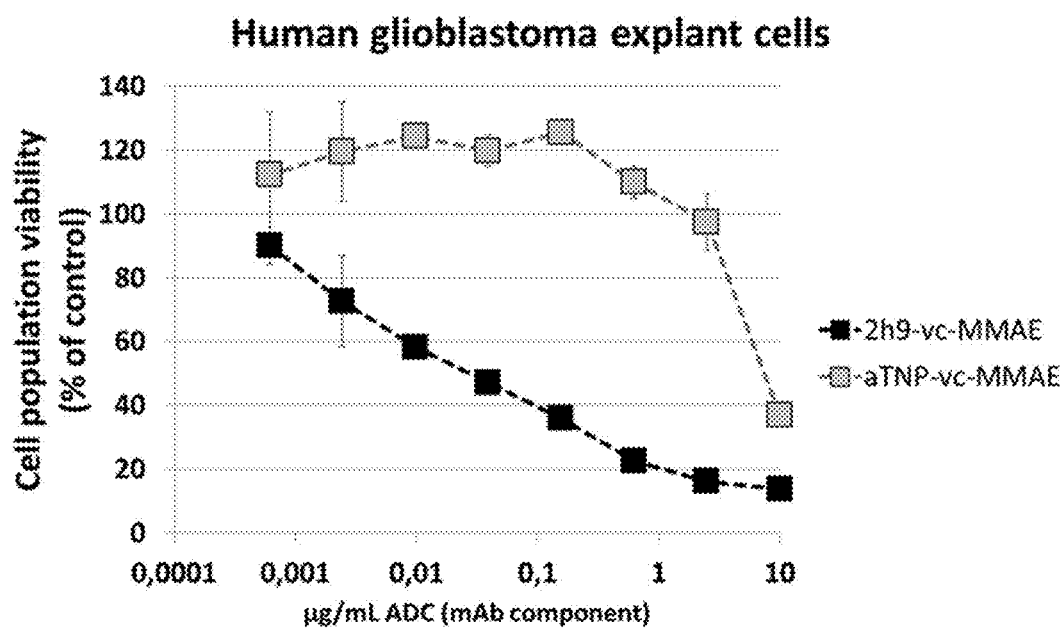
FIG. 17*a* and FIG. 17*b*: ADCs with mAbs 2h9 or aTNP as the antibody component were prepared as described in the legend to FIG. 2, using the following linker-cytotoxin units: VC-PAB-MMAE or VC-PAB-MMAF. The resulting ADCs (referred to as 2h9-vc-MMAE, 2h9-vc-MMAF, aTNP-vc-MMAE and aTNP-vc-MMAF) were used for in vitro cell viability assays using human glioblastoma explants cells and performed as described in the legend to FIG. 5. These glioblastoma explant cells showed a high degree of specific sensitivity towards uPARAP-directed ADCs, based on both the MMAE and the MMAF toxin.
Figure 17B:
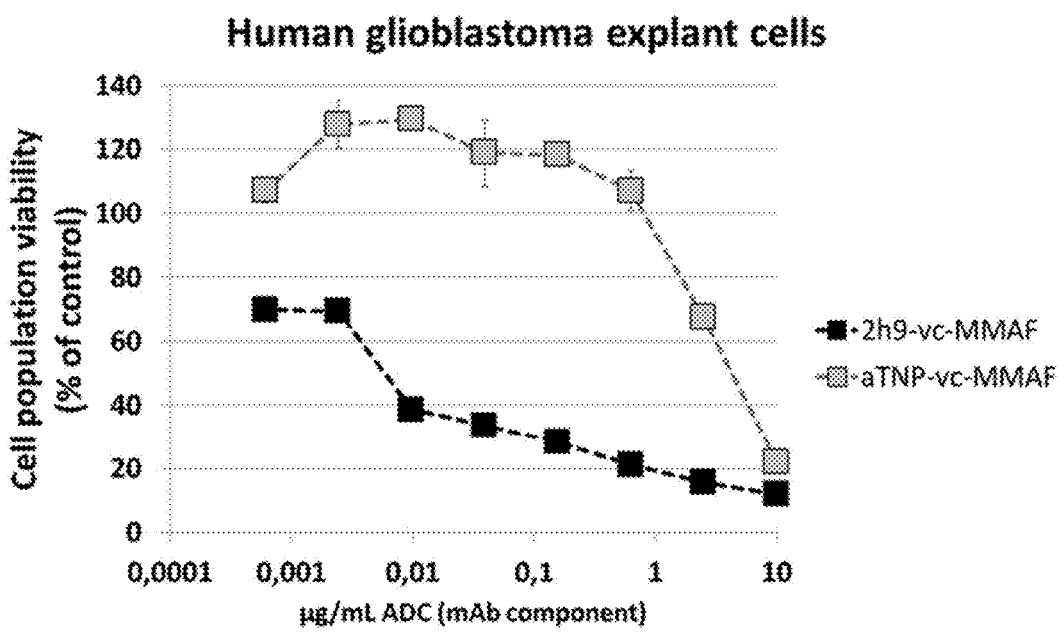

The ADCs 2h9-vc-MMAE and 2h9-vc-MMAF were tested by in vitro cell viability assays, performed as described in Example 1, for their capacity to specifically kill human glioblastoma explant cells. Glioblastoma explant cells are e.g. described in Staberg et al., 2017, Cell Oncol. 40: 21-32. These cells displayed a very strong and specific sensitivity towards both ADC 2h9-vc-MMAE, as well as ADC 2h9-vc-MMAF, thus demonstrating high efficacy of these ADCs in combating human glioblastoma cells. The results are shown in FIG. 17.

EXAMPLE 5

Recombinant Antibody

Figure 18:
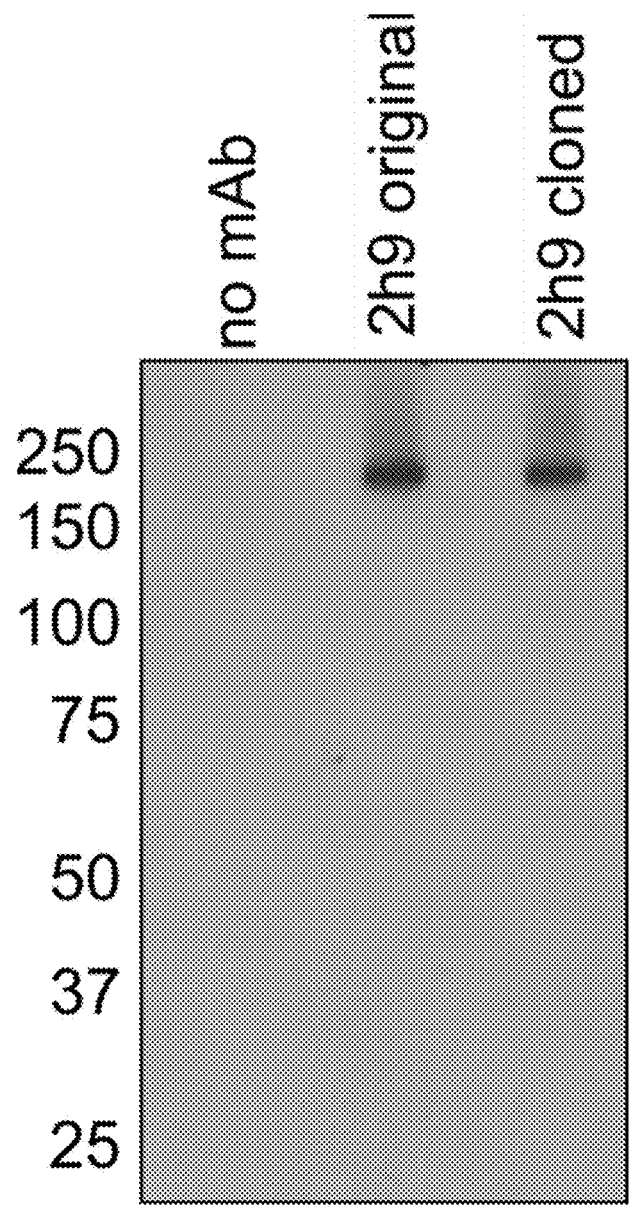
FIG. 18: A recombinant mAb 2h9 product, designated "2h9 cloned", was produced in CHO cells transfected with an expression vector including the DNA sequences encoding the light and the heavy chain of mAb 2h9 ([SEQ ID NO: 1] and [SEQ ID NO: 5], respectively). The reactivity of this product was analyzed in Western blotting and compared with mAb 2h9 produced by hybridoma cell culture ("2h9 original"). For Western blotting, a detergent cell lysate prepared from uPARAP-positive MG63 human osteosarcoma cells was analyzed, using identical concentrations of "2h9 cloned" and "2h9 original" as the primary antibodies. The two antibody products display identical reaction and both react specifically with the uPARAP protein. No reaction is seen in the absence of primary antibody (negative control).

The protein product encoded by a synthetic DNA, comprising [SEQ ID NO: 1] (light chain of monoclonal antibody 2h9 against uPARAP) and [SEQ ID NO: 5] (heavy chain of the same antibody), was expressed in CHO cells. The resulting recombinant antibody product was purified and was shown by Western blotting to specifically recognize uPARAP in the same manner as monoclonal antibody 2h9 produced by hybridoma cell culture (FIG. 18).

---

The invention claimed is:

1. A method for treating a uPARAP-expressing cancer in a subject, the method comprising:
   administering to the subject having the uPARAP-expressing cancer, the uPARAP-expressing cancer comprising tumor cells expressing uPARAP, an antibody-drug conjugate directed against uPARAP to thereby treat the cancer, the antibody-drug conjugate comprising:
   an antibody or antigen-binding fragment thereof which binds to uPARAP,
   an active agent, and
   a linker which links the antibody or antigen-binding fragment thereof to the active agent, wherein the antibody or antigen-binding fragment thereof is selected from:
   i) an antibody or antigen-binding fragment thereof comprising
      an immunoglobulin light chain variable region comprising or consisting of the amino acid sequence of SEQ ID NO: 19 or 20, and
      an immunoglobulin heavy chain variable region comprising or consisting of the amino acid sequence of SEQ ID NO: 24 or 25,
   ii) a humanised version of the antibody or antigen-binding fragment thereof of i),
   iii) a chimeric version of the antibody or antigen-binding fragment thereof of i),
   iv) an antibody or antigen-binding fragment thereof comprising an immunoglobulin light chain variable region comprising a complementarity-determining region 1 (CDR1), CDR2, and CDR3 comprising the amino acid sequences of SEQ ID NOs: 21, 22 and 23, respectively, and an immunoglobulin heavy chain variable region comprising a CDR1, CDR2, and CDR3 comprising the amino acid sequences of SEQ ID NOs: 26, 27 and 28, respectively, v) an antibody or antigen-binding fragment thereof comprising an immunoglobulin light chain variable region comprising a CDR1, CDR2, and CDR3 comprising the amino acid sequences of SEQ ID NOs: 54, 55 and 56, respectively, and an immunoglobulin heavy chain variable region comprising a CDR1, CDR2, and CDR3 comprising the amino acid sequences of SEQ ID NOs: 57, 58 and 59, respectively, and vi) a humanised version of the antibody or antigen-binding fragment thereof of iv) or v).

2. The method according to claim 1, wherein the antibody or antigen-binding fragment thereof is a Fab fragment, a Fab' fragment, a F(ab')2 fragment, an Fv, a single chain antibody (SCA), or a Fab miniantibody.

3. The method according to claim 1, wherein the antibody is a monoclonal antibody.

4. The method according to claim 1, wherein the antibody or antigen-binding fragment thereof is a fully human monoclonal antibody or antigen-binding fragment thereof.

5. The method according to claim 1, wherein the active agent is a therapeutic agent, a cytotoxic agent or a radioisotope.

6. The method according to claim 1, wherein the cancer is sarcoma.

7. The method according to claim 6, wherein the sarcoma is osteosarcoma, liposarcoma, myxofibrosarcoma, dermatofibrosarcoma protuberans (DFSP) or leiomyosarcoma (LMS).

8. The method according to claim 1, wherein the cancer is glioblastoma.

9. The method according to claim 1, wherein the cancer is prostate cancer or bone metastases from prostate cancer.

10. The method according to claim 1, wherein the cancer is breast cancer.

11. The method according to claim 1, wherein the cancer is head and neck cancer.

12. The method according to claim 1, wherein the cancer is leukaemia.

13. The method according to claim 1, wherein the antibody-drug conjugate is administered parenterally, intracerebroventricularly, intraarticularly, intra-arterially, intraperitoneally, intrathecally, intraventricularly, intrastemally, intracranially, intramuscularly or subcutaneously, or by infusion techniques.

14. The method according to claim 1, wherein the antibody-drug conjugate is administered in combination with one or more anti-cancer agents selected from antimetabolites, alkylating agents, anthracyclines, vinca alkyloids, antimicrotubule/anti-mitotic agents, DNA crosslinking agents, histone deacetylase inhibitors, kinase inhibitors, peptide antibiotics, platinum-based antineoplastics, etoposide, taxanes, topoisomerase inhibitors, antiproliferative immunosuppressants, corticosteroids, sex hormones and hormone antagonists, and cytotoxic antibiotics.

15. The method according to claim 1, wherein the tumor cells expressing uPARAP display uPARAP overexpression.

* * * * *